United States Patent
Zlotnick et al.

(10) Patent No.: US 9,131,928 B2
(45) Date of Patent: Sep. 15, 2015

(54) ELONGATED BODY FOR DEPLOYMENT IN A HEART

(75) Inventors: Amnon Zlotnick, Haifa (IL); Henry M. Israel, Bnei-Brak (IL); Boaz Harari, Tel-Aviv (IL)

(73) Assignee: Mor Research Applications Ltd., Tel-Aviv (IL)

( * ) Notice: Subject to any disclaimer, the term of this patent is extended or adjusted under 35 U.S.C. 154(b) by 426 days.

(21) Appl. No.: 12/809,641

(22) PCT Filed: Dec. 21, 2009

(86) PCT No.: PCT/IL2009/001203
§ 371 (c)(1),
(2), (4) Date: Sep. 15, 2010

(87) PCT Pub. No.: WO2010/070649
PCT Pub. Date: Jun. 24, 2010

(65) Prior Publication Data
US 2011/0029071 A1    Feb. 3, 2011

Related U.S. Application Data

(63) Continuation-in-part of application No. PCT/IL2008/001645, filed on Dec. 21, 2008.

(60) Provisional application No. 61/219,854, filed on Jun. 24, 2009, provisional application No. 61/075,143, filed on Jun. 24, 2008, provisional application No. 61/015,471, filed on Dec. 20, 2007.

(51) Int. Cl.
*A61F 2/24*     (2006.01)
*A61B 17/00*    (2006.01)
(Continued)

(52) U.S. Cl.
CPC ........... *A61B 17/00234* (2013.01); *A61B 17/04* (2013.01); *A61F 2/2451* (2013.01);
(Continued)

(58) Field of Classification Search
CPC .... A61B 17/00234; A61F 2/24; A61F 2/2487
USPC ...................... 606/80, 96, 180, 233; 623/2.11
See application file for complete search history.

(56) References Cited

U.S. PATENT DOCUMENTS 5,256,133 A * 10/1993 Spitz ............................... 600/29
6,332,893 B1    12/2001 Mortier et al.
(Continued)

FOREIGN PATENT DOCUMENTS

EP    1854414    11/2007
EP    2029053     3/2009
(Continued)

OTHER PUBLICATIONS

International Preliminary Report on Patentability Dated Jun. 30, 2011 From the International Bureau of WIPO Re. Application No. PCT/IL2009/001203.
(Continued)

*Primary Examiner* — Victor Nguyen

(57) ABSTRACT

Coronary sinus ring apparatus, including an elongated body for deployment in a coronary sinus, an aperture in a long side of the body, at least a partial lumen extending from one end of the elongated body to at least the aperture, and a guide within the elongated body positioned and shaped to guide an element inserted along the lumen to the aperture. Apparatus for treating a heart, including a delivery tube sized for and adapted for insertion into a body, a sharp tip adapted to be pushed through cardiac muscle, an elongate tensioning element, and a foldable anchor adapted to couple the elongate tension element to cardiac muscle tissue, wherein the delivery tube encloses one or both of the elongate tensioning element and the foldable anchor. Related apparatus is also described.

42 Claims, 42 Drawing Sheets

(51) Int. Cl.
*A61B 17/04* (2006.01)
*A61B 17/06* (2006.01)

(52) U.S. Cl.
CPC ............. *A61F 2/2466* (2013.01); *A61F 2/2487* (2013.01); *A61B 17/0487* (2013.01); *A61B 2017/00986* (2013.01); *A61B 2017/0417* (2013.01); *A61B 2017/0448* (2013.01); *A61B 2017/0488* (2013.01); *A61B 2017/0496* (2013.01); *A61B 2017/06052* (2013.01)

(56) References Cited

U.S. PATENT DOCUMENTS

| | | | |
|---|---|---|---|
| 6,602,288 | B1 | 8/2003 | Cosgrove et al. |
| 6,716,158 | B2 | 4/2004 | Raman et al. |
| 6,736,845 | B2 * | 5/2004 | Marquez et al. ............. 623/2.11 |
| 7,678,145 | B2 | 3/2010 | Vidlund et al. |
| 7,766,812 | B2 * | 8/2010 | Schroeder et al. ............. 600/16 |
| 2002/0169502 | A1 | 11/2002 | Mathis |
| 2004/0260317 | A1 | 12/2004 | Bloom et al. |
| 2005/0148815 | A1 | 7/2005 | Mortier et al. |
| 2005/0197527 | A1 | 9/2005 | Bolling |
| 2006/0025784 | A1 | 2/2006 | Starksen et al. |
| 2006/0259074 | A1 * | 11/2006 | Kelleher et al. ............. 606/213 |
| 2007/0203391 | A1 * | 8/2007 | Bloom et al. ............. 600/37 |
| 2007/0203575 | A1 * | 8/2007 | Forster et al. ............. 623/2.11 |

FOREIGN PATENT DOCUMENTS

| | | |
|---|---|---|
| WO | WO 02/060352 | 8/2002 |
| WO | WO 2006/044467 | 4/2006 |
| WO | PCT/US2006/031308 | 9/2006 |
| WO | WO 2006/132880 | 12/2006 |
| WO | WO 2007/038786 | 4/2007 |
| WO | WO 2007/067820 | 6/2007 |
| WO | WO 2007/095052 | 8/2007 |
| WO | WO 2007/135101 | 11/2007 |
| WO | WO 2008/067001 | 6/2008 |
| WO | WO 2008/101113 | 8/2008 |
| WO | WO 2009/081396 | 7/2009 |
| WO | WO 2010/070649 | 6/2010 |

OTHER PUBLICATIONS

Communication Pursuant to Article 94(3) EPC Dated Oct. 13, 2011 From the European Patent Office Re. Application No. 08864599.9.
International Preliminary Report on Patentability Dated Jul. 1, 2010 From the International Bureau of WIPO Re. Application No. PCT/IL2008/001645.
Communication Pursuant to Article 94(3) EPC Dated Apr. 19, 2012 From the European Patent Office Re. Application No. 08864599.9.
Communication Pursuant to Rules 161(1) and 162 EPC Dated Aug. 4, 2010 From the European Patent Office Re. Application No. 08864599.9.
Communication Relating to the Results of the Partial International Search Dated Apr. 23, 2009 From the International Searching Authority Re.: Application No. PCT/IL2008/001645.
International Search Report and the Written Opinion Dated May 26, 2010 From the International Searching Authority Re.: Application No. PCT/IL2009/001203.
International Search Report Dated Jul. 3, 2009 From the International Searching Authority Re.: Application No. PCT/IL2008/001645.
Written Opinion Dated Jul. 3, 2009 From the International Searching Authority Re.: Application No. PCT/IL2008/001645.
Jensen et al. "Impact of Papillary Muscle Relocation as Adjunct Procedure to Mitral Ring Annuloplasty in Functional Ischemic Mitral Regurgitation", Circulation, 120(Suppl.1): S92-S98, 2009.

* cited by examiner

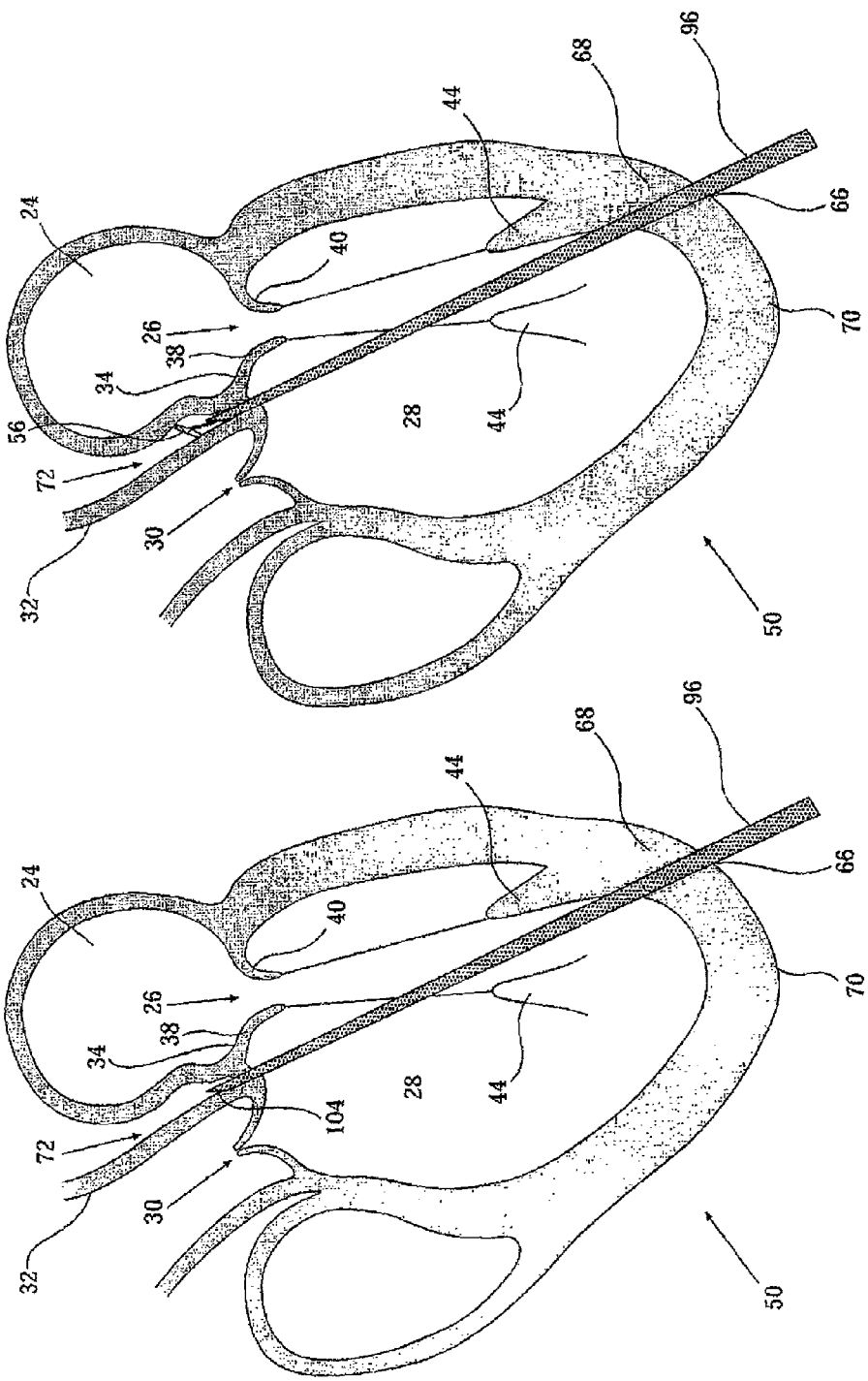

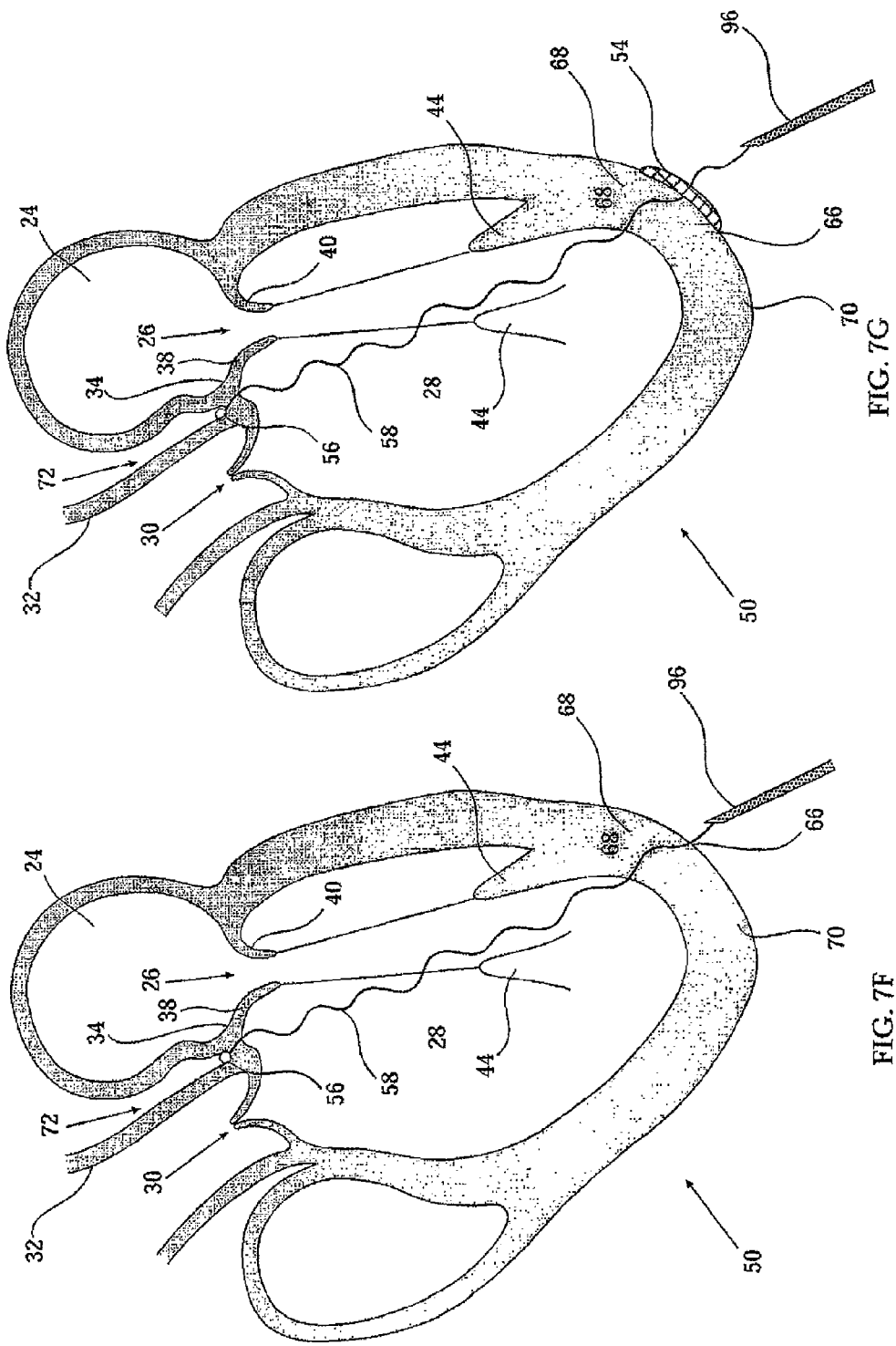

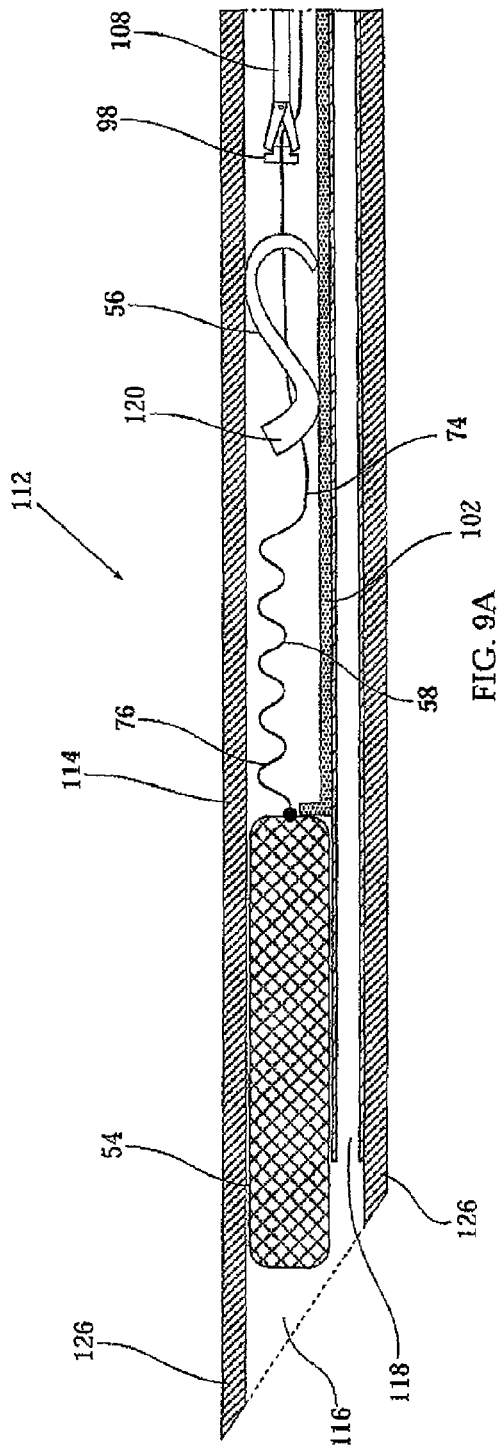
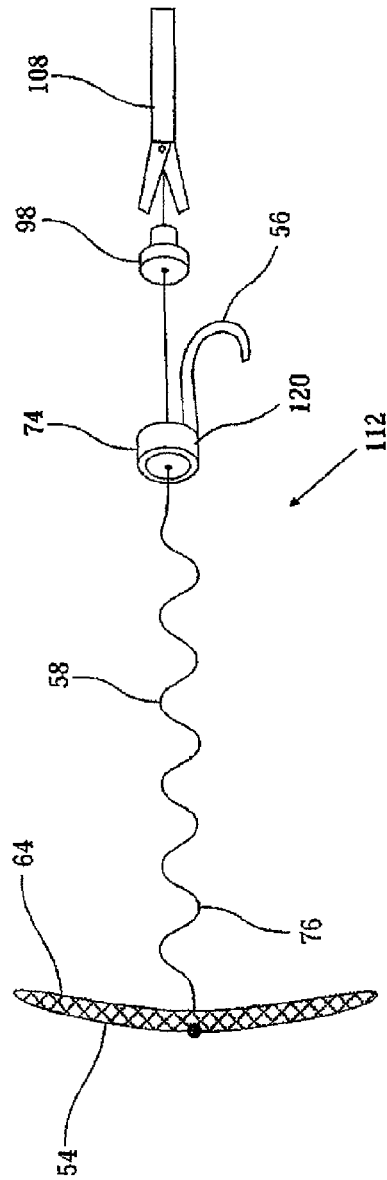
FIG. 9A
FIG. 9B

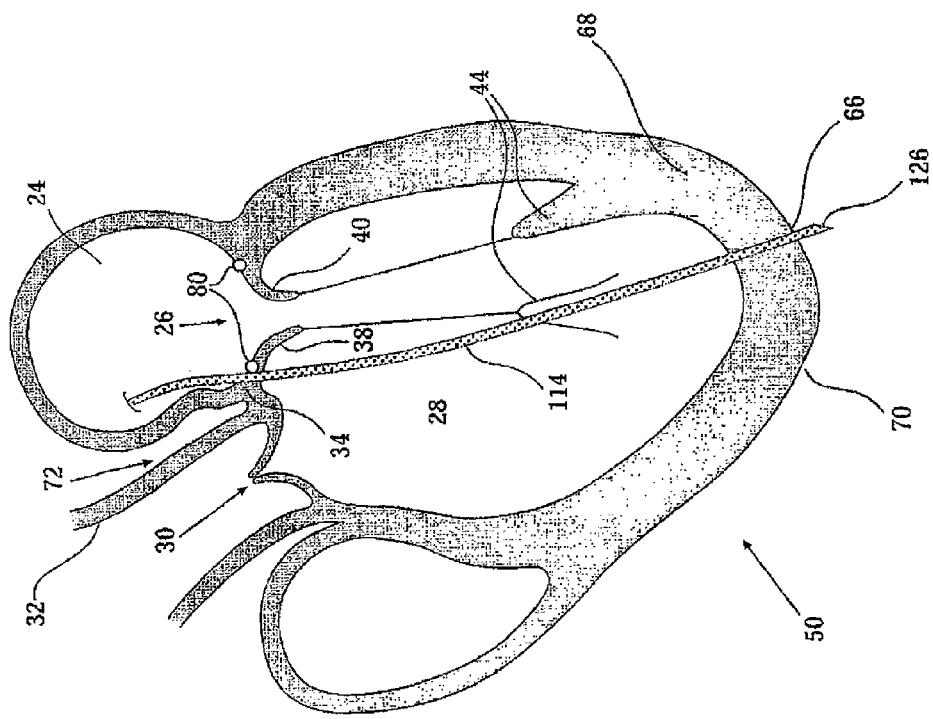
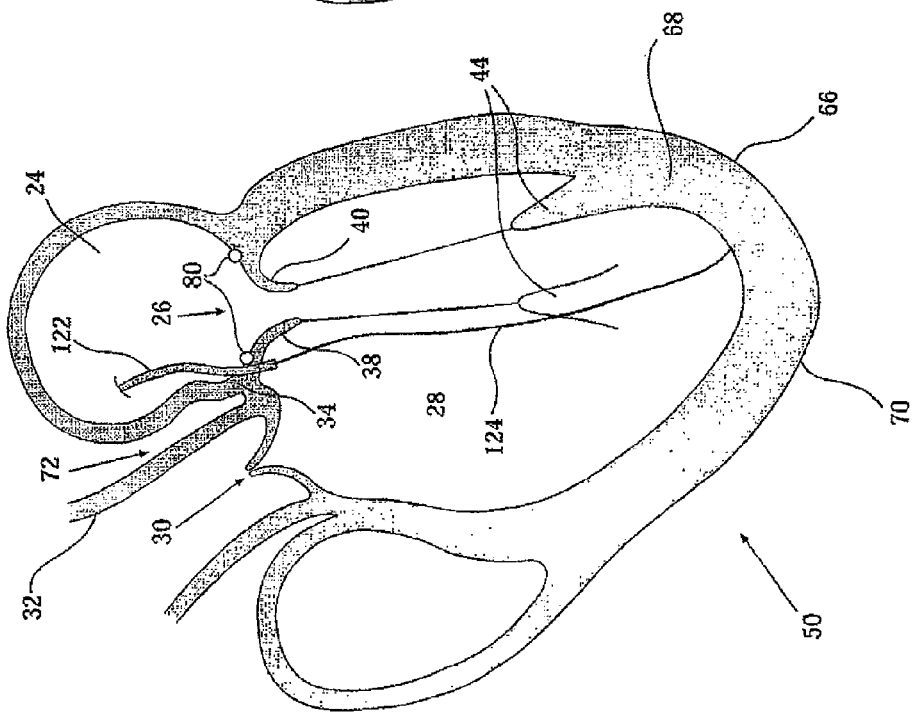
FIG. 9C
FIG. 9D

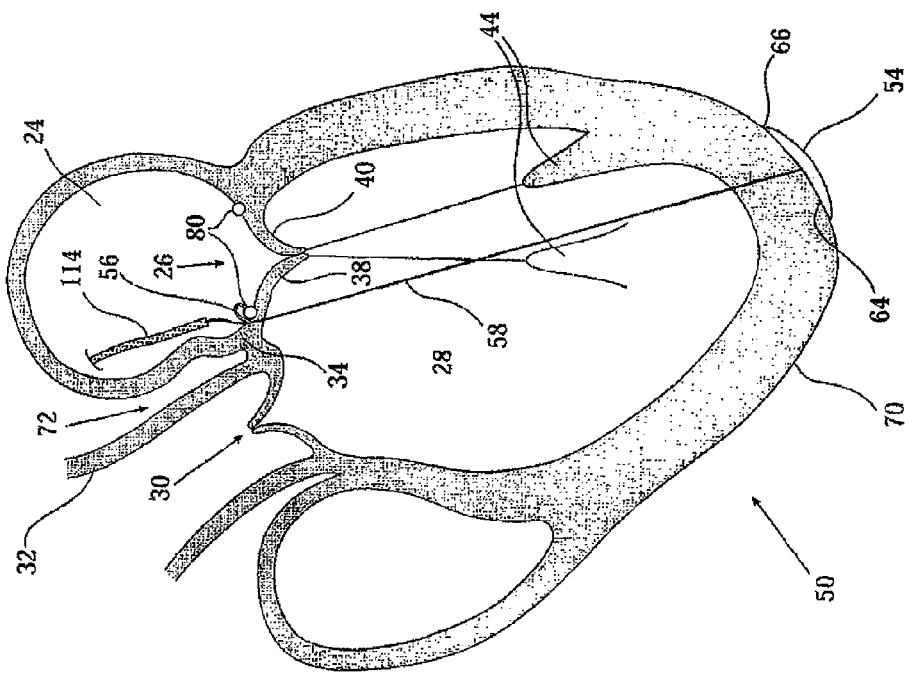
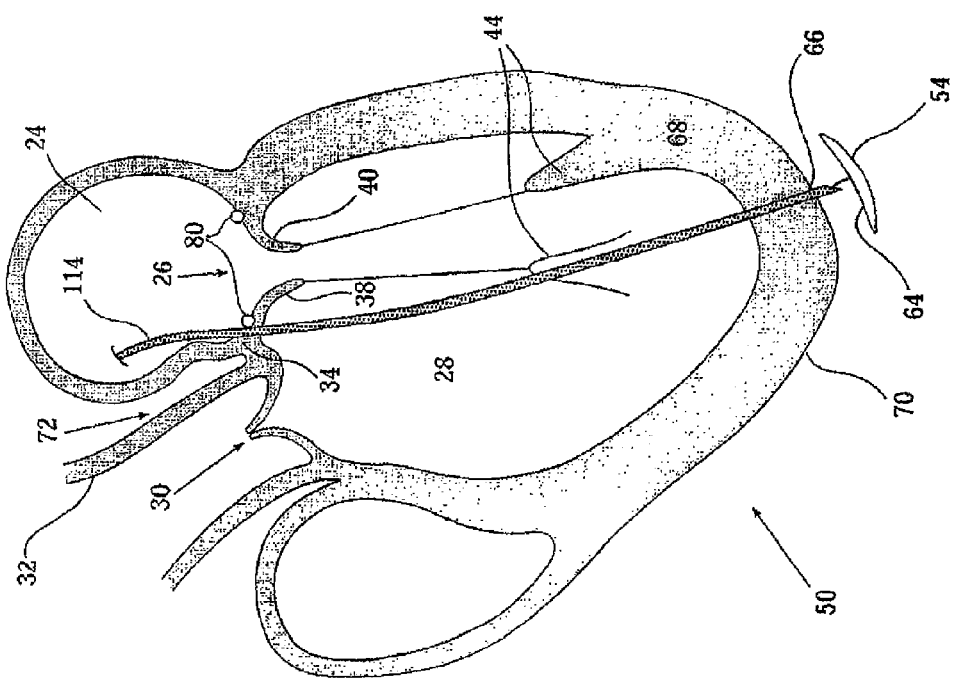

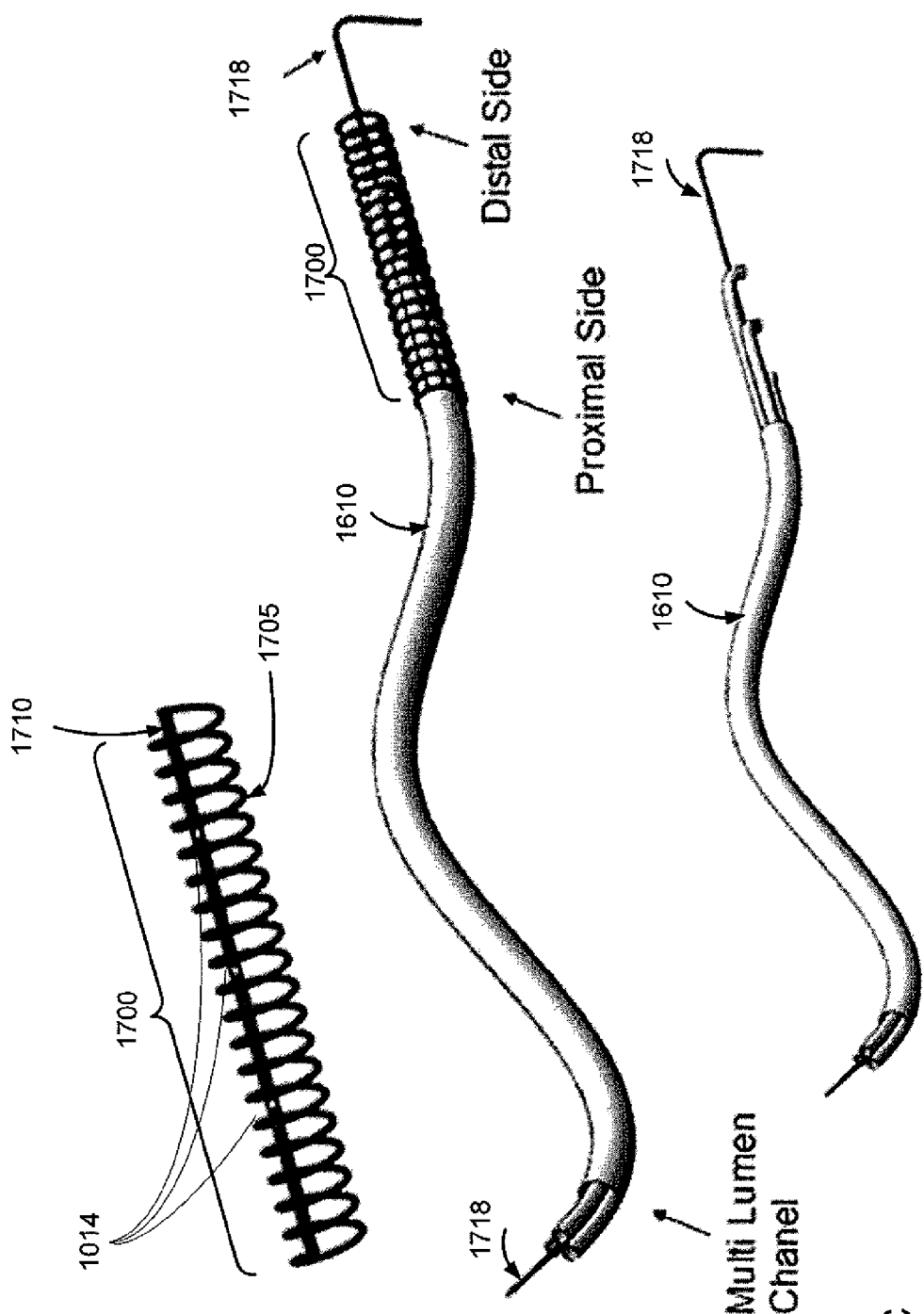

ELONGATED BODY FOR DEPLOYMENT IN A HEART

RELATED APPLICATIONS

This application is a National Phase of PCT Patent Application No. PCT/IL2009/001203 filed Dec. 21, 2009, which is a continuation-in-part (CIP) of PCT Patent Application No. PCT/IL2008/001645 filed Dec. 21, 2008, and which also claims the benefit of priority of U.S. Provisional Patent Application No. 61/219,854 filed Jun. 24, 2009.

PCT Patent Application No. PCT/IL2008/001645 claims the benefit of priority of U.S. Provisional Patent Application No. 61/015,471 filed Dec. 20, 2007, and of U.S. Provisional Patent Application No. 61/075,143 filed Jun. 24, 2008.

The contents of the above applications are all incorporated herein by reference.

FIELD OF THE INVENTION

The present invention, in some embodiments thereof, relates to the field of surgery and Cardiology and in some embodiments to methods, devices and kits potentially useful, for example, for applying force to at least a portion of a mammalian heart, for example to change the shape of the left ventricular cavity, to support a sagging cardiac wall (e.g., caused by remodeling); to improve mitral valve leaflet coaptation and/or to prevent and/or ameliorate mitral valve insufficiency and/or heart failure, to assist contractility of sagging cardiac wall. Some embodiments of the present invention allow, for example, improving mitral leaflet coaptation, for example in order to treat ischemic mitral regurgitation. In an exemplary embodiment of the invention, the surgery is carried out using minimally invasive methods and/or tools. In some exemplary embodiment of the invention the procedure is carried out using percutaneous catheterization tools.

BACKGROUND OF THE INVENTION

A typical human heart 10, depicted in cross sectional long axis view in FIG. 1, is a muscular organ that pumps deoxygenated blood through the lungs to oxygenate the blood and pumps the oxygenated blood to the rest of the body by rhythmic contractions of four chambers.

After having circulated in the body, deoxygenated blood from the body enters the right atrium 12 through the vena cava 14. Right atrium 12 contracts, pumping the blood through a tricuspid valve 16 into the right ventricle 18. Right ventricle 18 contracts, pumping the blood through the pulmonary valve 20 into the pulmonary artery 22 which divides into two branches, one for each lung. The blood is oxygenated while passing through the lungs and reenters the heart to the left atrium 24.

Left atrium 24 contracts, pumping the oxygenated blood through the mitral valve 26 into the left ventricle 28. Left ventricle 28 contracts, pumping the oxygenated blood through the aortic valve 30 into the aorta 32. From aorta 32, the oxygenated blood is distributed to the rest of the body.

Mitral valve 26, depicted in FIG. 2A (top view) and in FIG. 2B (cross sectional long axis view) is defined by an approximately circular mitral annulus 34 that defines a mitral valve orifice 36. Attached to the periphery of mitral annulus 34 is an anterior leaflet 38 and a smaller posterior leaflet 40, leaflets 38 and 40 joined at commissures 41.

The typical area of mitral valve orifice 36 in a healthy adult is between 4 and 6 cm$^2$ while the typical total surface area of leaflets 38 and 40 is approximately 12 cm$^2$. Consequently and as depicted in FIG. 2B, during ventricular systole leaflets 38 and 40 curve downwards into left ventricle 28 and coapt to accommodate the excess leaflet surface area, producing a coaptation surface 42 that constitutes a seal. The typical depth of coaptation surface 42 in a healthy heart 10 of an adult is approximately 7-8 mm.

Anterior leaflet 38 and posterior leaflet 40 are connected to papillary muscles 44 of left ventricle 28 by chordae 46.

During atrial systole, left atrium 24 contracts to pump blood into left ventricle 28 through mitral valve 26. The blood flows through mitral valve orifice 36, pushing leaflets 38 and 40 into left ventricle 28 with little resistance.

During ventricular systole, left ventricle 28 contracts to pump blood into aorta 32 through aortic valve 30. Mitral annulus 34 contracts pushing leaflets 38 and 40 inwards and downwards, reducing the area of mitral valve orifice 36 by about 20% to 30% and increasing the depth of coaptation surface 42. The pressure of blood in left ventricle 28 pushes against the ventricular surfaces of leaflets 38 and 40, tightly pressing leaflets 38 and 40 together at coaptation surface 42 so that a tight leak-proof seal is formed. To prevent prolapse of leaflets 38 and 40 into left atrium 24, papillary muscles 44 contract, pulling the edges and body of leaflets 38 and 40 into left ventricle 28 through chordae 46.

An effective seal of mitral valve 26 is dependent on a sufficient degree of coaptation, in terms of depth, area and continuity of coaptation surface 42. If coaptation surface 42 is insufficient or non-existent, there is mitral valve insufficiency, that is, regurgitation of blood from left ventricle 28 into left atrium 24. Mitral valve insufficiency leads to many complications including arrhythmia, atrial fibrillation, cardiac palpitations, chest pain, congestive heart failure, fainting, fatigue, low cardiac output, orthopnea, paroxysmal nocturnal dyspnea, pulmonary edema, shortness of breath, and sudden death.

There are a number of pathologies that lead to a mitral valve insufficiency including collagen vascular disease, ischemic mitral regurgitation, myxomatous degeneration of leaflets 38 and 40 and rheumatic heart disease as well as physical anomalies that allow leaflet prolapse (e.g., elongated or ruptured chordae 46, weak papillary muscles 44) or prevent coaptation (e.g., short chordae 46, small leaflets 38 and 40).

In ischemic mitral regurgitation (resulting, e.g., from myocardial ischemia or infarction), and other myocardial disease (e.g. Dilated cardiomyopathy) leaflets 38 and 40 and chordae 46 have normal structure and the mitral valve insufficiency results from altered geometry of left ventricle 28. As a result of ischemia, portions of the heart walls necrose. During healing, the necrotic tissue is replaced with disorganized tissue leading to remodeling of the heart which reduces coaptation through distortion/dilation of mitral annulus 34 and outwards sagging of the outer wall of left ventricle 28 which displaces papillary muscles 44.

In FIGS. 3A (top view) and 3B (cross sectional long axis view), the reduction of coaptation and incomplete closure of a mitral valve 26 during ventricular systole resulting from ischemia is depicted for an ischemic heart 50 that has undergone remodeling and suffers from ischemic mitral regurgitation. In FIG. 3B is shown how a wall of left ventricle 28 sags outwards, distorting mitral annulus 34 and displacing papillary muscles 44 outwards which, through chordae 46, pulls leaflets 38 and 40 apart and into left ventricle 28, reducing coaptation.

Initially, ischemic mitral regurgitation is a minor problem, typically leading only to shortness of breath during physical exercise due to the fact that a small fraction of blood pumped by left ventricle 28 is pumped into left atrium 24 and not through aortic valve 30, reducing heart capacity. To compensate for the reduced capacity, left ventricle 28 contracts harder and remodeling continues. Ultimately leaflet coaptation is nonexistent as leaflets 38 and 40 are pulled further and further apart, leading to more blood regurgitation, further increasing the load on left ventricle 28, and further remodeling. Ultimately, the left side of the heart fails.

Apart from humans, mammals that suffer from mitral valve insufficiency include horses, cats, dogs, cows, sheep and pigs.

U.S. Pat. Nos. 3,656,185, 6,183,512 and 6,250,308 and United States Patent applications published as US 2002/065554, US 2003/0033009, US 2004/0138745 or US 2005/0038509 describe ways of treating mitral dysfunction.

U.S. Pat. No. 6,332,893 describes valve to myocardium tension members.

It has been proposed to change the shape of a left ventricle 28 and/or to support the walls of a left ventricle 28 to improve the functioning of a mitral valve 26, see for example, the U.S. Patent Application published as US 2006/0281968, U.S. Pat. No. 7,238,152 (as well as products of Paracor Medical, Inc., Sunnyvale, Calif., USA) and U.S. Pat. Nos. 6,077,214, 6,332,893 and 6,723,038 (as well as products of Myocor, Inc., Maple Grove, Minn., USA such as Coapsys®).

In "RING plus STRING": Papillary muscle repositioning as an adjunctive repair technique for ischemic mitral regurgitation" by Langer, F and Schafers, H-J in J Thorac Cardiovasc Surg 2007; 133; 247-249 is taught implantation of an undersized annuloplasty ring together with deployment of a suture passing through the left ventricle 28 from the head of the posterior papillary muscle 44 to the midseptal fibrous annulus through the aortic wall underneath the commissures of two aortic valve 30 leaflets. While the heart beats and under observation of an imaging device, the suture is tensioned so as to pull the papillary muscle 44 towards the aortic wall until a desired degree of mitral valve leaflet coaptation is observed. The method leads to an increased tension applied to papillary muscle 44, which may stretch and elongate, affecting the angle at which papillary muscle 44 pulls leaflet 38.

SUMMARY OF THE INVENTION

Some embodiments of the present invention provide methods, devices and kits useful for guiding a tip of an element passed through a lumen to a side wall of the lumen. In some embodiments, the lumen is a coronary sinus of the heart, and the element is a puncturing device for puncturing a wall of the coronary sinus.

Some embodiments of the present invention provide methods, devices and kits useful for applying pressure to at least a portion of a mammalian heart, for example to the left ventricle. In some embodiments, the applied pressure has a beneficial effect, for example, changing the shape of a left ventricle and/or improving coaptation of mitral valve leaflets and/or supporting sagging portions of the cardiac walls and/or assisting heart contractility and/or relieving/redistributing pressure inside the heart.

There is provided in accordance with an exemplary embodiment of the invention, apparatus for treating a heart, comprising:

a delivery tube sized for and adapted for insertion into a body;

a sharp tip adapted to be pushed through cardiac muscle;

an elongate tensioning element; and at least one anchor on said elongate tensioning element and adapted to couple said elongate tension element to cardiac muscle tissue, wherein said delivery tube encloses one or both of said element and said at least one anchor.

In an exemplary embodiment of the invention, said sharp tip is formed on an end of said delivery tube. Optionally, said delivery tube is smooth enough to slide through said cardiac muscle after penetration of said cardiac muscle by said sharp tip.

In an exemplary embodiment of the invention, the apparatus comprises a second anchor, mounted on said elongate tensioning element and configured to anchor said elongate tensioning element to different cardiac muscle tissue at a spaced apart position from said at least one anchor. Optionally, said at least one anchor and said second anchor are configured to be urged against opposite parts of said hearts by said elongate tensioning element. Optionally, said at least one anchor and said second anchor are adapted to not engage said heart absent tension from said elongate tensioning element.

In an exemplary embodiment of the invention, one or both of said at least one anchor and said second anchor are adapted to be axially moved along said elongate tensioning element.

In an exemplary embodiment of the invention, one or both of said at least one anchor and said second anchor includes a locking mechanism for selectively locking at a desired position along said elongate tensioning element.

In an exemplary embodiment of the invention, said tube is flexible enough to pass through a venous system to the heart. Optionally, said tube is flexible enough to bend with a turning radius smaller than 5 mm. Optionally or alternatively, the apparatus comprises at least one catheter guide adapted to lie within a coronary sinus, said guide including a channel which defines a pathway that includes a substantially right angle turn, with a turning radius of less than 15 mm.

In an exemplary embodiment of the invention, said anchor is preassembled with said elongate tensioning element.

In an exemplary embodiment of the invention, said tube includes a separate guidewire channel.

In an exemplary embodiment of the invention, the apparatus comprises a guidewire which is sharp enough and stiff enough to penetrate cardiac muscle.

In an exemplary embodiment of the invention, said at least one anchor is configured to lie on an outside of a left ventricle and is in the form of a pad. Optionally, said at least one anchor is configured to lie on an outside of a left ventricle and includes a plurality of elongate extensions adapted to lie against said outside.

In an exemplary embodiment of the invention, said at least one anchor is configured to lie on an outside of a left ventricle and has a surface area for contact with said surface, of at least 6 sq. cm.

In an exemplary embodiment of the invention, said at least one anchor is a hook adapted to engage a rod-like element.

In an exemplary embodiment of the invention, said at least one anchor is a rod-like element.

In an exemplary embodiment of the invention, said elongate tensioning element dissipates after less than 6 months.

In an exemplary embodiment of the invention, said elongate tensioning element has a length of between 4 and 15 cm.

There is provided in accordance with an exemplary embodiment of the invention, coronary sinus guide apparatus, comprising:

(a) an elongate body adapted to conform to the shape of a coronary sinus;

(b) an aperture in a long side of said body, having a diameter of at least 1 mm;

(c) a partial lumen extending from one end of said body at least to said aperture; and (d) a guide within said body positioned and shaped to guide an element inserted along said pathways to said aperture.

In an exemplary embodiment of the invention, said guide is fixed. Optionally, flow of blood past and around said guide to an opposite end of said body is substantially blocked. Optionally, the portion of said body extending past said guide is substantially solid and having a cross-section of at least 80% of a cross-sectional area of said body.

In an exemplary embodiment of the invention, the apparatus comprises a guidewire channel extending past said guide and leading into said partial lumen.

Optionally, said guidewire channel is positioned relative to said guide and said partial lumen in a manner which impedes insertion of a guidewire through said partial lumen and into said guidewire channel. Optionally, said channel is substantially continuous with a wall of said partial lumen.

In an exemplary embodiment of the invention, the apparatus comprises a guidewire with an at least partially pre-bent tip.

In an exemplary embodiment of the invention, the apparatus comprises a funnel-like wire guide at an entrance to said partial lumen.

In an exemplary embodiment of the invention, the apparatus comprises an anchoring element at least one end of said body.

In an exemplary embodiment of the invention, said body has a minimal cross-sectional diameter of less than 15 mm in a part designated for the coronary sinus, such that the coronary sinus would not be blocked by the apparatus.

In an exemplary embodiment of the invention, said body is long enough and stiff enough to modify a shape of a Mitral valve annulus.

In an exemplary embodiment of the invention, the apparatus is configured for permanent implantation in a coronary sinus.

In an exemplary embodiment of the invention, the apparatus comprises a catheter adapted to fit through said aperture and including a tip for penetrating cardiac muscle tissue.

There is provided in accordance with an exemplary embodiment of the invention, a method of treating a heart, comprising:
(a) accessing a heart through a hole in the body with a diameter of less than 3 cm;
(b) penetrating a first wall of the heart;
(c) second penetrating a second wall of the heart;
(d) coupling an elongate tensioning element to said second wall; and
(e) second coupling said elongate tensioning element to said first wall.

Optionally, said coupling and said second coupling comprise:
releasing an anchor distal to said second wall; and
releasing a second anchor proximal to said first wall.

Optionally, said penetrating comprises penetrating with a hollow tube.

In an exemplary embodiment of the invention, said penetrating comprises penetrating a wall of the left ventricle from outside of the heart.

In an exemplary embodiment of the invention, said penetrating comprises penetrating a wall of the left ventricle from inside of the heart.

In an exemplary embodiment of the invention, said accessing comprises accessing through a vascular system. Optionally, said accessing comprises accessing through an atrial septum. Optionally or alternatively, said accessing comprises accessing through a coronary sinus.

In an exemplary embodiment of the invention, the method comprises adjusting a length of said elongate tensioning element inside said heart.

In an exemplary embodiment of the invention, the method comprises selecting a desired effect on said heart of said elongate tensioning element and selecting the locations of said penetrations in accordance with said selecting.

In an exemplary embodiment of the invention, the method comprises treating a disorder selected from the group of Heart failure, Mitral valve insufficiency and Dilated Cardiomyopathy, using said elongate tensioning element.

In an exemplary embodiment of the invention, the method comprises repeating at least one of said coupling and said second coupling for a plurality of elongate tensioning elements.

In an exemplary embodiment of the invention, said (b) penetrating and said second penetrating (c) comprise penetrating at other than apical and papillary muscle positions.

In an exemplary embodiment of the invention, said coupling and said second coupling are selected so that said elongate tensioning element is not tensioned by said walls over the entire cycle of the heart.

There is provided in accordance with an exemplary embodiment of the invention, cardiac tensioning apparatus, comprising:
(a) an elongate tensioning element;
(b) at least one anchor adapted to couple said elongate tensioning element to cardiac tissue, at a first position along said elongate tensioning element; and
(c) a hook adapted to engage a rod like element, at a second position along said elongate tensioning element.

There is provided in accordance with an exemplary embodiment of the invention, a method of having a beneficial effect on a heart, comprising:
(a) identifying that a heart suffers from one or more of Heart failure, Mitral valve insufficiency and Dilated Cardiomyopathy;
(b) selecting a desired limit on a geometry of the heart; and
(c) implanting at least one elongate tensioning element at a position and length which provide one or both of a desired limit on geometry and desired assistance to cardiac muscle wall movement. Optionally, said at least one elongate tensioning element comprises a plurality of elongate tensioning elements. Optionally or alternatively, said at least one elongate tensioning element is not implanted at a papillary muscle or an apex of the heart According to an aspect of some embodiments of the present invention there is provided a method for applying pressure to at least a portion of a mammalian heart, comprising: a) providing an implantable device including a first anchor, a second anchor and at least one elongated tensioning member (e.g., a filamentous tensioning member such as a suture, a filament or the like); b) deploying the first anchor so as to contact an external wall of a left ventricle of the heart; c) deploying the second anchor in proximity to the aortic side of a mitral valve annulus of the heart; and d) for at least a first of the tensioning members, securing a first portion of the tensioning member to the first anchor and securing a second portion of the tensioning member to the second anchor so that the tensioning member passes from the first anchor, through the left ventricle of the heart to the second anchor thereby defining a distance separating the first anchor and the second anchor when the tensioning member is taut so that the first anchor and the second anchor apply pressure each to a portion of the heart. In some embodiments, the pressure applied to the portion of the heart is at least during ventricular diastole. In some embodiments, the pressure applied to a portion of the heart is at least during ventricular systole. In some embodiments, the second anchor is deployed at least partially inside the transverse pericardial sinus of the heart. In some embodiments, the second anchor is deployed inside the transverse pericardial sinus of the heart. In some embodiments, the second anchor is deployed at least partially inside the left ventricle, contacting the aortic-mitral curtain portion of the mitral valve annulus. In some embodiments, the second anchor comprises an annuloplasty ring or an artificial heart valve. In some embodiments, the second anchor is deployed so as to engage an implantable prosthesis, e.g., an annuloplasty ring or a prosthetic heart valve. In some embodiments, the second anchor is deployed so as to engage a previously-deployed implantable prosthesis such as an annuloplasty ring or a prosthetic heart valve.

According to an aspect of some embodiments of the present invention there is also provided a method for applying pressure to at least a portion of a mammalian heart inside which an implantable prosthesis (e.g., an annuloplasty ring, a prosthetic heart valve) has been previously deployed, comprising: a) providing an implantable device including a first anchor (such as described above), a second anchor (such as described above) and at least one elongated tensioning member (such as described above); b) deploying the first anchor so as to contact an external wall of a left ventricle of the heart (as described above); c) (optionally while the heart is beating) engaging the implantable prosthesis so as to deploy the second anchor in proximity to a mitral valve annulus of the heart; and d) for at least a first of the tensioning members, securing a first portion of the tensioning member to the first anchor and securing a second portion of the tensioning member to the second anchor so that the tensioning member passes from the first anchor, through the left ventricle of the heart to the second anchor thereby defining a distance separating the first anchor and the second anchor when the tensioning member is taut so that the first anchor and the second anchor apply pressure each to a portion of the heart. In some embodiments, the pressure applied to the portion of the heart is at least during ventricular diastole. In some embodiments, the pressure applied to a portion of the heart is at least during ventricular systole. In some embodiments, the second anchor is deployed at least partially inside the transverse pericardial sinus of the heart. In some embodiments, the second anchor is deployed at least partially inside the left ventricle, contacting the aortic-mitral curtain portion of the mitral valve annulus.

In some embodiments, the heart is the heart of a non-human animal. In some embodiments, the heart is the heart of a human. In some embodiments, the heart is the heart of a non-living animal.

In some embodiments, the tensioning member passing through the left ventricle substantially avoids penetrating a papillary muscle.

In some embodiments, the first anchor is deployed so as to contact an external wall of the left ventricle in proximity of the apex of the heart.

In some embodiments, the first anchor is deployed substantially entirely outside the heart.

In some embodiments, the tensioning member passes from the first anchor through at least a portion of an external wall of the left ventricle of the heart. In some embodiments, the tensioning member passes from the first anchor through an external wall of the left ventricle of the heart.

In some embodiments, the first anchor comprises at least one assembly including a contact face and the deploying of the first anchor comprises placing the contact face against an outer surface of the heart.

In some embodiments, the first anchor comprises at least two discrete assemblies each including a contact face and the deploying of the first anchor comprises placing the contact face of each assembly against a different part of an outer surface of the heart.

In some embodiments, the method further comprises: at least one day after "d" (the securing of a first portion of the tensioning member to the first anchor and the securing of a second portion of a tensioning member to the second anchor), changing a distance separating the first anchor and the second anchor defined by a tensioning member. In some embodiments, the changing of the distance decreases the pressure applied to the heart. In some embodiments, the changing of the distance increases the pressure applied to the heart.

In some embodiments, changing the distance comprises engaging the first anchor and/or the tensioning member (proximal to the first anchor, e.g., from the direction of the cardiac apex) so as to change the distance, in some embodiments while the heart is beating.

In some embodiments, changing the distance comprises engaging the second anchor and/or the tensioning member (proximal to the second anchor) from the transverse pericardial sinus of the heart so as to change the distance, in some embodiments while the heart is beating.

In some embodiments, the implantable device comprises at least two of the tensioning members, and the method further comprises, for each of the tensioning members: securing a first portion of the tensioning member to the first anchor and securing a second portion of the tensioning member to the second anchor so that the tensioning member passes through the left ventricle thus defining a distance separating the first anchor and the second anchor when the tensioning member is taut so that the first anchor and the second anchor apply pressure to a portion of the heart.

In some embodiments the method further comprises: at least one day after "d" (securing a first portion of the tensioning member to the first anchor and securing a second portion of the tensioning member to the second anchor), changing a distance separating the first anchor and the second anchor defined by at least one the tensioning member. In some embodiments the method further comprises: at least one day after "d" (securing a first portion of the tensioning member to the first anchor and securing a second portion of the tensioning member to the second anchor), changing a distance separating the first anchor and the second anchor defined by at least two the tensioning members.

In some embodiments, changing a distance defined by a tensioning member comprises, engaging the second anchor and/or the tensioning member (in proximity of the second anchor) from the transverse pericardial sinus of the heart so as to change the distance, in some embodiments while the heart is beating.

In some embodiments, changing a distance defined by a tensioning member comprises engaging the first anchor and/or the tensioning member (in proximity of the first anchor, for example from the direction of the cardiac apex) so as to change the distance, in some embodiments while the heart is beating.

According to an aspect of some embodiments of the present invention there is also provided an implantable device for applying pressure to at least a portion of a mammalian heart that in some embodiments is useful for implementing some embodiments of the methods described above, the implantable device, comprising: a) a first anchor configured for contacting a surface of an external wall of a left ventricle of a heart; b) a second anchor configured for deployment in proximity to the aortic side of a mitral valve annulus of a heart; and c) at least one flexible elongated tensioning member secured to the first anchor and to the second anchor thus substantially defining a distance separating the first anchor and the second anchor when the tensioning member is taut.

In some embodiments, the second anchor is configured for deployment at least partially inside the left atrium of a heart. In some embodiments, the second anchor comprises an annuloplasty ring or an artificial heart valve. In some embodiments, the second anchor is configured to engage an implantable prosthesis such as an annuloplasty ring or prosthetic heart valve, in some embodiments a previously-deployed implantable prosthesis such as an annuloplasty ring or prosthetic heart valve. In some embodiments, the second anchor is configured to contact the aortic-mitral curtain portion of a mitral valve annulus.

In some embodiments, the second anchor is configured for deployment at least partially inside the transverse pericardial sinus of a heart. In some embodiments, the second anchor is configured for deployment inside the transverse pericardial sinus of a heart. In some such embodiments, the second anchor comprises an elongated member configured to fit inside a transverse pericardial sinus, for example having a length of between about 1 cm and about 6 cm (in some embodiments between about 1 cm and about 2 cm) and a width of between about 2 mm and about 5 mm (in some embodiments between about 2 mm and about 3 mm). In some embodiments, such a second anchor is axially flexible. In some embodiments, such a second anchor is a substantially rigid rod, in some embodiments a straight or curved rod.

According to an aspect of some embodiments of the present invention there is also provided an implantable device for applying pressure to at least a portion of a mammalian heart that in some embodiments is useful for implementing some embodiments of the methods described above, the implantable device, comprising: a) a first anchor configured for contacting a surface of an external wall of a left ventricle of a heart; b) a second anchor configured for deployment in proximity a mitral valve annulus of a heart by engaging an implantable prosthesis (e.g., an annuloplasty ring, a prosthetic heart valve) previously deployed inside a heart; and c) at least one flexible elongated tensioning member secured to the first anchor and to the second anchor thus substantially defining a distance separating the first anchor and the second anchor when the tensioning member is taut. In some embodiments, the second anchor is configured for deployment at least partially inside the left atrium of a heart. In some embodiments, the second anchor is configured to contact the aortic-mitral curtain portion of a mitral valve annulus. In some embodiments, the second anchor is configured for deployment at least partially inside the transverse pericardial sinus of a heart.

In some embodiments, the tensioning member is filamentous.

In some embodiments, the tensioning member is configured to slidingly pass through heart tissue.

In some embodiments, at least part of the first anchor is expandable, for example comprises an expandable wire mesh.

In some embodiments, the first anchor is configured for deployment at least partially outside of a heart. In some embodiments, the first anchor is configured for deployment substantially entirely outside of a heart.

In some embodiments, the first anchor comprises a single assembly including a contact face configured for contacting a surface of an external wall of a left ventricle of a heart.

In some embodiments, the first anchor comprises at least two discrete assemblies, each assembly including a contact face configured for contacting a surface of an external wall of a left ventricle of a heart, the first anchor configured to be deployed so that a contact face of each assembly contacts a different portion of a surface of an external wall of a left ventricle of a heart.

In some embodiments, the contact faces of at least one (and in some embodiments all) the assemblies of a first anchor of a device have a surface area of at least about 4 $cm^2$ and even at least about 6 $cm^2$. In some embodiments, the contact faces of at least one (and in some embodiments all) the assemblies of a first anchor of a device have an area of no more than about 25 $cm^2$ and even no more than about 15 $cm^2$.

In some embodiments, at least one contact face is concave. In some embodiments, at least one assembly of a first anchor comprises a plate curved so that the contact face is concave.

In some embodiments, when deployed a first anchor substantially maintains a shape to support the surface of a heart which is being contacted and distributing pressure over a greater surface area. In some such embodiments, an assembly of a first anchor is substantially rigid or, alternatively, elastic and slightly flexible.

In some embodiments, at least one assembly of a first anchor includes a pliant layer associated with the contact face, e.g., a layer of felt, sponge, fabric or tissue such as heterologous or homologous serous tissue. In some embodiments, the second anchor comprises a single assembly.

In some embodiments, at least part of the second anchor is expandable, for example comprises an expandable wire mesh.

In some embodiments, the device comprises a single tensioning member.

In some embodiments, the device comprises at least two tensioning members.

In some embodiments, the first anchor is configured to allow at least two tensioning members to be secured thereto at substantially the same location.

In some embodiments, the first anchor is configured to allow at least two tensioning members to be secured thereto at substantially different locations.

In some embodiments, the second anchor is configured to allow at least two tensioning members to be secured thereto at substantially the same location.

In some embodiments, the second anchor is configured to allow at least two tensioning members to be secured thereto at substantially different locations.

In some embodiments, a tensioning member is fixedly securable to the first anchor.

In some embodiments, the securing of a tensioning member to the first anchor comprises a portion of the tensioning member encircling a portion of the first anchor.

In some embodiments, the securing of a tensioning member to the first anchor comprises a portion of the tensioning member passing through a portion of the first anchor.

In some embodiments, the securing of a tensioning member to the second anchor comprises a portion of the tensioning member encircling a portion of the second anchor.

In some embodiments, the securing of a tensioning member to the second anchor comprises a portion of the tensioning member passing through a portion of the second anchor.

In some embodiments, a tensioning member and the first anchor are configured so that the tensioning member is reversibly securable to the first anchor when the device is deployed in a heart.

In some embodiments, a tensioning member and the second anchor are configured so that the tensioning member is reversibly securable to the second anchor when the device is deployed in a heart.

In some embodiments, a distance defined by a tensioning member is adjustable. In some embodiments, the device is configured so that a distance defined by a tensioning member is adjustable when the device is deployed in a heart.

In some embodiments, the distance defined by a tensioning member is adjustable by changing the location of a tensioning member through which the tensioning member is secured to the first anchor. In some embodiments, the device is configured so that the distance is adjustable by engaging the first anchor and/or the tensioning member (in embodiments near the first anchor). In some embodiments, the device is configured so that the distance defined by a tensioning member is adjustable when the device is deployed in a heart. In some embodiments, the device is configured so that the distance is adjustable from the direction of the apex of the heart.

In some embodiments, the distance is adjustable by changing the location of a tensioning member through which the tensioning member is secured to the second anchor. In some embodiments, the device is configured so that the distance defined by a tensioning member is adjustable by engaging the second anchor and/or the tensioning member (in embodiments near the second anchor). In some embodiments, the device is configured so that the distance defined by a tensioning member is adjustable when the device is deployed in a heart. In some embodiments, the device is configured so that the distance is adjustable from the transverse pericardial sinus.

In some embodiments, a device of the present invention is not provided fully assembled, but rather is assembled, at least partially, from separate components during deployment. Thus, according to an aspect of some embodiments of the present invention there is provided a kit for assembling a device substantially as discussed above for applying pressure to at least a portion of a mammalian heart. In some embodiments, a kit of the present invention comprises a) a first anchor configured for contacting a surface of an external wall of a left ventricle of a heart. In some embodiments, the first anchor is substantially as described above. In some embodiments a kit further comprises b) a second anchor configured for deployment in proximity to the aortic side of a mitral valve annulus of a heart. In some embodiments a kit further comprises b) a second anchor configured for deployment in proximity of a mitral valve annulus of a heart by engaging an implantable prosthesis previously deployed inside a heart. In some embodiments, the second anchor is substantially as described above.

In some embodiments, a kit of the present invention comprises at least one tensioning member configured to be secured to the first anchor and to the second anchor, thereby substantially defining a distance separating the first anchor and the second anchor when the tensioning member is taut. In some embodiments, the at least one tensioning member is substantially as described above. In some embodiments, a tensioning member provided with a kit is cuttable and, when cut, constitutes at least two separate tensioning members, each configured to be secured to the first anchor and to the second anchor. For example, in some embodiments, a tensioning member is provided as a spool of suture material or a long piece of suture material.

In some embodiments, at least one component of a device of the present invention are configured for minimally invasive deployment, for example a delivery catheter or a transapical probe.

In some embodiments, at least one component from amongst the first anchor and the second anchor is configured to fit inside a minimally-invasive delivery device. In some embodiments, the at least one component is packed inside such a minimally invasive delivery device.

In some embodiments, both the first anchor and the second anchor are configured for packing in a minimally-invasive delivery device. In some embodiments, both the first anchor and the second anchor are packed inside such a minimally invasive delivery device.

In some embodiments, the minimally-invasive delivery device is a delivery catheter.

In some embodiments, the minimally-invasive delivery device is a transapical probe.

In some embodiments, at least some components of a device are provided held within a transapical probe, configured to penetrate at or near the apex of a heart (and in some cases near the base of the papillary muscles), and to deploy the held components therein. For example, in some embodiments, a second anchor and a tensioning member, substantially as described above, are provided held inside a transapical probe. For example, in some embodiments, a first anchor, a second anchor and a tensioning member, substantially as described above, are provided held inside a transapical probe.

In some embodiments, at least some components of a device are provided held within a deployment catheter, configured to enter a heart and to deploy the held components therein. For example, in some embodiments, a first anchor and a tensioning member, substantially as described above, are provided held inside a deployment catheter. For example, in some embodiments, a first anchor, a second anchor and a tensioning member, substantially as described above, are provided held inside a deployment catheter.

According to an aspect of some embodiments of the present invention there is provided a coronary sinus ring apparatus, including an elongated body for deployment in a coronary sinus, an aperture in a long side of the body, at least a partial lumen extending from one end of the elongated body to at least the aperture, and a guide within the elongated body positioned and shaped to guide an element inserted along the lumen to the aperture.

According to some embodiments of the invention at least some of the elongated body comprises shape memory material.

According to some embodiments of the invention the shape memory material is a temperature-induced shape memory material.

According to some embodiments of the invention a transition temperature at which the shape memory material changes to its memorized shape is such that the shape memory material changes to its memorized shape at an intended recipient's body temperature.

According to some embodiments of the invention a transition temperature at which the shape memory material changes to its memorized shape is higher than an intended implant recipient's body temperature, such that the shape memory material changes to its memorized shape upon being heated to a temperature higher than the intended implant recipient's body temperature.

According to some embodiments of the invention the elongated body is configured to assume a substantially curved shape, for reshaping a mitral valve to a desired mitral valve annulus shape.

According to some embodiments of the invention the elongated body is configured to reshape the coronary sinus.

According to some embodiments of the invention further including a plurality of apertures.

According to some embodiments of the invention further including a multi-lumen catheter, wherein at least a plurality of the lumens includes an element for insertion along the lumen to at least a plurality of apertures.

According to some embodiments of the invention the aperture has a diameter of at least 1 mm.

According to some embodiments of the invention the guide is fixed.

According to some embodiments of the invention fluid flow through the body to an opposite end of the body is substantially blocked.

According to some embodiments of the invention a portion of the body extending past the guide is substantially solid and has a cross-section of at least 80% of a cross-sectional area of the body.

According to some embodiments of the invention including a guidewire channel extending past the guide and leading into the partial lumen.

According to some embodiments of the invention the guidewire channel is positioned relative to the guide and the partial lumen in a manner which impedes insertion of a guidewire through the partial lumen and into the guidewire channel.

According to some embodiments of the invention the channel is substantially continuous with a wall of the partial lumen.

According to some embodiments of the invention, including a guidewire with an at least partially pre-bent tip. According to some embodiments of the invention, including a guidewire with an S-shaped tip. According to some embodiments of the invention, including a guidewire with a J-Tip.

According to some embodiments of the invention, including a funnel-like wire guide at an entrance to the partial lumen.

According to some embodiments of the invention the body has a minimal cross-sectional diameter of less than 15 mm, such that the coronary sinus would not be blocked by the apparatus.

According to some embodiments of the invention, the body is long enough and stiff enough to modify a shape of a mitral valve annulus.

According to some embodiments of the invention, adapted for permanent implantation in a coronary sinus.

According to some embodiments of the invention, including a catheter adapted to fit through the aperture and including a tip for penetrating cardiac muscle tissue.

According to an aspect of some embodiments of the present invention there is provided a method of puncturing a coronary sinus wall, including placing a coronary sinus ring in the coronary sinus, inserting a puncturing device guided by the coronary sinus ring up to a puncturing device guide, having the puncturing device guide aim the puncturing device against the coronary sinus wall, and using the puncturing device to puncture the coronary sinus wall.

According to some embodiments of the invention placing a coronary sinus ring comprises placing a coronary sinus ring in which at least some of the coronary sinus ring comprises shape memory material.

Some embodiments of the invention further comprise reshaping the coronary sinus by leaving the coronary sinus ring in the coronary sinus.

According to an aspect of some embodiments of the present invention there is provided apparatus for treating a heart, including a delivery tube sized for and adapted for insertion into a body, a sharp tip adapted to be pushed through cardiac muscle, an elongate tensioning element, and a foldable anchor adapted to couple the elongate tension element to cardiac muscle tissue, wherein the delivery tube encloses one or both of the elongate tensioning element and the foldable anchor.

According to some embodiments of the invention at least some of the elongate tensioning element comprises shape memory material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more" unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

BRIEF DESCRIPTION OF THE FIGURES

Some embodiments of the invention are herein described, by way of example only, with reference to the accompanying Figures. With specific reference now to the Figures in detail, it is stressed that the particulars shown are by way of example and for purposes of illustrative discussion of some embodiments of the invention for providing a useful and readily understood description of the principles and conceptual aspects of some embodiments of the invention. The description, taken with the Figures, may make apparent to those skilled in the art how embodiments of the invention may be practiced.

In the Figures:

FIGS. 7A-7I depict an embodiment of a device configured for minimally invasive transapical deployment and deployment thereof;

FIGS. 9A-9G depict an embodiment of a device configured for trans catheter deployment and deployment thereof;

FIGS. 17A-17C illustrate a Coronary Sinus ring, in accordance with an alternative exemplary embodiment of the invention, at various stages of use thereof.

DESCRIPTION OF EXEMPLARY EMBODIMENTS OF THE INVENTION

Figure 1:
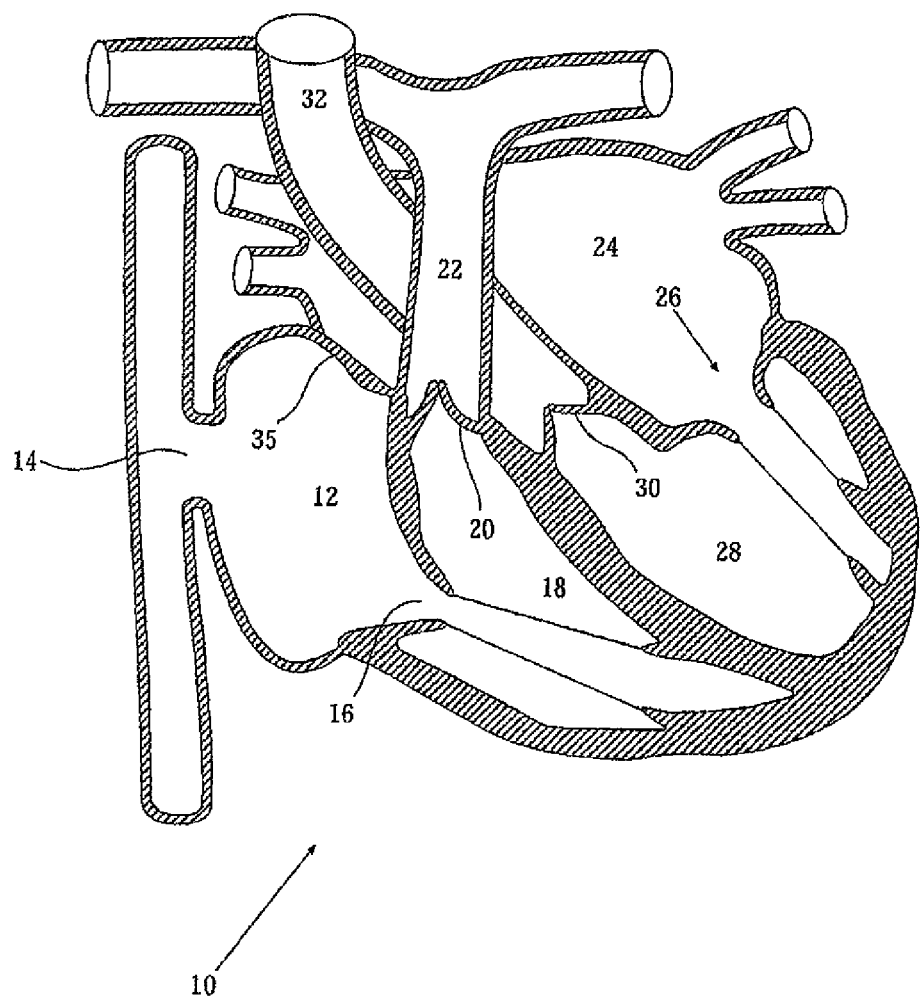
FIG. 1 (prior art) is a schematic depiction of a healthy heart in cross section.
Figure 2B:
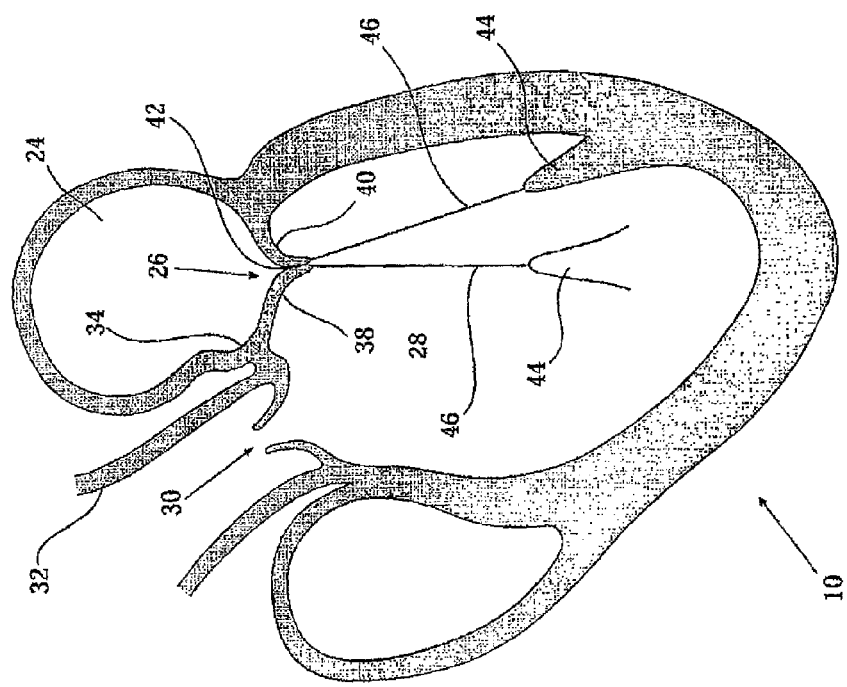
FIGS. 2A and 2B (prior art) depict a mitral valve of a healthy heart.
Figure 2A:
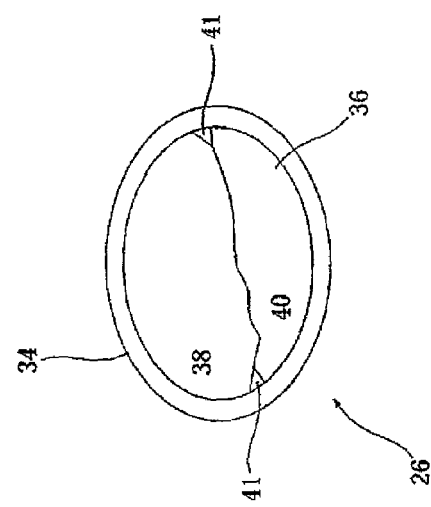
Figure 3B:
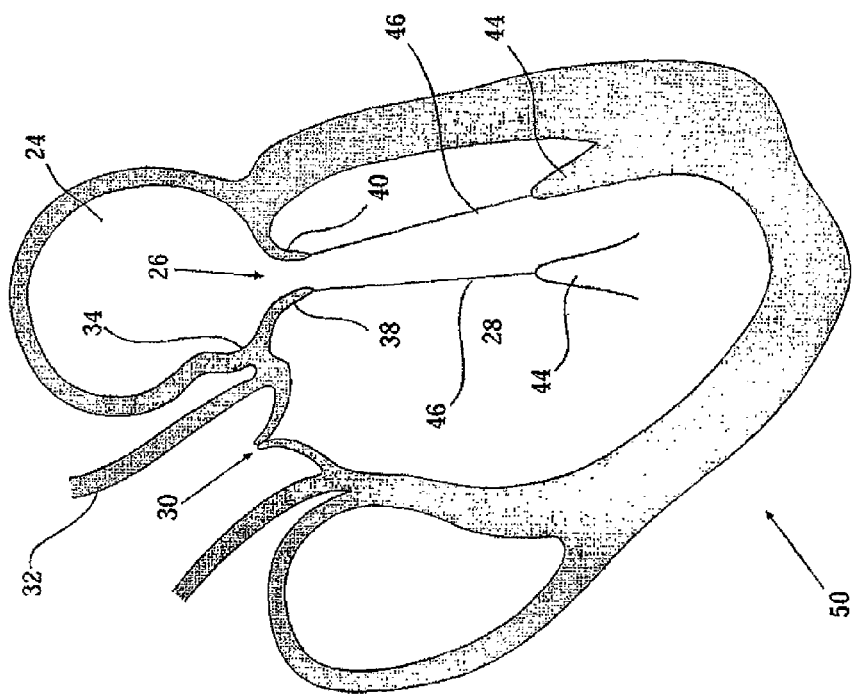
FIGS. 3A and 3B (prior art) depict a mitral valve of a heart suffering from ischemic mitral regurgitation related to incomplete coaptation of the leaflets of the mitral valve.
Figure 3A:
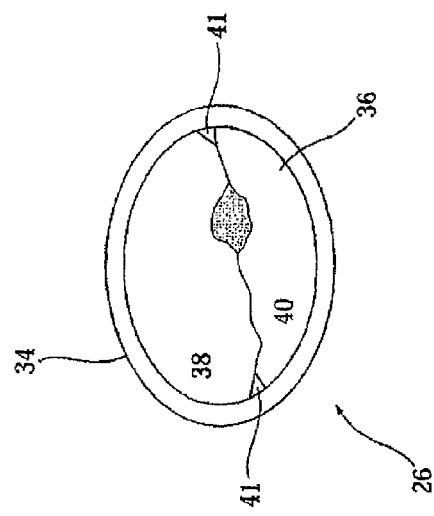

The present invention, in some embodiments thereof, relates to methods, devices and kits useful for applying forces to and/or limit movement of portions of a mammalian heart.

In some embodiments of the present invention, an implantable device comprising at least one flexible elongated tensioning member connecting between two anchors is deployed in the heart. In some embodiments, the first anchor is deployed on the outer surface of the left ventricle and the second anchor is deployed in proximity of the mitral valve annulus so that the tensioning member passes through the left ventricle. In such a way, the tensioning member substantially defines a distance separating the first anchor and the second anchor when the tensioning member is taut so that the first anchor and the second anchor each apply pressure to a portion of the heart.

Depending on the desired effect, the second anchor and/or elongate tensioning element may be provided at various sides of the mitral valve. As noted below, multiple anchors and/or cables may be provided at different points along the annulus of the mitral valve, and multiple anchors and/or cable may be provided at different points along the coronary sinus.

The first anchor may be located, for example, at middle of the posterior mitral annulus and/or in between the two trigones, depending on the desired effect on the heart.

In some embodiments of the present invention, the second anchor is configured for deployment in proximity of a mitral valve annulus by engaging an implantable prosthesis (e.g., an annuloplasty ring, a prosthetic heart valve) previously and/or concurrently deployed inside a heart. Some such embodiments, especially when configured for minimally invasive deployment, are potentially useful for "retrofitting" a heart that has been previously been treated by deployment of a prosthetic heart valve or annuloplasty ring, possibly with a relatively reduced level of trauma to the heart. For example, in some cases due to continued remodeling of the heart, the leaflets of an annuloplasty ring-supported mitral valve exhibit insufficient coaptation. Some embodiments of the present invention allow for improvement of the leaflet coaptation by deploying a device including a second anchor that engages the previously deployed annuloplasty ring without necessitating a more traumatic intervention such as replacement of the annuloplasty ring and/or Mitral valve.

In some embodiments of the present invention, the second anchor is configured for deployment in proximity to the aortic side of the mitral valve annulus, for example in proximity of the midseptal fibrous annulus. Some such embodiments take advantage of the relative toughness and tenacity of the fibrous parts of the heart to support the second anchor and to distribute pressures in the heart with comparatively little trauma. In some embodiments, the first and/or second anchor are positioned and/or configured (e.g., size of contact area) to engage other fibrous parts of the heart.

In some embodiments of the present invention, an implantable device comprising more than one flexible elongated tensioning member connecting between two anchors is deployed in the heart. In some such embodiments, different tensioning members each independently define a distance between a first anchor and a second anchor when taut.

In some embodiments, a plurality (e.g., 2, 3, 4, or more) of implantable devices are used in a same heart, optionally sharing an anchor. Optionally, devices are added over time, as needed. Optionally, previously implanted devices are removed and/or tightened and/or loosened, as needed.

In some embodiments, the force and/or movement limitation applied to the heart by the implantable device has at least one beneficial effect. By beneficial effect is meant that the device has an effect such as curing a condition, treating a condition, preventing a condition, treating symptoms of a condition, curing symptoms of a condition, ameliorating symptoms of a condition, treating effects of a condition, ameliorating effects of a condition, and preventing results of a condition. For example, in some embodiments, the applied pressure changes the shape of the cardiac walls and/or of the left atrium.

In some embodiments, the device is implanted in other chambers of the heart and/or across two or more heart chambers. Optionally, such a device serves to have a beneficial effect (e.g., to positively remodel) other chambers and/or valves of the heart.

For example, in some embodiments, the force applied on the heart by the anchors supports sagging portions of the cardiac walls. For example, in some embodiments, the device relieves and/or redistributes pressure inside the heart. In some embodiments, the device ameliorates and even reverses at least some of the effects of cardiac remodeling.

For example, in some embodiments, the pressure applied on the outer surface of the left ventricle by the first anchor pushes the outer wall of the left ventricle upwards, bringing the papillary muscles and the chordae towards the mitral valve, improving coaptation of the mitral valve leaflets.

For example, in some embodiments, the pressure applied on the outer surface of the left ventricle supports a portion of the heart wall that is sagging or weakened, for example due to cardiac remodeling, muscle death and/or cardiomyopathy.

In an exemplary embodiment of the invention, the device is provided using a minimally invasive approach. Optionally, the heart is not stopped during such treatment. In an exemplary embodiment of the invention, the approach is from outside the heart (e.g., keyhole surgery), for example using a trans-apical (the heart, however, need not be penetrated specifically at the apex). Optionally or alternatively, the approach is trans-septal using a catheter. Optionally or alternatively, the approach is via a coronary sinus into the left atrium and/or left ventricle.

In an exemplary embodiment of the invention, the approach is via the coronary sinus into the left atrium and/or left ventricle, and a coronary sinus ring is left within the coronary sinus, optionally exerting some force on the coronary sinus, thereby achieving cardiac remodeling.

In some embodiments of the invention the Coronary Sinus (CS) ring functions as a guide for a puncturing device, for example a tip of a guide wire, into the coronary sinus wall. The CS ring optionally also functions as an anchor for a tensioning member, thereby providing both guiding functionality and anchoring functionality.

In an exemplary embodiment of the invention the CS ring includes one or more apertures, or holes, so that, when the CS ring is in position in the coronary sinus, the apertures are positioned at locations through which punctures are to be made through the coronary sinus wall and into the left atrium and/or left ventricle. The apertures function as preset aiming apertures.

In some embodiments of the invention the apertures are designed to catch the puncturing device and to aim it.

In some embodiments of the invention the CS ring includes guiding surfaces to catch the puncturing device and to aim it.

In some embodiments of the invention the apertures are initially sealed, by way of a non-limiting example, with a membrane.

In an exemplary embodiment of the invention the guide and the one or more apertures are designed so that a tip of a wire and/or tips of wires for puncturing the coronary sinus are guided into the holes. Optionally, the shape of the guide assists guiding the tip into the hole.

Thus, some embodiments of the present invention are useful for treating a condition related to cardiac remodeling, for example ischemic mitral regurgitation.

The principles and uses of the teachings of some embodiments of the present invention may be better understood with reference to the accompanying description and the Figures. In the Figures, like reference numerals refer to like and/or similar parts throughout.

Before explaining at least one embodiment in detail, it is to be understood that the invention is not necessarily limited in its application to the details of construction and the arrangement of the components and/or methods set forth in the following description and/or illustrated in the figures. The invention can be implemented with other embodiments or of being practiced or carried out in various ways.

Some embodiments of a device of the present invention are devices that, when properly implanted in the body of a mammal, apply force to and/or limit motion of at least a portion of a heart, and as such in some embodiments are useful for implementing the method of the present invention.

Some embodiments of a device of the present invention comprise a) a first anchor configured for contacting a surface of an external wall of a left ventricle of a heart; b) a second anchor configured for deployment in proximity to a mitral valve annulus of a heart; and c) at least one elongated tensioning member secured to the first anchor and to the second anchor thus substantially defining a distance separating the first anchor and the second anchor when the tensioning member is taut. It should be noted that the order of application of the anchors may be different in different embodiments of the invention.

In some embodiments of the present invention, the second anchor is configured for deployment in proximity of a mitral valve annulus by engaging an implantable prosthesis (e.g., an annuloplasty ring, a prosthetic heart valve) previously deployed inside a heart. Optionally, the prosthesis includes a rod like element, such as the body of the ring or an annulus of the valve. Optionally or alternatively, the prosthesis includes an aperture, slot and/or other structure adapted to cooperate with an anchoring part of the implantable device.

In some embodiments of the present invention, the second anchor is configured for deployment in proximity to the aortic side of the mitral valve annulus, for example in proximity of the midseptal fibrous annulus.

Tensioning Member

In some embodiments, a tensioning member is a flexible elongated component. In some embodiments, a tensioning member is substantially axially unstretchable or substantially resistant to axial stretching. In some embodiments, a tensioning member is configured to slidingly pass through heart tissue.

Optionally, the tensioning element is coated or formed to not adhere to tissue. This may assist in later removal thereof.

In an exemplary embodiment of the invention, the tensioning element is elastic, for example, designed to elongate under tension. Optionally, the elastic properties of such a member are selected to match a desired dynamic effect on the heart, for example, allowing the heart to dilate during exercise and/or assist systole by recoiling (e.g., assisting the heart to contract using elastic energy stored in the member during diastole). In an exemplary embodiment of the invention, the member is resilient and can extend during diastole, possibly assisting refilling during diastole. In an exemplary embodiment of the invention, assistance to contracting and/or other functioning of the heart is at least of an order of 3%, 5%, 10%, 20%, 30% or intermediate percentage increase in cardiac output.

In an exemplary embodiment of the invention, the member is selected and located so as to increase pre-stretching of some parts of the heart, which are optionally healthy, thereby increasing a contraction force thereof during systole.

In some embodiments, one or more tensioning members are secured to the first anchor and to the second anchor, each tensioning member defining a distance separating the first anchor from the second anchor when the tensioning member is taut. When a heart is in a state forcing the first anchor and second anchor apart to the distance defined by a tensioning member, the tensioning member is stretched taut so that the anchors to apply pressure to the heart.

Optionally, the tensioning member (and/or an attachment thereof to the anchors) are designed with a tension limit, above which the member fails in a known manner, for example, tearing at a previously weakened point or elongating by a known amount. Optionally, the tension limit is selected to avoid physiological damage to the heart.

Generally, a tensioning member is configured to pass through heart tissue. For example, in some embodiments, a tensioning member passes through the external wall of a left ventricle (e.g., in proximity of the cardiac apex) when deployed, especially the portion of a tensioning member near the first anchor. For example, in some embodiments, a tensioning member passes through tissue in the vicinity of a mitral valve annulus (for example when passing from the left ventricle to the transverse pericardial sinus) when deployed, especially the portion of a tensioning member near the second anchor.

In some embodiments, a device of the present invention comprises a single tensioning member secured to the first anchor and to the second anchor.

In some embodiments, a device of the present invention comprises at least two tensioning members. In some embodiments, a first anchor is configured to allow at least two separate tensioning members to be secured thereto, each tensioning member from a different orientation or direction. In some embodiments, a first anchor is configured to allow two tensioning members to be secured to substantially the same location of the first anchor. In some embodiments, a first anchor is configured to allow two tensioning members to be secured to substantially different locations of the first anchor. In some embodiments, a second anchor is configured to allow at least two separate tensioning members to be secured thereto, each tensioning member from a different orientation or direction. In some embodiments, a second anchor is configured to allow two tensioning members to be secured to substantially the same location of the second anchor. In some embodiments, a second anchor is configured to allow two tensioning members to be secured to substantially different locations of the second anchor.

In some embodiments, a tensioning member is filamentous. By filamentous is meant a tensioning member comprising a component such as a fiber, a filament, a ribbon, a cord, a rope, a strand, a thread, a cable, a wire or yarn.

Optionally, the member is formed as a ribbon or is otherwise configured to not flex equally easily in different directions.

In an exemplary embodiment of the invention, the member is made somewhat resilient. Optionally, the resilience prevents the member form looping and/or otherwise engaging parts of the heart when the heart contracts.

In some embodiments, a tensioning member comprises a filament or the like made of a synthetic polymer, a natural polymer and/or of an inorganic material. In some embodiments, such a filament or the like is coated, for example to reduce thrombogenicity, to increase biostability, reduce friction with cardiac tissue and/or to increase biocompatibility.

Inorganic materials that in some embodiments are suitable for implementing a tensioning member of the present invention include metal and metal alloy filaments, such as of silver, gold, titanium or stainless steel.

Natural polymers that in some embodiments are suitable for implementing a tensioning member of the present invention include cotton, linen and silk.

Synthetic polymers that in some embodiments are suitable for implementing a tensioning member of the present invention include fluorinated hydrocarbons (e.g., polytetrafluoroethylene), polyesters (e.g., Dacron® (E.I. du Pont de Nemours and Company, Wilmington, Del., USA)), polyethylenes (e.g., Ultra-High Molecular Weight polyesters such as Dyneema® (DSM, Heerlen, the Netherlands), Spectra® (Honeywell, Morisstown, N.J., USA)) and polyamides (e.g., Nylons, such as Nylon 6-6, aromatic polyamides such as Kevlar® (E.I. du Pont de Nemours and Company, Wilmington, Del., USA)).

Suitable tensioning members, for example, include sutures of sufficient strength, for example 3-0 Prolene non-resorbable sutures.

In some alternative embodiments of the invention at least some of the tensioning member optionally includes shape memory material. Shape memory material is a material which, in a first state, is given a certain first shape, which the material "remembers". Later, the material can be bent or stretched and the material holds the bent or stretched shapes until induced to return to its first, desired, "remembered" shape. One example way of inducing the material to return to its remembered shape is by heating. Upon heating, the shape memory material changes to its remembered shape. When the shape memory material cools again it will remain in the desired, remembered shape.

The tensioning member is optionally longer when inserted into a body, and shortens when induced to remember a desired shape.

The tensioning member is optionally shaped as a wire, which is longer when inserted into a body, and shortens when induced to change shape to its desired shape.

The tensioning member is optionally shaped at least partly as a spring, and/or as a zigzag shaped wire or strip, which is longer when inserted into a body, and shortens when induced to change shape to its desired shape.

Shape memory materials include metal alloys, and polymers.

Inducing a shape memory material to return to a remembered desired shape is optionally performed according to a type of the shape memory material. Some shape memory materials are optionally induced by heating, other shape memory materials change shape under strong magnetic fields. In some embodiments of the invention, when magnetic materials are used, the magnetic materials are coated, as some magnetic materials may be harmful to a living body.

In some embodiments of the invention a temperature-induced shape memory material is used, such that the shape memory material returns to its remembered shape at a temperature close to a body temperature of an intended recipient. In some embodiments, in case of use in humans, the transition temperature of the material is slightly lower than body temperature, for example 33 degrees Celsius. In some embodiments, in case of use in humans, the transition temperature of the material is at body temperature, for example 37 degrees Celsius. In some embodiments, in case of use in humans, the transition temperature of the material is slightly higher than body temperature, for example 39 degrees Celsius. The tensioning member is optionally kept cold before inserting into the recipient's body, and after being in the body for some time, heats to body temperature and changes shape. In some embodiments the changed shape is optionally shorter than the unchanged shape, and the tensioning member exerts tension when it heats to body temperature. In some embodiments the changed shape is optionally more rigid than the unchanged shape, and the tensioning member exerts tension and reshapes the heart.

The shape memory material is optionally such that after regaining its memorized shape, the material keeps its shape over temperature ranges which are natural for the recipient's body. In some embodiments, in case of use in humans, the material keeps its shape over a range of 30 degrees Celsius to 41 degrees Celsius. In some embodiments, in case of use in humans, the material keeps its shape over a still larger range of range of 28 degrees Celsius to 43 degrees Celsius.

In some embodiments of the invention a temperature-induced shape memory material is used, such that the shape memory material returns to its remembered shape at a temperature which is higher than the body temperature of an intended recipient. The tensioning member is inserted into the recipient's body, after which the tensioning member is heated to its transition temperature, and the temperature-induced shape memory material changes shape.

In some embodiments of the invention the heating is performed by electrically isolating the shape memory material and passing a current through the material. In some embodiments of the invention the shape memory material is coated with an isolating material. In some embodiments of the invention the heating is performed by an electrically isolated electrical heating device held next to the shape memory material.

In some embodiments of the invention a high frequency electrical current is used, at a high enough frequency so it cannot cause inadvertent cardiac activation or fibrillation.

Tensioning members 58, 58*a*, and 58*b*, are mentioned within the present document with reference to different embodiments of the invention, the embodiments described with reference to FIGS. 4C, 6A, 6B, 7A, 7B, 8D, 8E, 9B, 9F, and 9G. In some of the above-mentioned embodiments, the tensioning member is suitable for using shape memory material.

In an exemplary embodiment of the invention, the member is made biodegradable and/or includes a biodegradable portion that dissipates over time in the body and/or blood, so that the function of the device is stopped. Optionally, such degradation is designed to occurs after 1 week, 1 month, 5 months and/or other, intermediate or greater periods of time, depending, for example, on a desired effect and/or duration thereof. Optionally, the member includes multiple filaments, some of which degrade and some which do not. Optionally, the non-degrading filaments allow a greater degree of motion between the anchors and/or do not impose limits on the heart, but maintain the anchors in place. Optionally, such an effect of changing of member length over time is provided by folding over the tensioning element and maintaining the fold with a biodegrading adhesive, element (e.g., band) and/or sleeve. Various biodegrading materials, including plastics are known in the art and may be used.

As used herein, "dissipate" is used to describe a state in which an implant structure is compromised, for example, due to dissolving, sorption, attack by blood components and/or chemical change, which may cause, for example, parts of the structure to be carried away, fall off, dissolve and/or weaken. After time, the structure may disappear completely.

First (Apical) Anchor

In some embodiments, a first anchor of a device of the present invention is configured for contacting a surface of an external wall of a left ventricle of a heart, possibly, but not necessarily the apex. In some embodiments, a first anchor of the present invention is termed an "apical anchor" due to the deployment of the first anchor at or near a cardiac apex, for example in the area of the external wall of the left ventricle across from the base of the papillary muscles, or at an area of left ventricle which is weakened, diseased and/or bulges.

In some embodiments, a first anchor is configured to be at least partially, and in some embodiments entirely, deployed outside of a heart. When deployed, a corresponding tensioning member secured to the first anchor penetrates through the heart tissue, in some embodiments through the wall of the left ventricle.

In some embodiments, a first anchor comprises only a single assembly including a contact face configured for contacting a surface of an external wall of a left ventricle of a heart. In an exemplary embodiment of the invention, the anchor only contacts the wall and is not configured to engage the wall (e.g., is smooth and/or has no sutures). Optionally, the anchor is coated with materials that enhance fibrosis and/or otherwise enhance engagement of the wall by the anchor. Optionally, an adhesive is provided. Such treatment and/or design may be applied to other anchors as well.

In some embodiments, a first anchor comprises at least two assemblies, each assembly including a contact face configured for contacting a surface of an external wall of a left ventricle of a heart, the first anchor being configured to be deployed so that a contact face of each assembly contacts a different portion of a surface of an external wall of a left ventricle of a heart. In addition to dispersing the pressure applied to the heart, such embodiments allow two or more tensioning members to be oriented with substantially different orientations and/or directions. In some embodiments, a first anchor comprises at least two discrete assemblies.

In some embodiments, one, more than one or all of the contact faces of the one or more assemblies of a first anchor have a surface area that is at least about 4 $cm^2$ and even at least about 6 $cm^2$. In some embodiments, the contact faces of one, more than one, or all of the assemblies of a first anchor have an area of no more than about 25 $cm^2$ and even no more than about 15 $cm^2$. In an exemplary embodiment of the invention, the contact area and/or force distributing elements in the anchor (e.g., metallic ribs) are designs to support an otherwise ballooning section of the heart.

In some embodiments, the contact face has a rounded shape, e.g., round, oval, elliptical, oblate. For example, in some embodiments, a contact face has an oval or elliptical shape that has a large dimension of between 2 cm and 5 cm and a small dimension of between 1.5 cm and 3 cm.

In some embodiments, at least one contact face is concave so as to follow the curvature of the surface of the left ventricle. In some embodiments, at least one assembly of a first anchor comprises a plate curved so that the contact face is concave. In other embodiments, the contact face is flat and/or has another shape which is not simply concave, for example, including ridges or other protrusions.

In some embodiments, a first anchor substantially maintains a shape to support the contacted surface of a heart and distributes pressure over a greater surface area of the heart. In some such embodiments, an assembly of a first anchor is substantially rigid or, alternatively, is elastic and slightly flexible. Exemplary materials from which a first anchor is made include a plastic (e.g., PMMA), a metal (e.g., Nitinol), or a mesh.

In an exemplary embodiment of the invention, the anchor includes a plurality (e.g., 2, 3, 4, 5, or more) of members designed to contact the heart, for example, fingers, for example, the anchor being formed as a plurality of members that extend away form a common center (e.g., to which the tensioning element is attached. Optionally, an outer ring interconnects at least some of the members.

In an exemplary embodiment of the invention, the anchor is formed in the shape of a ring.

In some embodiments, at least a portion of a first anchor is expandable (e.g., including unfoldable). In other embodiments the anchor is rigid.

In some embodiments, a first anchor is configured for minimally-invasive delivery, for example with the help of a delivery catheter (e.g., trans-septal and/or via coronary sinus) or a transapical probe. For example, in some embodiments, a first anchor is configured to fit inside a delivery device (for example is expandable, for example comprises an expandable wire mesh). In some embodiments, at least a portion of a first anchor (in embodiments an entire first anchor) is provided packed in a delivery device (for example, an expandable first anchor packed while in a non-expanded state) such as a delivery catheter or a transapical probe. Some such embodiments are discussed hereinbelow.

In some embodiments, at least one assembly of a first anchor includes a pliant layer associated with the contact face, e.g., a layer of felt, sponge, fabric or tissue such as heterologous or homologous serous tissue. In some embodiments, a pliant layer reduces pressure trauma on the surface of the heart and more evenly distributes the pressure over the surface of the heart.

In some embodiments, a first anchor comprises one or more assemblies that are similar in construction (although in some embodiments different in shape and/or dimensions) to pads such as used in implementing the Coapsys® device commercially available from Myocor, Inc. (Maple Grove, Minn., USA).

In an exemplary embodiment of the invention, the anchor attachment to the tensioning member and/or the anchor itself are flexible enough to provide some give to the implantable device, when in use. Optionally, the point of attachment is formed as a cone with its point towards the heart.

While, in an exemplary embodiment of the invention, the anchor lies outside the heart, this need not be the case. For example, in an exemplary embodiment of the invention, the anchor is designed to expand inside muscle tissue and/or is a helix which screws into muscle tissue. In another example, the anchor comprises two plates, one inside the heart and on outside the heart, on opposite sides of the cardiac wall, sandwiching the wall between them (e.g., using a design such as used for an Amplatzer® Septal Occluder device for sealing septal defects). This may allow the anchor to be fixed in place while separately attaching tensioning members and without suturing the anchor to the heat, thereby allowing removal thereof until the anchor is engaged by tissue.

Optionally, the anchor is desired to degrade after a time in the body, Optionally, a time substantially longer that required for tissue adhesion to the tensioning member and/or time for dissipation of the tensioning member.

In an exemplary embodiment of the invention, the anchor is large enough to constraining the expansion (and/or assist in contraction) of the left ventricle as a whole, for example, being a cup shaped anchor with a contact surface area of at least 10 cm$^2$, 20 cm$^2$, 30 cm$^2$, 40 cm$^2$ or intermediate areas. Optionally, the tensioning member is then used to maintain such a constraining element in place and optionally not to have a geometry limiting function. Alternatively, the geometry limiting functions of the anchor an the member and/or of the second anchor cooperate to have a desired effect.

Second (Mitral) Anchor

In some embodiments, a second anchor of a device of the present invention is configured for deployment in proximity to a mitral valve annulus of a heart. In some embodiments, a second anchor of the present invention is termed a "mitral anchor" due to the deployment of the second anchor near a mitral valve annulus. In some embodiments, a second anchor comprises a single assembly. In some embodiments, the second anchor is configured for deployment at least partially inside the left atrium of a heart. In other embodiments, the anchor is anchored outside the heart.

In some embodiments, a second anchor of a device of the present invention is configured for deployment as a CS ring, as described further below with reference to FIGS. 12A-E, 13A-13C, 14A-14C, 15A-15B, 16A-16B, and 17A-17C.

In some embodiments, a second anchor is configured for deployment in proximity to the aortic side of a mitral valve annulus of a heart, for example in proximity of a midseptal fibrous annulus. In some embodiments, when a device is deployed in a heart, a tensioning member secured to a second anchor enters the left ventricle from the area roughly between the aortic valve and the anterior leaflet side of the mitral valve, underneath or through the mitral valve annulus. In some embodiments, the second anchor is configured to rest against or otherwise contact the aortic mitral curtain portion of a mitral valve annulus. In some embodiments, the second anchor comprises a prosthesis device such as an annuloplasty ring or prosthetic heart valve.

In some embodiments, the second anchor is configured for deployment at least partially inside the transverse pericardial sinus of the heart. Such embodiments may be advantageous for one or more of a number of reasons. In some such embodiments at least some of the pressure applied by the second anchor to the heart is applied to a relatively tough outer surface of the heart, reducing trauma. In some such embodiments the pressure applied by the second anchor is applied to and distributed by the fibrous cardiac tissue (e.g., midseptal fibrous annulus) located between the aortic valve and the mitral valve, optionally due to anchoring at the location of the transverse pericardial sinus just over these fibrous tissues. In some such embodiments, placement of the second anchor primarily in the transverse pericardial sinus and thus outside of the cardiac chambers reduces the chance that a deployed device directly substantially changes the flow of blood inside the heart. In some such embodiments, the placement of the second anchor at least partially inside the transverse pericardial sinus avoids the application of substantial and/or direct pressure to the mitral valve annulus, allowing the mitral valve annulus to function normally (e.g., to contract during ventricular systole) without distortion.

In some such embodiments, the second anchor is substantially an elongated member optionally configured to fit inside the transverse pericardial sinus of a heart. In some embodiments, the second anchor has a length of between about 1 cm and about 6 cm (in some embodiments between about 1 cm and about 2 cm) and a width of between about 2 mm and about 5 mm (in some embodiments between about 2 mm and about 3 mm) so as to fit inside a transverse pericardial sinus. In some embodiments, a second anchor is axially flexible allowing the second anchor to conform and better fit inside the transverse pericardial sinus and to bend with the beating of the heart. In some embodiments, a second anchor is a substantially rigid rod (e.g., a straight or curved rod). In some embodiments, a second anchor is semi-rigid, for example, like the Physio® annuloplasty ring available from Edwards Life sciences (Irvine, Calif., USA).

In some embodiments, at least a portion of a second anchor is expandable.

In some embodiments, a second anchor is configured for minimally-invasive delivery, for example with the help of a delivery catheter or a transapical probe. For example, in some embodiments, a second anchor is configured to fit inside a delivery device (for example is expandable, for example comprises an expandable wire mesh or a folded rod). In some embodiments, at least a portion of a second anchor (in embodiments an entire second anchor) is provided packed in a delivery device (for example, an expandable second anchor packed while in a non-expanded state) such as a delivery catheter or a transapical probe. Some such embodiments are discussed hereinbelow.

In some embodiments, a second anchor is fashioned from materials such as known in the art of annuloplasty rings, for example nitinol, stainless steel shape memory materials, metals, synthetic biostable polymer, a natural polymer, an inorganic material, titanium, pyrolytic carbon, a plastic, a titanium mesh or polydimethylsiloxane.

In some embodiments, a biostable polymer from which a second anchor is fashioned comprises a material from the group including a polyolefin, polyethylene, a fluorinated hydrocarbon such as polytetrafluoroethylene (Teflon®), a polycarbonate synthetic, a polyurethane, a fluorinated polyolefin, a chlorinated polyolefin, a polyamide, an acrylate polymer, an acrylamide polymer, a vinyl polymer, a polyacetal, a polycarbonate, a polyether, an aromatic polyester, a polyether (ether ketone), a polysulfone, a silicone rubber (e.g., Silastic by Dow-Corning Corporation, Midland, Mich., USA), a thermoset material, or a polyester (ester imide, for example Dacron® by Invista, Wichita, Kans., USA) and/or combinations thereof.

In some embodiments, a second anchor is configured to allow a tensioning member secured thereto to pass through the second anchor. For example, in some embodiments, a second anchor is made of a piercable material, for example silicone rubber or felt. For example, in some embodiments, a second anchor is provided with holes, gaps or channels allowing passage of tensioning member therethrough, for example, a second anchor fashioned of a titanium mesh.

In some embodiments, a second anchor is configured to localize a tensioning member looped around and encircling the second anchor, thereby preventing slippage along the second anchor. In some embodiments, such configuration comprises, for example ridges, bumps, grooves and other like features on an outer surface of the second anchor.

In some embodiments, a second anchor is configured to engage an implantable prosthesis previously deployed in the heart. For example, in some embodiments, a second anchor is configured to engage an annuloplasty ring deployed in proximity of a mitral valve annulus in the usual way. For example, in some embodiments, a second anchor is configured to engage a prosthetic heart valve deployed in proximity of a mitral valve annulus in the usual way. Such embodiments are possibly useful by allowing implementation of the teachings of some embodiments of the present invention (especially minimally-invasive embodiments of the present invention) to subjects previously treated, for example with the deployment of an annuloplasty ring or prosthetic heart valve, where the results of the previous treatment are unsatisfactory, for example as a result of continued remodeling of the heart. In such embodiments, it is possible to secure the tensioning member or members to various locations of the implantable prosthesis, for example in proximity of the aortic side of the mitral valve but also not in proximity of the aortic side of the mitral valve.

In an exemplary embodiment of the invention, the second anchor is an annuloplasty ring. Optionally, such a ring is not separately attached to the heart, other than being held by the tensioning element. Optionally or alternatively, such a ring includes one or more spikes to engage cardiac tissue, at least when the ring tensioned by said tensioning member. Alternatively, the ring is sutured to cardiac tissue.

In an exemplary embodiment of the invention, the second anchor is located inside a coronary sinus. Optionally, the anchor is an annuloplasty ring located inside the coronary sinus. In an alternative embodiment, the anchor only has an anchoring function. In an alternative embodiment, the anchor only has an annuloplasty function.

In an exemplary embodiment of the invention, the second anchor is a hook adapted to hook an annuloplasty ring (or other prosthesis) inside the coronary sinus or inside the left atrium.

In general the designs of the anchors may depend on the desired use of the device. In one example, the device is anchored on both sides to free expanses of the heart (e.g., left ventricle side and right ventricle side) and the anchor is of the apical deign for both sides.

Optionally or alternatively, various features described above with reference to an apical anchor may be applied to a mitral anchor.

In an exemplary embodiment of the invention, one or both anchors and/or the tensioning member elute a pharmaceutical (e.g. vascular endothelial growth factors (VEGF)). Optionally, one or more radio-opaque markers are provided in the device, for example, to allow easy assessment of its location and/or integrity via x-ray imaging and/or echo (ultrasound) imaging (for which acoustic markers may be provided).

In some embodiments, a tensioning member and a first anchor are configured so that the tensioning member is fixedly securable to the first anchor. In some embodiments, a tensioning member and a second anchor are configured so that the tensioning member is fixedly securable to the second anchor.

In some embodiments, the securing of a tensioning member to a first anchor comprises a portion of the tensioning member encircling a portion of the first anchor. In some embodiments, the securing of a tensioning member to a second anchor comprises a portion of the tensioning member encircling a portion of the second anchor.

In some embodiments, the securing of a tensioning member to a first anchor comprises a portion of the tensioning member passing through a portion of the first anchor. In some embodiments, the securing of a tensioning member to a second anchor comprises a portion of the tensioning member passing through a portion of the second anchor.

In some embodiments, a tensioning member and the first anchor are configured so that the tensioning member is reversibly securable to the first anchor when deployed in a heart.

In some embodiments, a tensioning member and the second anchor are configured so that the tensioning member is reversibly securable to the second anchor when deployed in a heart.

In some embodiments, a distance defined by a tensioning member is adjustable. In some embodiments, the device is configured so that a distance defined by a tensioning member is adjustable when the device is deployed in a heart. In some embodiments, the adjustability is during deployment of the device. In some embodiments, the adjustability is after the device is deployed in a heart for some time, for example after at least one day. In some embodiments, the device is configured so that the distance is adjustable by engaging the first anchor and/or the second anchor and/or the tensioning member.

In an exemplary embodiment of the invention, the anchor and/or tensioning member include a thread and the adjusting is by rotation of one relative to the other.

In an exemplary embodiment of the invention, the anchor is locked to the tensioning element by a screw which is provided in the anchor and rotated to engage the tensioning element. Optionally or alternatively, the tensioning element is wrapped around a suitable projection of the anchor. Optionally or alternatively, the anchor is crimped on the tensioning element. Optionally or alternatively, the tensioning element includes one or more widened portions, for example, beads, which are engaged by an aperture in the anchor which is not wide enough for the widened part of the anchor to pass through. In one example, the anchor comprises an aperture in the form of two side by side and connected (e.g., by a slot) apertures, one wide enough for the tensioning element at any diameter thereof and one only wide enough for the narrowed sections of the tensioning element. Locking is optionally achieved by passing the tensioning element between the apertures.

In an exemplary embodiment of the invention, the tensioning member includes a plurality of projections axially distributed, which, together with one or more projections in an aperture of the anchor, define a ratcheting element, allowing one way retraction of the tensioning member through the anchor aperture.

In some embodiments, the distance defined by a tensioning member is adjustable by changing the location of a tensioning member through which the tensioning member is secured to the first anchor. In some embodiments, the device is configured so that the distance is adjustable by engaging the first anchor and/or the tensioning member (in embodiments near the first anchor). In some embodiments, the device is configured so that the distance defined by a tensioning member is adjustable when the device is deployed in a heart. In some embodiments, the device is configured so that the distance is adjustable from the direction of the cardiac apex.

In some embodiments, the distance is adjustable by changing the location of a tensioning member through which the tensioning member is secured to the second anchor. In some embodiments, the device is configured so that the distance defined by a tensioning member is adjustable by engaging the second anchor and/or the tensioning member (in embodiments near the second anchor). In some embodiments, the device is configured so that the distance defined by a tensioning member is adjustable when the device is deployed in a heart. In some embodiments, the device is configured so that the distance is adjustable from a transverse pericardial sinus.

Kits

In some embodiments, a device of the present invention is not provided fully assembled, but rather is provided at least partially disassembled in the form of a kit, in embodiments packaged in a sterility-preserving package. In such embodiments, the device is assembled during deployment in a heart. In other embodiments, the device is provided fully assembled and loaded within a minimally-invasive delivery tube such as a catheter or a trans-apical delivery system.

In some embodiments, a kit of the present invention comprises a first anchor configured for contacting a surface of an external wall of a left ventricle of a heart. In some embodiments, the first anchor is substantially as described above.

In some embodiments, a kit of the present invention comprises a second anchor configured for deployment in proximity of a mitral valve annulus of a heart. In some embodiments, the second anchor is substantially as described above.

In some embodiments, a kit of the present invention comprises at least one tensioning member configured to be secured to the first anchor and to the second anchor, thereby substantially defining a distance separating the first anchor and the second anchor when the tensioning member is taut. In some embodiments, the at least one tensioning member is substantially as described above. In some embodiments, a tensioning member provided with a kit is cuttable and, when cut, constitutes at least two separate tensioning members, each configured to be secured to the first anchor and to the second anchor. For example, in some embodiments, a tensioning member is provided as a spool of suture material or a long piece of suture material.

In some embodiments, a device of the present invention is provided with at least some components packed in a minimally-invasive delivery device, such as a transapical probe or a delivery catheter.

For example, as detailed hereinbelow in some embodiments a device of the present invention is provided with a first anchor and a tensioning member associated therewith packed inside a delivery catheter. In some such embodiments, the device is also provided with a second anchor associated with the tensioning member and packed inside the delivery catheter. In some such embodiments, the components of a device are configured for serial deployment through a distal end of the delivery catheter. In some such embodiments, the first anchor, for example, is packed closer to the distal end of the delivery catheter than other components, so as to allow the first anchor to be deployed prior to deployment of other components.

For example, as detailed hereinbelow in some embodiments a device of the present invention is provided with a second anchor and a tensioning member associated therewith packed inside a transapical probe. In some such embodiments, the device is also provided with a first anchor associated with the tensioning member and packed inside the transapical probe. In some such embodiments, the components of a device are configured for serial deployment through a distal end of the transapical probe. In some such embodiments, the second anchor, for example, is packed closer to the distal end of the transapical probe than other components, so as to allow the second anchor to be deployed prior to deployment of other components.

Exemplary embodiments of the method of the present invention are described hereinbelow with reference to deployment of exemplary embodiments of the device of the present invention. It should be noted that embodiments of the invention also include implementations where different features are provided form different embodiments, for example, materials, sizes, structures, material properties and/or process steps.

Figure 4A:
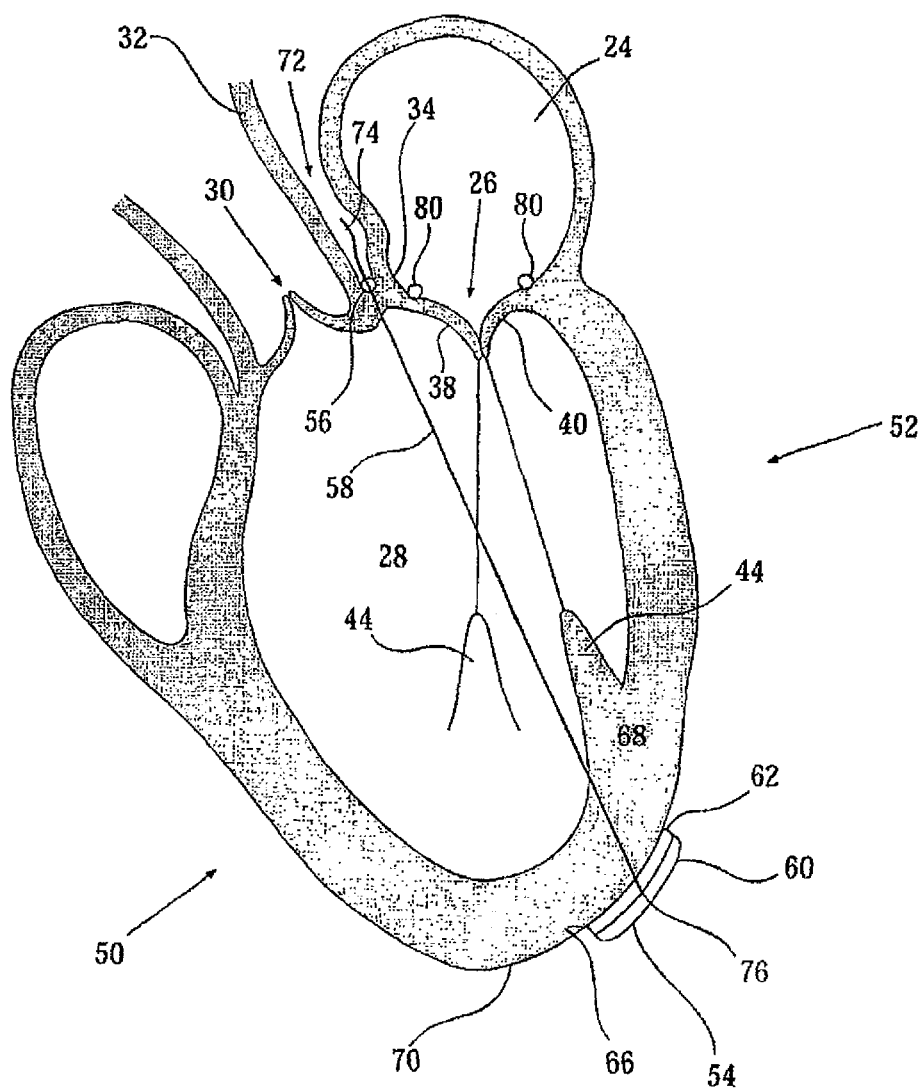
FIGS. 4A, 4B and 4C depict an embodiment of a device for applying pressure to portions of a heart comprising a first anchor including a curved plate of stainless steel mesh and an axially flexible second anchor.

In FIGS. 4A to 4E, a first embodiment of a device for applying pressure, force and/or movement limitation to a portion of a mammalian heart of the present invention, device 52 is depicted. In FIG. 4A, device 52 is depicted deployed in an ischemic heart 50. Device 52 comprises three discrete components: a pad assembly as a first anchor 54, a felt rod as a second anchor 56 and a suture strand as a tensioning member 58.

Figures 4B, 4C:
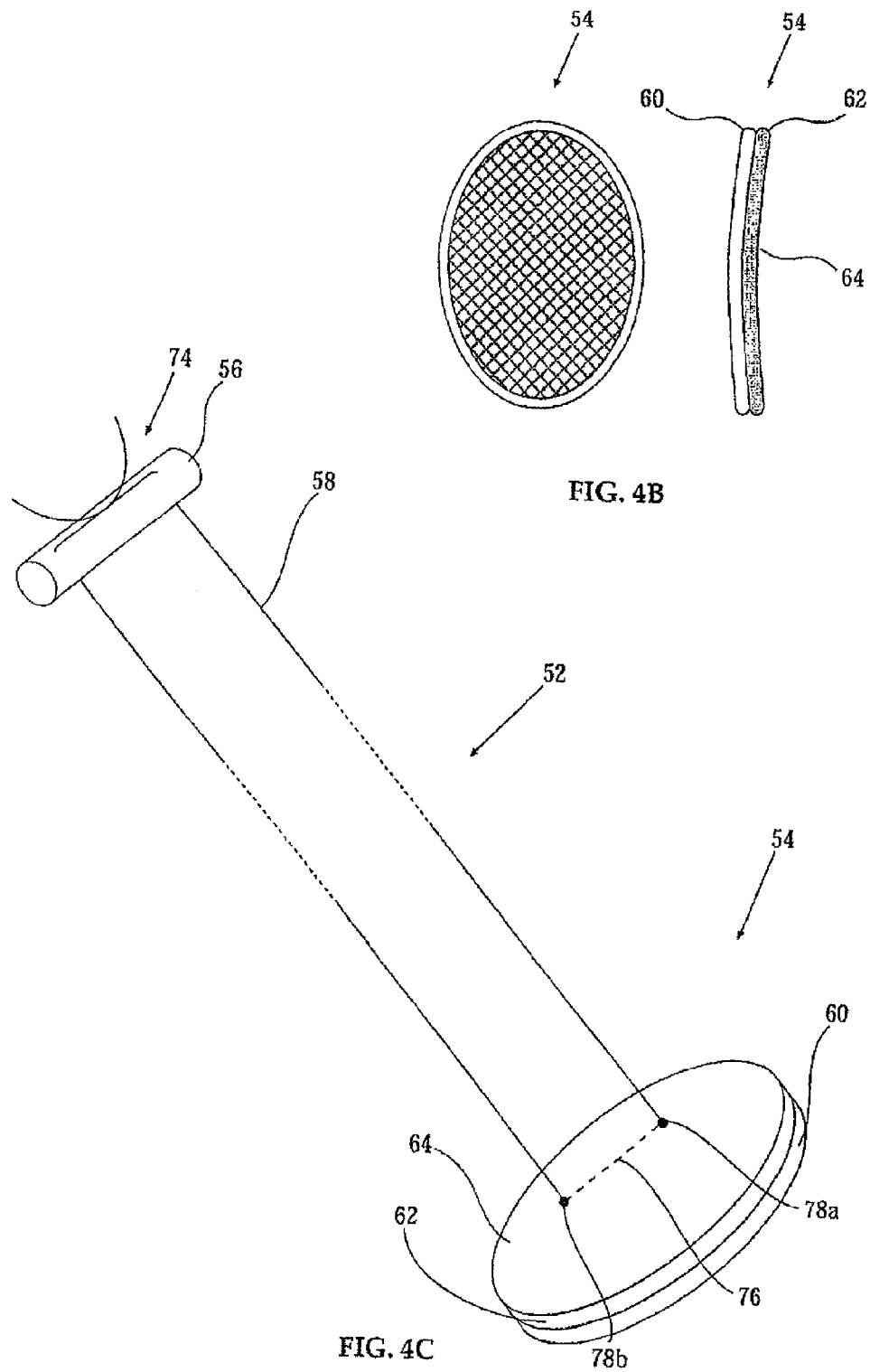
Figure 4D:
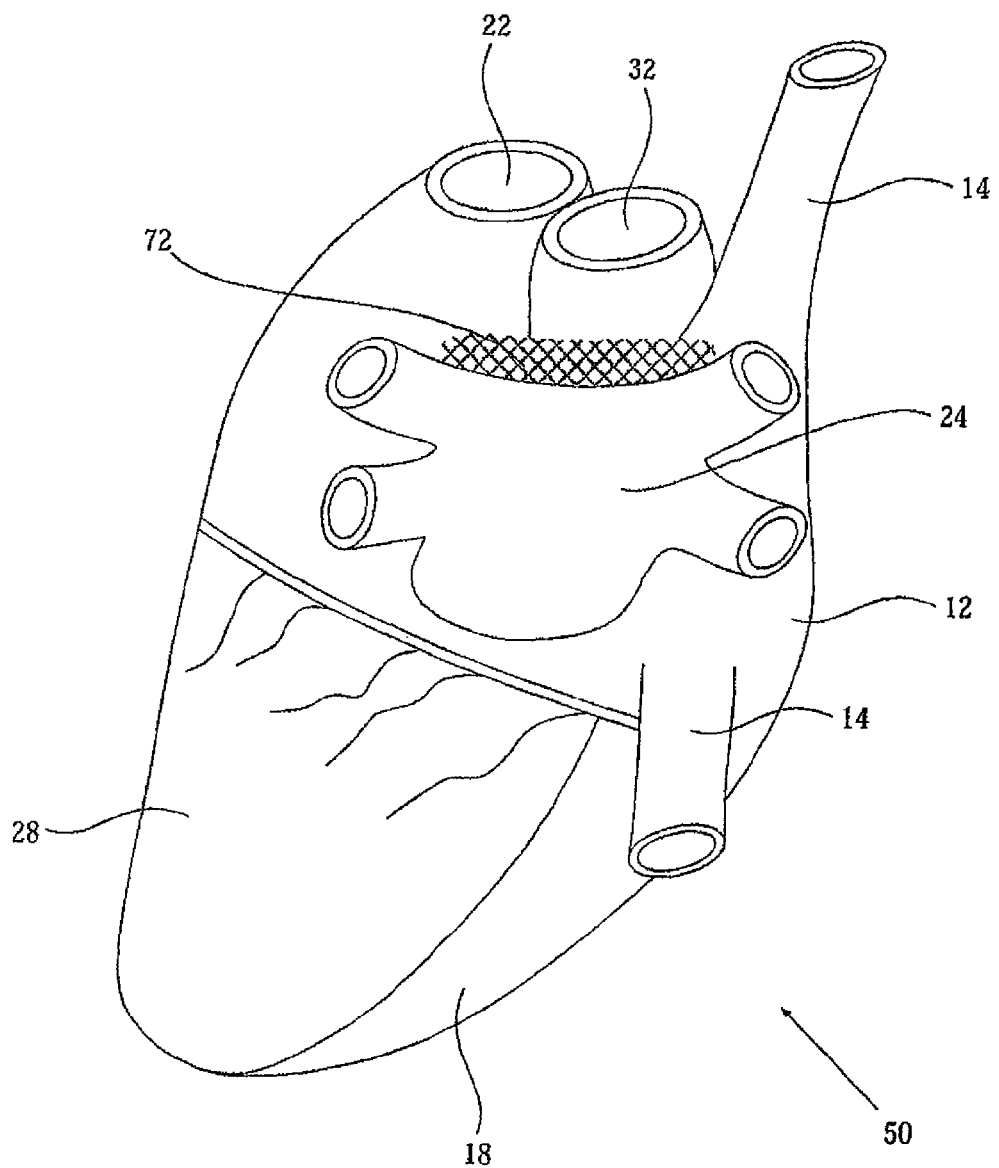
FIG. 4D is a schematic depiction of a heart showing the transverse pericardial sinus.
Figure 4E:
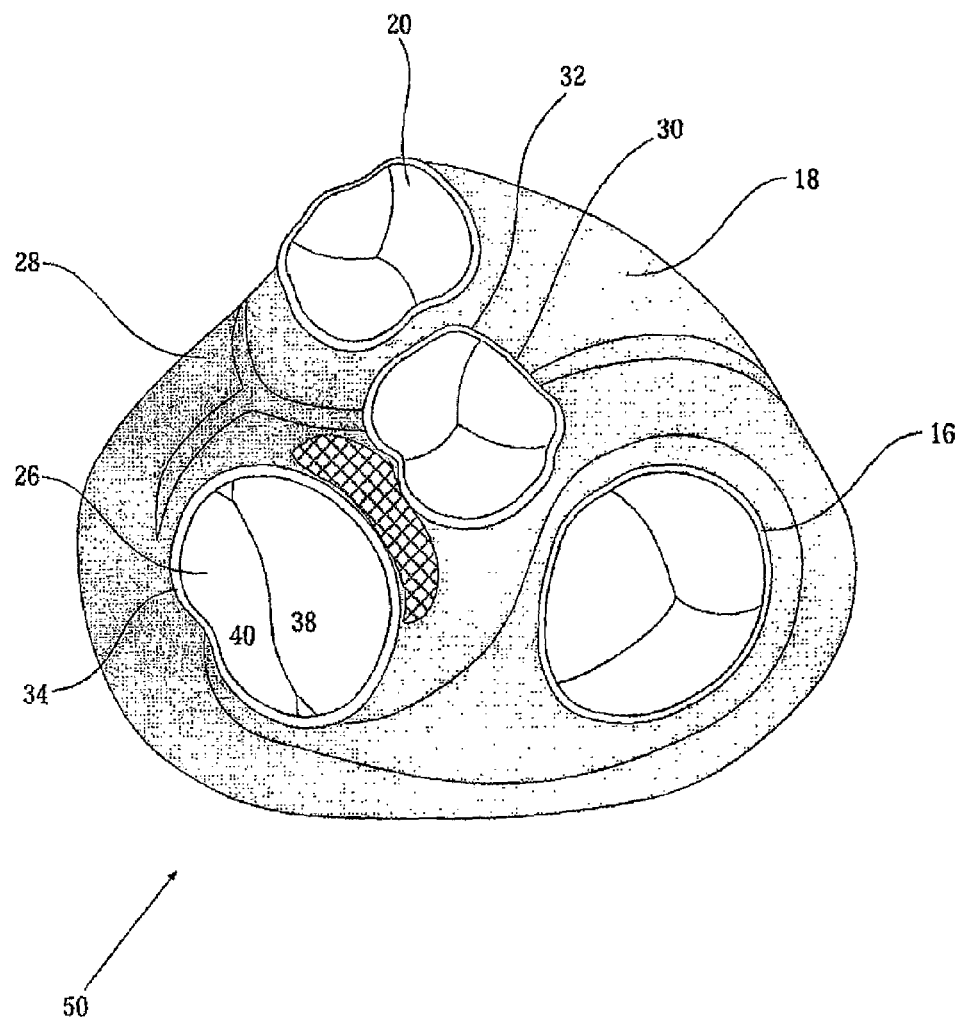
FIG. 4E is a schematic depiction of a top view of a heart with the atria removed.

First anchor 54 is depicted in detail in FIG. 4B in front view and side view. First anchor 54 is a single assembly consisting essentially of two components: a slightly-elastic curved plate of stainless steel mesh 60, 3 cm by 5 cm wide (having a surface area of about 12 cm$^2$) and a pliant layer 62 of 0.5 mm thick surgical felt located on the concave face of plate 60 so as to define a concave contact face 64. First anchor 54 is configured to be deployed entirely outside heart 50 so that contact face 64 contacts a surface 66 of an external wall 68 of left ventricle 28 of heart 50 in proximity of cardiac apex 70. Contact face 64 of first anchor 54 rests against the epicardium covering surface 66 of heart 50. Being made of a mesh plate 60 and a pliant layer 62, first anchor 54 is piercable and therefore configured to allow the passage of tensioning member 58 therethrough.

Second anchor 56 comprises a 2 cm long, 3 mm diameter rod of surgical felt configured to fit inside transverse pericardial sinus 72 of heart 50, in proximity to the aortic side of mitral valve annulus 34 over the midseptal fibrous annulus. Being made from felt, second anchor 56 is axially bendable and radially compressible and is thereby configured to fit inside transverse pericardial sinus 72 and to change in shape to accommodate the changes of shape of transverse pericardial sinus 72 as heart 50 beats. Being made of felt, second anchor 56 is also piercable and is thereby configured to allow the passage of tensioning member 58 therethrough.

Tensioning member 58 is filamentous, flexible, and is substantially a loop of axial unstretchable, 3-0 Prolene non-resorbable suture strand cut to the appropriate length and secured to first anchor 54 and second anchor 56, as depicted in FIG. 4C.

At an apical portion 76, tensioning member 58 passes through first anchor 54 at two locations defined by holes 78a and 78b, encircling a portion of first anchor 54 and ensuring that pressure is evenly applied to surface 66 of external wall 68 of heart 50. At a mitral portion 74 of tensioning member 58, the two ends of the suture strand making up tensioning member 58 pass through second anchor 56 at two substantially different locations, each location near a different end of second anchor 56. The ends of the suture strand are knotted together thereby constituting tensioning member 58. When taut, tensioning member 58 substantially defines a distance separating first anchor 54 and second anchor 56.

As is seen in FIG. 4A, mitral portion 74 of tensioning member 58 passes through cardiac tissue making up the roof of left ventricle 28 partially underneath and partially through mitral valve annulus 34 into the volume of left ventricle 28. As is seen in FIG. 4A, apical portion 76 of tensioning member 58 penetrates into and passes through external wall 68 of left ventricle 28 into the volume of left ventricle 28. Tensioning member 58 is smooth and slidingly passes through the heart tissue during the beating of heart 50.

An embodiment of a method for applying pressure to a heart is implemented by deploying device 52 in a heart 50.

For deployment of device 52, the heart 50 exposed, for example with a median sternotomy the patient is attached to a heart-lung machine, the beating of heart 50 stopped and a standard annuloplasty ring 80 is deployed, in the usual way, on the atrial side of mitral valve 26. It is noted that in other embodiments of the invention, a minimally invasive approach is used and/or the heart is not stopped and/or not opened.

Device 52 is provided disassembled as a kit comprising first anchor 54. Second anchor 56 is fashioned ad hoc from a piece of surgical felt found in a surgical theater and tensioning member 58 is fashioned ad hoc from suture strand also found in a surgical theater. In some embodiments, a kit comprises a first anchor 54 and a second anchor 56. In some embodiments, a kit comprises a first anchor 54, a second anchor 56 and suture strand (for example a spool of suture strand) constituting tensioning member 58.

First anchor 54 is placed against surface 66 of a portion of external wall 68 that is sagging as a result of a remodeling process.

The ends of a length of the suture strand are threaded through the eyes of two surgical needles, each end to a needle.

A first needle together with the accompanying end of the suture strand is passed through plate 60 of first anchor 54 at hole 78a, through pliant layer 62 to penetrate into and through external wall 68 of left ventricle 28. The first needle is passed through the roof of left ventricle 28 underneath (or through) the aortic side of mitral valve annulus 34 (hatched area in FIG. 4E where heart 50 is depicted with atria 12 and 24 removed) to emerge out into transverse pericardial sinus 72 (hatched area in FIG. 4D), thereby drawing a first length of the suture strand across the volume of left ventricle 28.

A second needle together with the accompanying end of the suture strand is passed through plate 60 of first anchor 54 at hole 78b, through pliant layer 62 to penetrate into and through external wall 68 of left ventricle 28 and passed through the roof of left ventricle 28 underneath (or through) the aortic side of mitral valve annulus 34 to emerge out into transverse pericardial sinus 72, thereby drawing a second length of the suture strand across the volume of left ventricle 28. As a result, the suture strand penetrates through first anchor 54 in two places (holes 78a and 78b) and encircles a portion thereof.

The two needles with the two ends of the suture strand are passed through second anchor 56. Second anchor 56 is pushed slidingly downwards along the suture strand to contact the bottom of transverse pericardial sinus 72 so as to be deployed in proximity to the aortic side of mitral valve 26 of heart 50. The two ends of the suture are brought together to constitute a loop that is tensioning member 58 and thus to secure tensioning member 58 to first anchor 54 and second anchor 56.

The beating of heart 50 is restarted and the patient disconnected from the heart-lung machine.

Under guidance, for example, of TEE (transesophageal echocardiography) the two ends of the suture strand are pulled to shorten tensioning member 58 and thus decrease the distance between first anchor 54 and second anchor 56. Alternatively, the two ends of the suture strand are released to lengthen tensioning member 58 and thus increase the distance between first anchor 54 and second anchor 56. As the distance is increased or decreased, the change in the structure of mitral valve 26, coaptation and alignment of leaflets 38 and 40 and the degree of regurgitation is monitored until the surgeon performing the deployment of device 52 decides that the length of tensioning member 58 is sufficient. The ends of the suture strand are secured together by knotting and the procedure ended. In other embodiments, the suture is fixed in place prior to restarting the heart.

After the patient recovers, heart 50 beats. When and if external wall 68 bulges outwards, tensioning member 58 is held taut. Contact face 64 presses against surface 66 of external wall 68, supporting the sagging portion of heart 50. Papillary muscles 44 are prevented from moving outwards, reducing the tension applied by chordae 46 on leaflets 38 and 40, allowing leaflets 38 and 40 to properly coapt, reducing mitral regurgitation. In some cases, the support of the sagging portion of external wall 68 of left ventricle 28 together with the improvement of mitral valve leaflet coaptation may reverse cardiac remodeling or have other positive effects. Pliant layer 62 optionally acts as shock absorber, reducing pressure-trauma during beating of heart 50 and distributing pressure on surface 66 more evenly than otherwise.

Figure 5A:
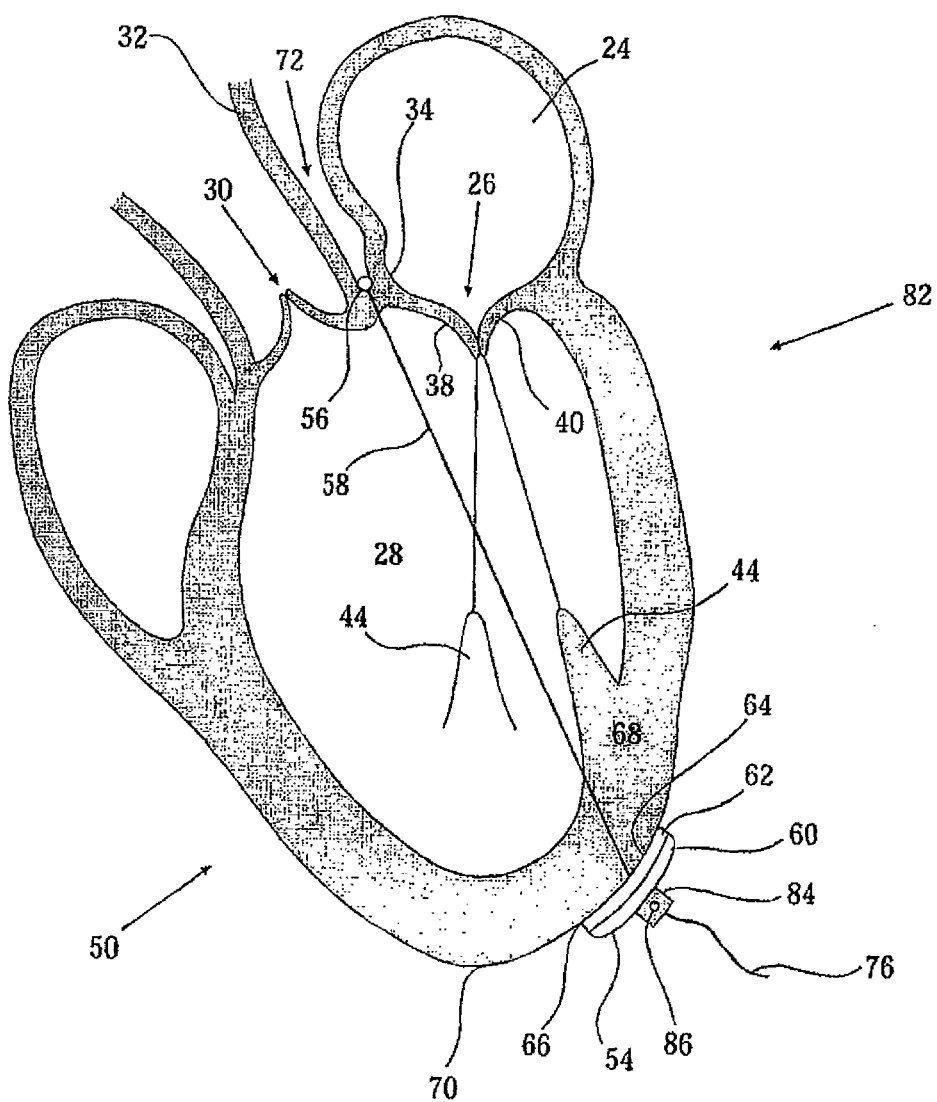
FIGS. 5A and 5B depict an embodiment of a device for applying pressure to portions of a heart comprising a first anchor including a curved plate of PMMA mesh and a second anchor including a rigid curved cylinder of stainless steel.
Figure 5B:
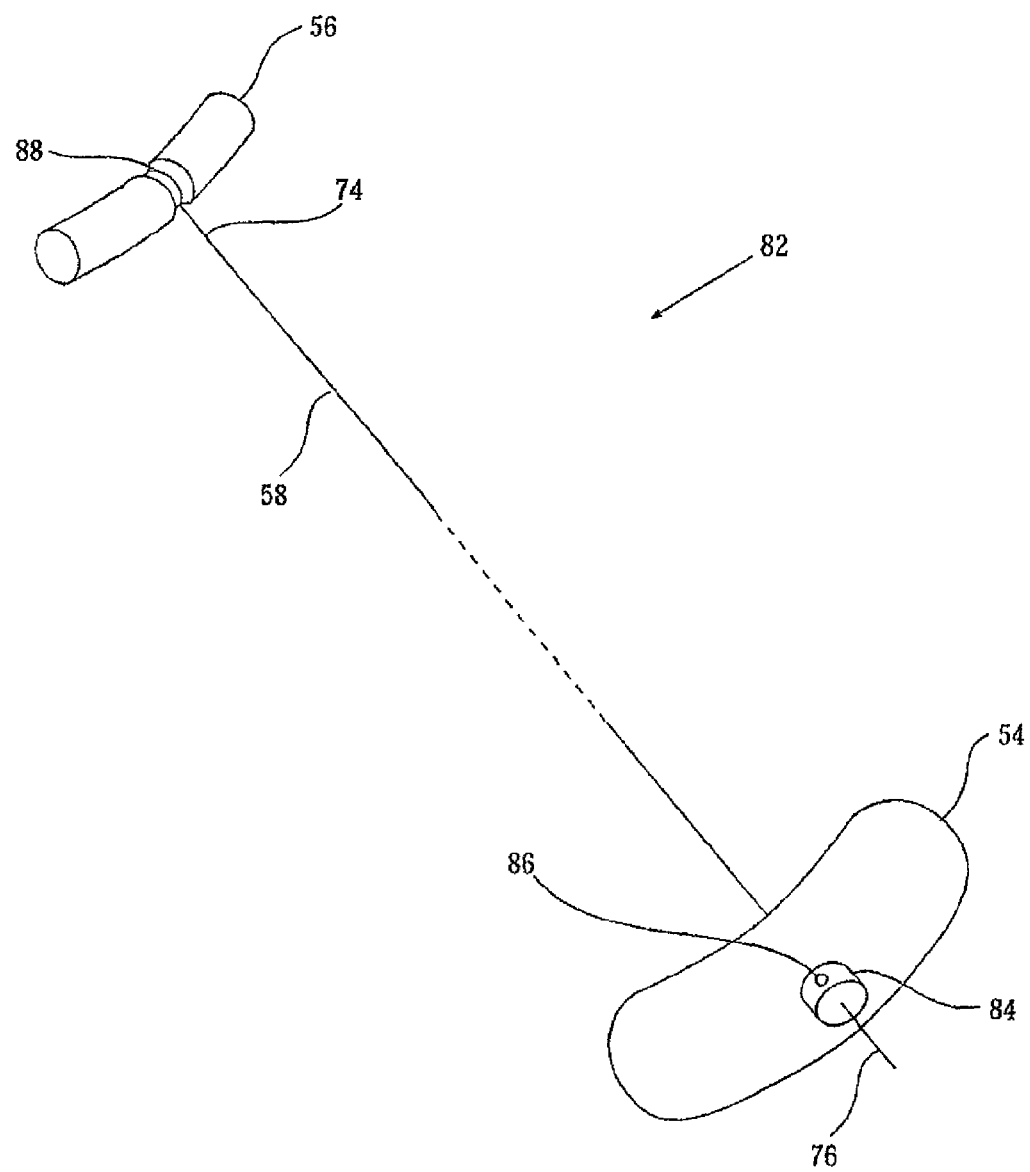

In FIGS. 5A and 5B, a second embodiment of a device of the present invention, device 82 is depicted, in FIG. 5A deployed in an ischemic heart 50. In device 82, the distance between first anchor 54 and second anchor 56 is adjustable when deployed in a heart 50, and even when heart 50 is beating.

First anchor 54 of device 82 is substantially similar to first anchor 54 of device 52 but is made of PMMA (polymethyl methylacrylate) instead of stainless steel. First anchor 54 of device 82 is configured so that tensioning member 58 is reversibly securable to first anchor 54 when device 82 is deployed in a heart 50 and, in some embodiments, while heart 50 is beating. Specifically, first anchor 54 is provided with a retaining nut 84 with an axial hole passing therethrough to accommodate a tensioning member 58 and a locking screw 86 disposed in a screw hole perpendicular to the axial hole. Such a construction allows the location along tensioning member 58 where tensioning member 58 is secured to first anchor 54 to be changed.

Second anchor 56 of device 82 is a rigid curved cylinder of stainless steel, 3 cm long and 2 mm in diameter. Midway between the ends of second anchor 56 is a groove 88.

Tensioning member 58 of device 82 is suture strand similar to tensioning member 58 of device 52. Mitral portion 74 of tensioning member 58 is formed into a loop that rests inside groove 88 and encircles second anchor 56. Apical portion 76 of tensioning member 58 is a single length of suture strand which passes through the axial hole of retaining nut 84. Locking screw 86 is screwed inwards in retaining nut 84 to an extent that locking screw 86 engages a part of apical portion 76 of tensioning member 58 to secure tensioning member 58 to first anchor 54.

An embodiment of the method of the present invention is implemented by deploying device 82 in a heart 50.

A patient is attached to a heart-lung machine, the beating of heart 50 stopped and heart 50 exposed, for example with a median sternotomy. In the embodiment depicted in FIG. 5A, no annuloplasty ring is deployed in heart 50.

Device 82 is provided disassembled as a kit comprising first anchor 54, second anchor 56 and a spool of suture strand constituting tensioning member 58.

Contact face 64 of first anchor 54 is placed against portion of external wall 68 of heart 50 near apex 70 that is sagging as a result of a remodeling process.

Mitral portion 74 of tensioning member 58 is threaded through the eye of a surgical needle. Apical portion 76 of tensioning member 58 is threaded through the axial hole in retaining nut 84. The needle together with mitral portion 74 of tensioning member 58 is passed through plate 60 of first anchor 54, through pliant layer 62 to penetrate into and through external wall 68 of left ventricle 28. The needle is passed through the roof of left ventricle 28 underneath (or through) the aortic side of mitral valve annulus 34 to emerge out into transverse pericardial sinus 72, thereby drawing tensioning member 58 across the volume of left ventricle 28.

The needle is detached from tensioning member 58 and mitral portion 74 of tensioning member 58 is looped around so as to encircle second anchor 56 and the loop tightened to rest inside groove 88, preventing mitral portion 74 of tensioning member 58 from sliding along the length of second anchor 56. While retaining nut 84 is held against first anchor 54, apical portion 76 of tensioning member 58 is carefully pulled outwards from heart 50, drawing mitral portion 74 and second anchor 56 into transverse pericardial sinus 72 until second anchor 56 rests at the bottom of transverse pericardial sinus 72. Apical portion 76 of tensioning member 58 is pulled outwards through the axial hole of retaining nut 84 until the length of tensioning member 76 is such that a desired distance is defined between first anchor 54 and second anchor 56. Locking screw 86 is tightened to engage a location along apical portion 76 of tensioning member 58 to maintain the selected length of tensioning member 58 and thus the distance between first anchor 54 and second anchor 56.

The beating of heart 50 is restarted and the structure of mitral valve 26, coaptation and alignment of leaflets 38 and 40 and the degree of regurgitation is observed, for example with the help of TEE. If the surgeon performing the deployment of device 82 determines that it is necessary, the length of tensioning member 58 is adjusted by loosening locking screw 86 and then apical portion 76 of tensioning member 58 is pulled to shorten tensioning member 58 and thus decrease the distance between first anchor 54 and second anchor 56 or apical portion 76 is released to lengthen tensioning member 58 and thus increase the decrease the distance between first anchor 54 and second anchor 56. Locking screw 86 is tightened to engage a location along apical portion 76 to maintain the selected length of tensioning member 58 and thus the distance between first anchor 54 and second anchor 56. The adjustment of the length of tensioning member 58 is repeated until the performing surgeon determines that the length is correct and the procedure is ended.

As noted above, apical portion 76 of tensioning member 58 and first anchor 54 are configured so that tensioning member 58 is reversibly securable to first anchor 54, when deployed, rendering the distance between first anchor 54 and second anchor 56 adjustable when deployed. If after a time (e.g., a few days) there is a reason, for example a clinical reason, to change the distance defined by tensioning member 58, apical portion 76 of tensioning member 58, first anchor 54, retaining nut 84 and locking screw 86 are engaged from the direction of apex 70, for example using standard cardiothoracic surgical techniques through a median sternotomy. While apical portion 76 of tensioning member 58 is grasped (to avoid escape into heart 50) locking screw 86 is released. The distance defined between second anchor 56 and first anchor 54 is either increased by allowing apical portion 76 to pull back into heart 50 (reducing the pressure applied on heart 50) or decreased by pulling apical portion 76 outwards (increasing the pressure applied on heart 50) while holding first anchor 54 against heart 50. When the desired new distance is defined, locking screw 86 is tightened to fix apical portion 76 in place. Thus, the distance is adjustable by changing the location of apical portion 76 through which tensioning member 58 is secured to first anchor 54.

Figure 6A:
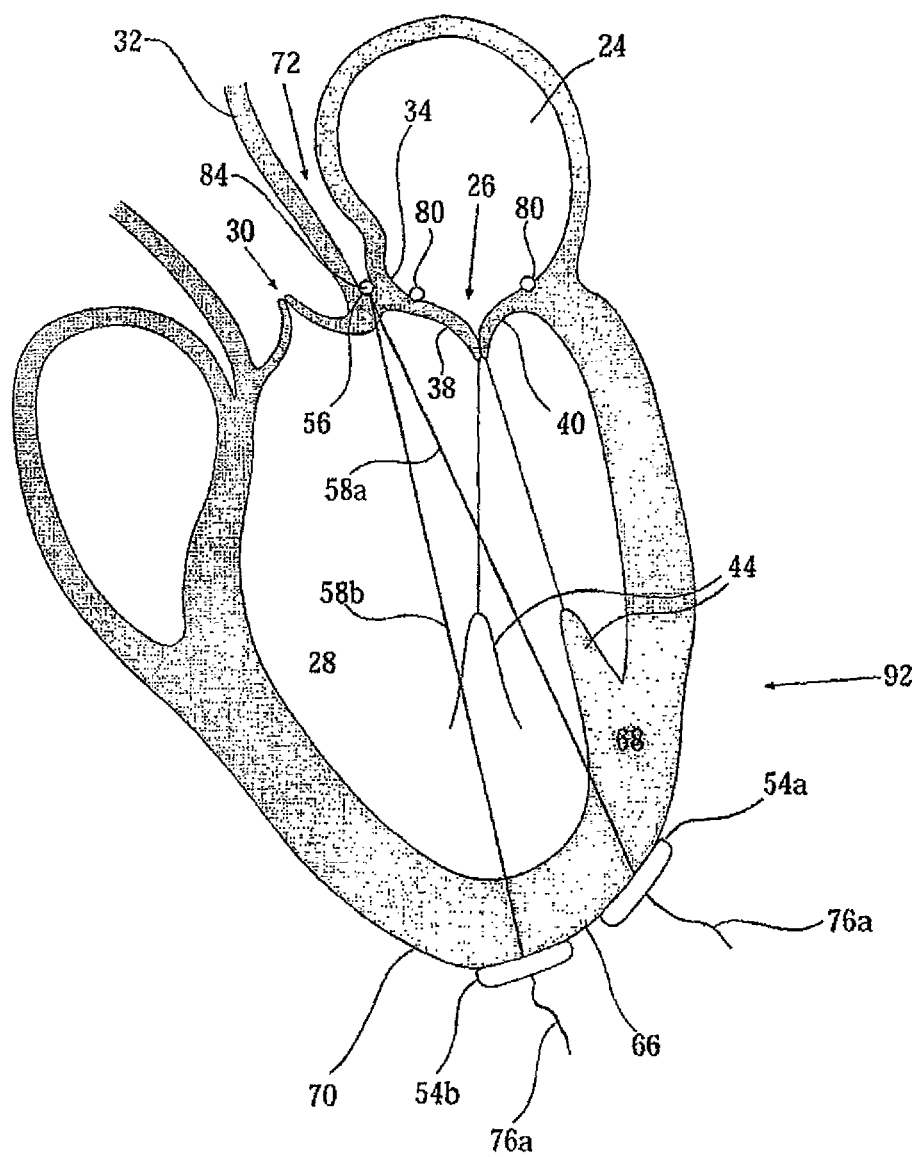
FIGS. 6A and 6B depict an embodiment of a device for applying pressure to portions of a heart comprising a first anchor including two discrete assemblies and a second anchor.
Figure 6B:
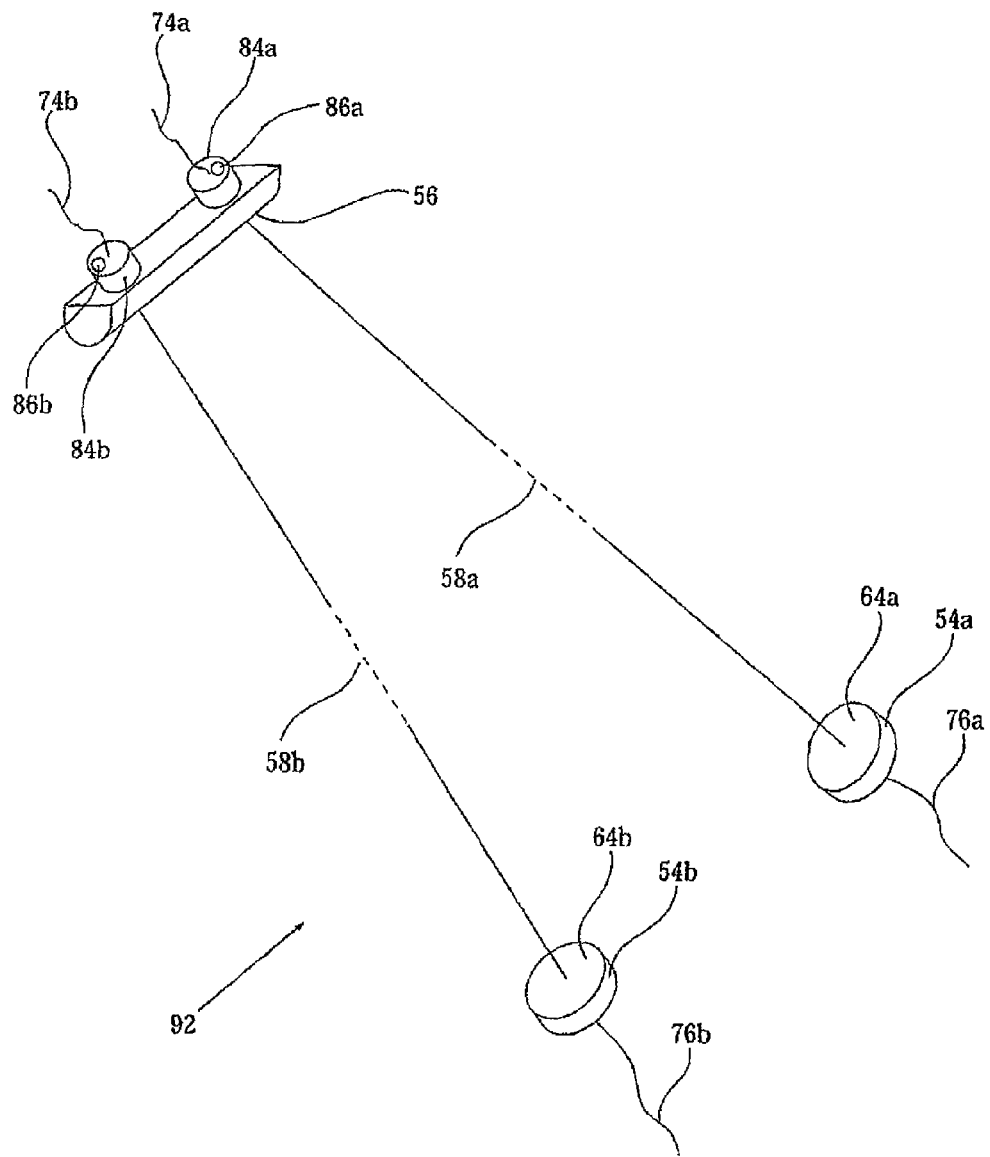

In FIGS. 6A and 6B, a third embodiment of a device of the present invention, device 92 is depicted, in FIG. 6A deployed in an ischemic heart 50. In device 92, first anchor 54 comprises two discrete assemblies 54a and 54b with two discrete tensioning members 58a and 58b. Each tensioning member 58a and 58b defines a distance between a second anchor 56 and a respective assembly 54a and 54b. Each of the distances is independently adjustable when device 92 is deployed in a heart 50 even when heart 50 is beating.

Each first anchor assembly 54a and 54b of device 82 is substantially similar to pads used in a Coapsys® device (Myocor, Inc., Maple Grove, Minn., USA).

Second anchor 56 of device 92 is a 2 cm length of surgical felt having a 3 mm diameter oblate semicircular cross section. Second anchor 56 of device 92 is configured allowing a tensioning member 58a or 58b to be reversibly securable to second anchor 56 when device 92 is deployed in heart 50 and, in some embodiments, while heart 50 is beating. Specifically, second anchor 56 is provided with two retaining nuts 84a and 84b each with an axial hole passing therethrough to accommodate a tensioning member 58a or 58b and a locking screw 86a or 86b disposed in a screw hole parallel to the axial hole. Such a construction allows the location along a tensioning member 58a or 58b where the tensioning member is secured to a second anchor 56 to be changed.

Each tensioning member 58a or 58b is a single length of suture strand like tensioning member 58 of device 52. Apical portions 76a or 76b of tensioning members 58a and 58b pass through a hole in a respective first anchor assembly 54a or 54b. Mitral portions 74a or 74b pass through an axial hole of a retaining nut 84a or 84b. A locking screw 86a or 86b is screwed inwards in a retaining nut 84a or 84b to an extent that the locking screw engages a respective part of a mitral portion 74a or 74b to secure a tensioning member 58a or 58b to second anchor 56.

In some alternative embodiments of the invention the tensioning members 58a or 58B optionally include shape memory material, for example, as described above in a section referring to the tensioning member.

An embodiment of a method for applying pressure to a heart is implemented by deploying device 92 in a heart 50.

A patient is attached to a heart-lung machine, the beating of heart 50 stopped and heart 50 exposed, for example with a median sternotomy. In the embodiment depicted in FIG. 6A, an annuloplasty ring 80 is deployed in heart 50.

Device 92 is provided disassembled as a kit comprising first anchor assemblies 54a and 54b, second anchor 56 and a spool of suture strand constituting tensioning members 58a and 58b.

Mitral portion 74a of tensioning member 58a is threaded through the eye of a surgical needle. Apical portion 76a of tensioning member 58a is secured to first anchor assembly 54a. The needle together with mitral portion 74a of tensioning member 58a is passed through a portion of external wall 68 of heart 50 that is sagging as a result of a remodeling process to penetrate into and through external wall 68 of left ventricle 28. The needle is passed through the roof of left ventricle 28 underneath (or through) the aortic side of mitral valve annulus 34 to emerge out into transverse pericardial sinus 72, thereby drawing tensioning member 58a across the volume of left ventricle 28.

Mitral portion 74b of tensioning member 58b is threaded through the eye of a surgical needle. Apical portion 76b of tensioning member 58b is secured to second anchor assembly 54b. The needle together with mitral portion 74b of tensioning member 58b is passed through a portion of external wall 68 of heart 50 that is sagging as a result of a remodeling process to penetrate into and through external wall 68 of left ventricle 28. The needle is passed through the roof of left ventricle 28 underneath (or through) the aortic side of mitral valve annulus 34 to emerge out into transverse pericardial sinus 72, thereby drawing tensioning member 58b across the volume of left ventricle 28.

Mitral portions 74a and 74b of tensioning members 58a and 58b are passed through the felt material of second anchor 56 and threaded through the axial holes in retaining nuts 84a and 84b. Second anchor 56 is allowed to slide along tensioning members 58a and 58b until coming to rest at the bottom of transverse pericardial sinus 72.

The beating of heart 50 is restarted. Under guidance, for example of TEE, mitral portions 74a and 74b of tensioning members 58a and 58b are independently pulled to shorten a respective tensioning member 58 and thus decrease the distance between a first anchor assembly 54a or 54b and second anchor 56 or, alternatively, released to lengthen a respective tensioning member 58 and thus increase the distance between a first anchor assembly 54a or 54b and second anchor 56. As the two distances are increased or decreased, the change in the structure of mitral valve 26, coaptation and alignment of leaflets 38 and 40 and the degree of regurgitation is observed until the surgeon performing the deployment of device 92 decides that the length of tensioning members 58a and 58b is sufficient. Locking screws 86a and 86b are tightened to engage a location along mitral portion 74a or 74b to maintain the selected length of the respective tensioning member 58a or 58b and thus the distance between the first anchor assembly 54a or 54b and second anchor 56. The procedure is ended.

After the patient recovers, heart 50 beats and device 92 functions substantially as described above for device 52.

As noted above, mitral portions 74a and 74b of tensioning members 58 and second anchor 56 are configured so that tensioning members 58 are reversibly securable to second anchor 56, when device 92 is deployed in a heart 50, rendering the distances between first anchor assemblies 54a and 54b and second anchor 56 adjustable when deployed in heart 50. If after a time (e.g., a few days) there is a reason, for example a clinical reason, to change one or both distances defined by tensioning members 58, mitral portions 74 of tensioning members 58, second anchor 56, retaining nuts 84 and locking screws 86 are engaged from the direction of transverse pericardial sinus 72, for example using a median sternotomy. While a mitral portion 74a or 74b of a respective tensioning member 58 is grasped (to avoid escape into heart 50) a respective locking screw 86a or 86b is released. The distance defined between second anchor 56 and a first anchor assembly 54a or 54b is either increased by allowing a respective mitral portion 74 to pull back into heart 50 (reducing the pressure applied on heart 50) or decreased by pulling a respective mitral portion 74 outwards while holding second anchor 56 against heart 50 (increasing the pressure applied on heart 50). When a desired new distance is defined, the locking screw 86 is tightened to fix mitral portion 74 in place. Thus, one or more distances are adjustable by changing the location of a mitral portion 74 through which a respective tensioning member 58 is secured to second anchor 56.

Some embodiments, such as device 92, have a potential advantage that the use of more than one discrete first anchor assembly provides more freedom as to how much and where pressure is applied to heart 50.

First anchor 54 of device 92 depicted in FIG. 6 comprises two discrete assemblies 54a and 54b. In some embodiments, a first anchor of a device comprises more than two discrete assemblies.

Device 92 depicted in FIG. 6 comprises two tensioning members 58a and 58b. In some embodiments, a device comprises more than two tensioning members.

Device 92 depicted in FIG. 6 comprises two tensioning members 58a and 58b secured to different locations of second anchor 56. In some embodiments, more than one tensioning member is secured to substantially the same location of a second anchor.

Device 92 depicted in FIG. 6 comprises two tensioning members 58a and 58b secured to different locations of second anchor 56, each tensioning member secured to a different assembly of first anchor 54. In some embodiments, more than one tensioning member is secured to substantially the same location of a first anchor.

Figure 7A:
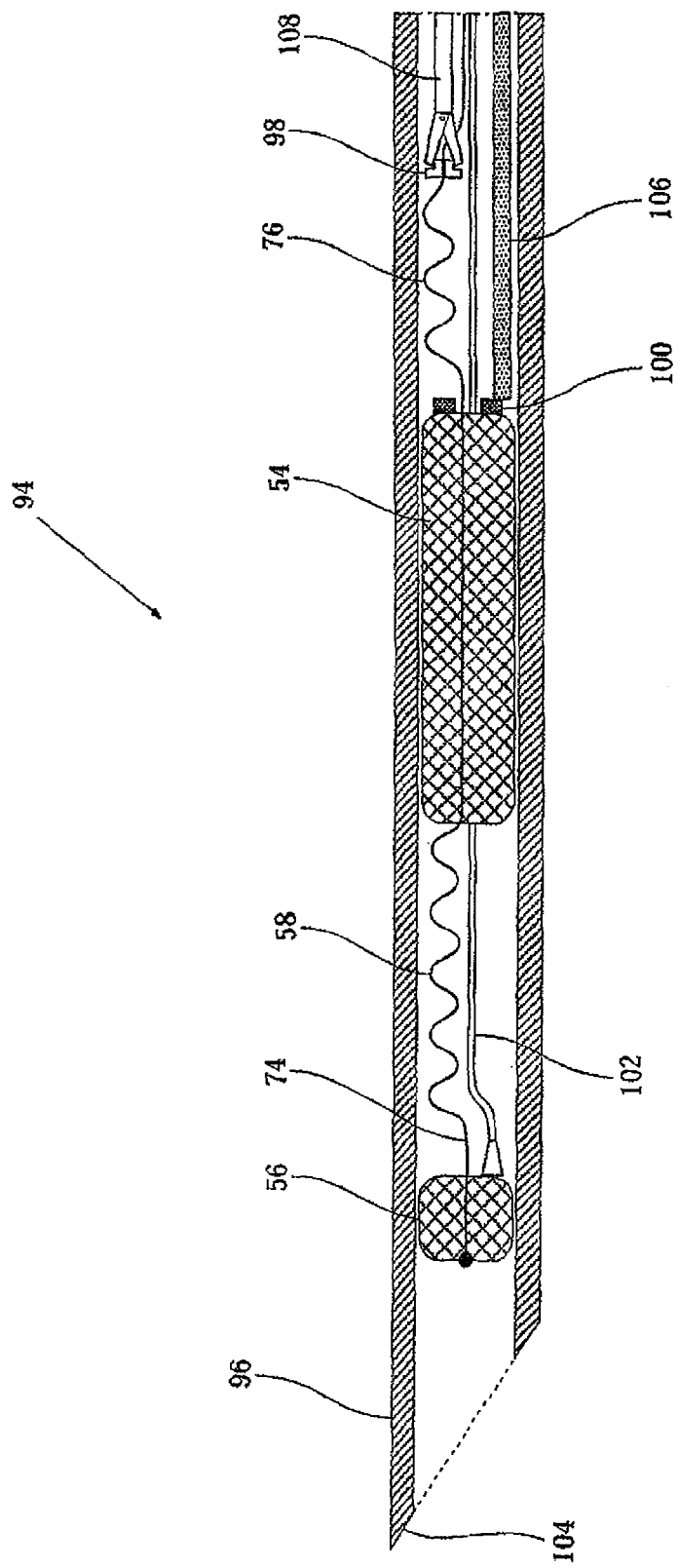
Figure 7B:
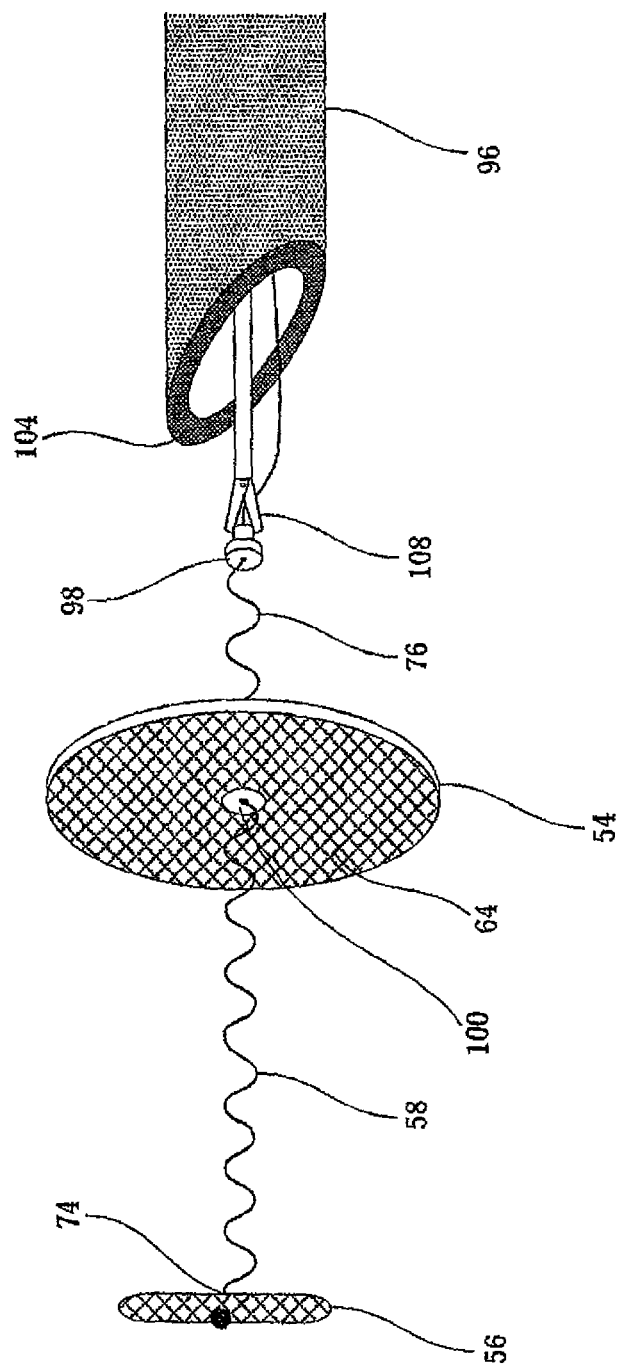

A fourth embodiment of a device of the present invention, device 94, is depicted in FIGS. 7A and 7B. Device 94 is configured for minimally-invasive transapical deployment. Various stages of minimally-invasive transapical deployment of device 94 are depicted in FIGS. 7C to 7I.

In FIG. 7A, device 94 is depicted packed inside a hollow transapical probe 96 configured for use with a transthorax surgical robot (such as the da Vinci® Surgical Robot by Intuitive Surgical, Inc., Sunnyvale, Calif., USA). In other embodiments, for example as described below, the probe is held manually. Inside the bore of transapical probe 96 are seen components of device 94: a shape-memory wire mesh constituting first anchor 54, a shape-memory wire mesh constituting second anchor 56, a suture filament as a tensioning member 58 and a crimpable retainer ring 98. In FIG. 7B, device 94 is depicted released from the constraints of the bore of transapical probe 96. It is seen that, when allowed to expand, first anchor 54 optionally adopts the shape of concave-convex disk with a concave side defining a contact face 64 facing second anchor 56. Also seen is that when allowed to expand, second anchor 56 optionally adopts a rod-shape suitable in size and shape to fit inside a transverse pericardial sinus 72. Both first anchor 54 and second anchor 56 are optionally shape-memory wire mesh configured to self-expand when released from the constraints of the bore of transapical probe 96. First anchor 54 and second anchor 56 are optionally made from materials and in a manner with which a person having ordinary skill in the art is familiar, and are analogous to anchors such as taught in the patent publications US 2006/0241340, US 2007/0203391 and US 2007/0078297. Other anchor designs may be used as well.

In an exemplary embodiment of the invention, a mitral portion 74 of tensioning member 58 passes into and is secured (for example by tying or looping) to the mesh making up second anchor 56. An apical portion 76 of tensioning member 58 passes through a base ring 100 in the center of first anchor 54. Encircling tensioning member 58 in a proximal direction from the convex side of first anchor 54 is crimpable retainer ring 98.

As depicted in FIG. 7A, when packed inside transapical probe 96, first anchor 54 is in contact with a first push rod 102. First push rod 102 passes from the proximal end of transapical probe 96 (not depicted), to contact the proximal side of first anchor 54. Transapical probe 96 is configured to allow actuation of first push rod 102 to push first anchor 54 out of transapical probe 96. Optionally, the rod is configured as a tube or other means such as known in the art for pushing an object out of a tube. In one example, a short spike (not shown) extends form probe 96, such that when probe 96 is retracted, the spike engages surrounding tissue and pulls out first anchor 54.

As depicted in FIG. 7A, when packed inside transapical probe 96, second anchor 56 is close to piercing tip 104 of transapical probe 96 and in contact with a second push rod 106. Second push rod 106 passes from the proximal end of transapical probe 96 (not depicted), through base ring 100 of first anchor 54 to contact the proximal side of second anchor 56. Transapical probe 96 is configured to allow actuation of second push rod 106 to push second anchor 56 out of transapical probe 96.

As depicted in FIGS. 7A and 7B, crimpable retainer ring 98 is encircled by the jaws of crimper-cutter 108. Transapical probe 96 is configured to allow actuation of crimper-cutter 108, closing the jaws to crimp crimpable retainer ring 98 around tensioning member 58. When the jaws of crimper-cutter 108 are actuated to close, blades inside crimper cutter 108 (not visible in the Figures) cut through a portion of tensioning member 58 that passes therebetween, proximally to crimpable retainer ring 98. In an alternative design, tensioning member 58 is pre-fixed to the two anchors and no crimping mechanism is needed.

A minimally-invasive transapical embodiment of the method of the present invention for applying pressure to a heart is implemented by deploying device 94 in a heart 50 of a subject. For deployment, transapical probe 96 with device 94 loaded therein is mounted on a suitable surgical robot and the subject is appropriately prepared while heart 50 is still beating. Optionally, the heart is stopped. Optionally or alternatively, the probe is used with a larger opening in the chest, for example, as part of an open chest procedure with sternum opening.

Figure 7C:
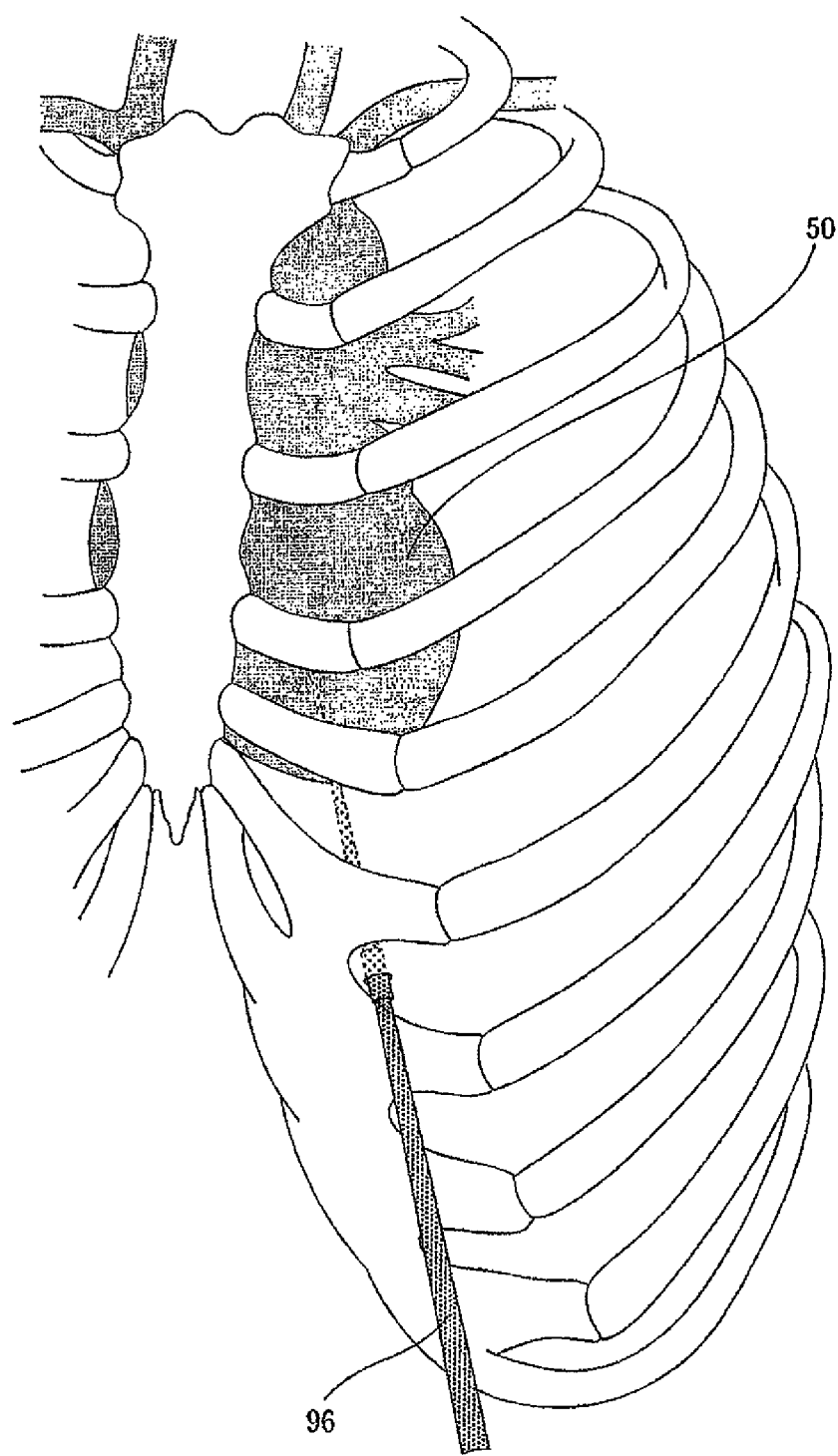

In FIG. 7C, transapical probe 96 is directed, optionally in the usual way, between the ribs of the subject, to penetrate into a left ventricle 28 of heart 50 near apex 70 or at a different desired location, for example, through a portion of external wall 68 that is sagging as a result of a remodeling process.

In FIG. 7D, transapical probe 96 is directed so as to pass clear through the base of left ventricle 28, underneath (or through) the aortic side of mitral valve annulus 34 to emerge out into transverse pericardial sinus 72. In some embodiments, other sides of the mitral valve are targeted.

In FIG. 7E, second push rod 106 is actuated, pushing second anchor 56 out of the bore of transapical probe 96. Freed of constraints, second anchor 56 expands to fit inside transverse pericardial sinus 72.

In FIG. 7F, probe 96 is withdrawn from heart 50 trailing tensioning member 58.

In FIG. 7G, first push rod 102 is actuated, pushing first anchor 54 out of the bore of transapical probe 96. Freed of constraints, first anchor 54 expands to the expanded concave-convex lens shape where the concave side faces surface 66 of heart 50.

In an exemplary embodiment of the invention, anchor 54 is configured to seal bleeding form the left ventricle.

Figures 7H, 7I:
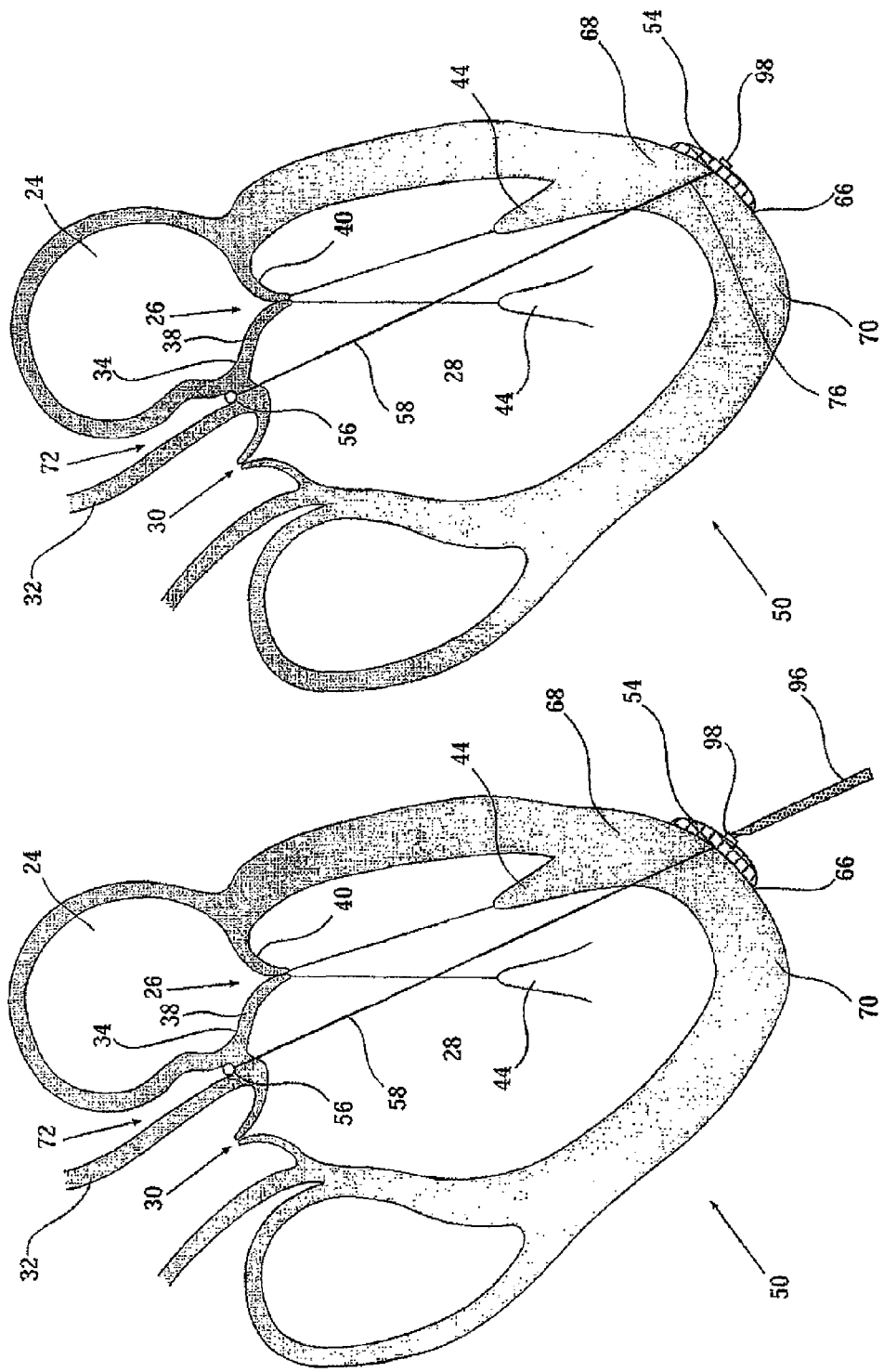

In FIG. 7H, tensioning member 58 is drawn taut while the end of crimper-cutter 108 is pressed against crimpable retainer ring 98 and base ring 100 of first anchor 54. The tension applied by tensioning member 58 is optionally varied while viewing the magnitude of regurgitation into left atrium during ventricular systole with an imaging modality (e.g., TEE) as described above: the tension is increased to decrease the distance between first anchor 54 and second anchor 56 as defined by tensioning member 58 and the tension is decreased to increase the distance between first anchor 54 and second anchor 56. As the distance is increased or decreased, the change in the structure of mitral valve 26, coaptation and alignment of leaflets 38 and 40 and the degree of regurgitation is monitored until the surgeon performing the deployment of device 94 decides that the length of tensioning member 58 is sufficient. When a given tension provides a desired reduction or elimination of regurgitation into left atrium 24, crimper-cutter 108 is activated to crimp crimpable retainer ring 98 around tensioning member 58, thereby defining the distance between first anchor 54 and second anchor 56 and also cutting through the apical portion 76 of tensioning member 58. The procedure is ended.

In an alternative embodiment, tensioning member 58 is prefixed to the anchors and no adjusting need be done.

In some alternative embodiments of the invention the tensioning member 58 optionally includes shape memory material, for example, as described above in a section referring to the tensioning member.

Optionally, a plurality of second anchors are applied by repositioning the tip of probe 96 while probe 96 still transfixed the left atrium.

After the patient recovers, heart 50 beats. When and if external wall 68 bulges outwards, tensioning member 58 is held taut. Contact face 64 presses against surface 66 of external wall 68, supporting the sagging portion of heart 50. Papillary muscles 44 are prevented from moving outwards, reducing the tension applied by chordae 46 on leaflets 38 and 40, allowing leaflets 38 and 40 to properly coapt, reducing mitral regurgitation. In some cases, the support of the sagging portion of external wall 68 of left ventricle 28 together with the improvement of mitral valve leaflet coaptation reverses cardiac remodeling. In an exemplary embodiment of the invention, the flexibility of the structure of first anchor 54 and second anchor 56 allow the anchors to act as shock absorbers, reducing pressure-trauma during beating of heart 50 and distributing pressure on surface 66 more evenly than otherwise.

A fifth embodiment of a device of the present invention, device 100, is depicted in FIGS. 8A to 8E. Like device 94, device 110 is configured for transapical deployment, with a number of noteworthy differences, one or more of which may be applied in various embodiments of the invention.

As described above, device 94 is deployed with the help of transapical probe 96 that is configured to hold and deploy substantially all components of device 94, including first anchor 54, second anchor 56, tensioning member 58 and crimpable retainer ring 98. In contrast, in some embodiments such as device 110 and as described below, a transapical probe for deploying a device of the present invention is configured to hold and deploy fewer components. In device 110 only second anchor 56 and tensioning member 58 are held within and deployed with the help of transapical probe 96. As discussed above, after second anchor 56 and tensioning member 58 are deployed and transapical probe 96 is withdrawn from the heart, an apical section 76 of tensioning member 58 is left trailing from the puncture in heart 50 through which transapical probe 96 entered. First anchor 54 is then deployed, substantially as described above, for example through a hole in the thorax, optionally via a tubular delivery system, such as probe 96, and secured to apical section 76 of tensioning member 58.

As described above, device 94 is deployed with the help of transapical probe 96 that is configured for use with a surgical robot. In contrast, in some embodiments such as device 110 and as described below, a transapical probe for deploying a device of the present invention is configured for manual use, optionally similarly to known transapical probes.

As described above, second anchor 56 of device 94 is optionally deployed outside the heart in the transverse pericardial sinus. In contrast, in some embodiments such as device 110 and as described below, a second anchor 56 is deployed inside a left atrium 24 on the aortic-mitral curtain portion of the mitral valve annulus.

Various stages of minimally-invasive transapical deployment of device 110 are depicted in FIGS. 8A to 8E.

Figure 8A:
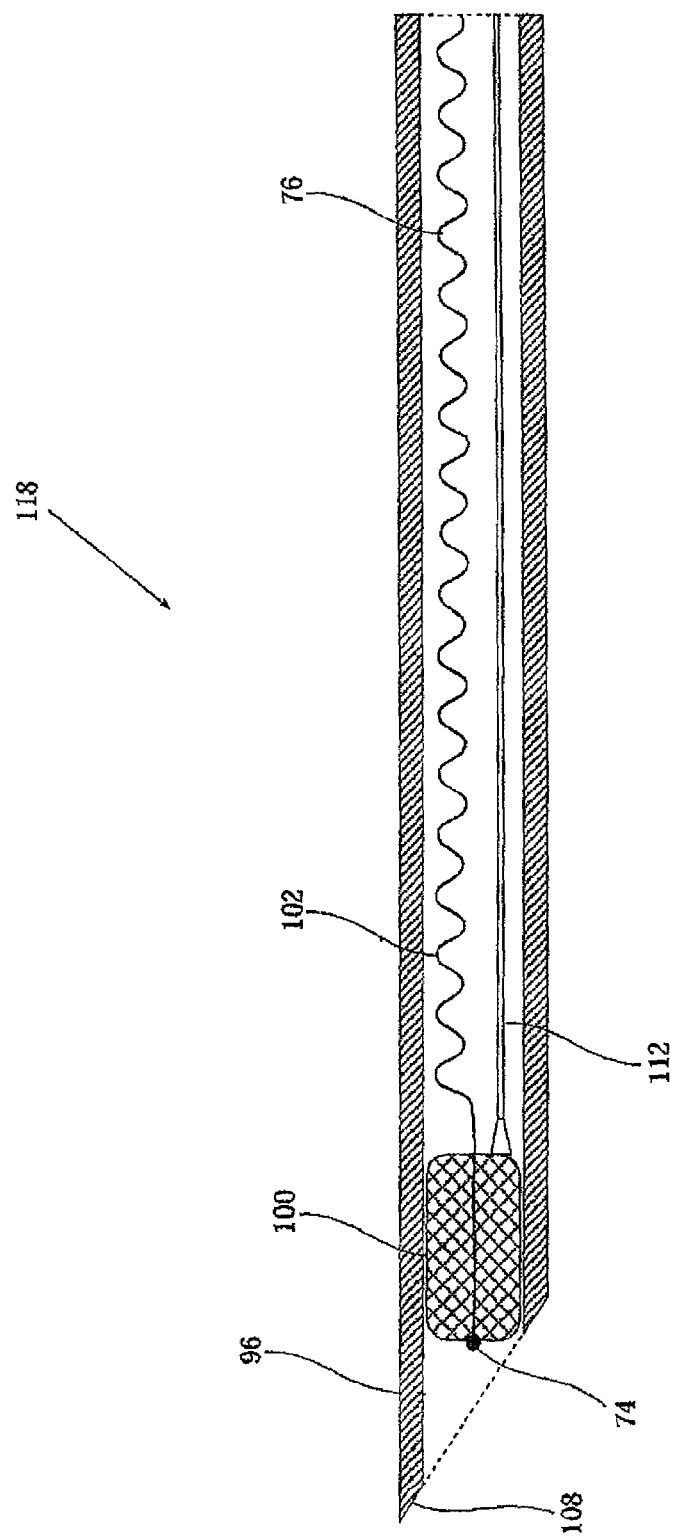
FIGS. 8A-8E depict an embodiment of a device configured for minimally invasive transapical deployment and deployment thereof.

In FIG. 8A, device 110 is depicted packed inside a hollow transapical probe 96 configured for manual use through a left anterior mini thoracotomy procedure, for example, being similarly to known transapical probes, for example as described in PCT patent publications WO 2007/059252 or WO/2007/016187. Inside the bore of transapical probe 96 are seen two components of device 110: a second anchor 56 and a tensioning member 58. Second anchor 56 is substantially a foldable wire mesh configured to self-expand when released from the constraints of the bore of transapical probe 96 analogous to the described above for device 94.

A mitral portion 74 of tensioning member 58, a suture filament, passes into second anchor 56 and is secured (for example by tying or looping) to the mesh making up second anchor 56. An apical portion 76 of tensioning member 58 passes through to the proximal end of transapical probe 96 (not depicted)

As depicted in FIG. 8A, when packed inside transapical probe 96, second anchor 56 is close to piercing tip 104 of transapical probe 96 and in contact with a push rod 106. Push rod 106 passes from the proximal end of transapical probe 96 to contact the proximal side of second anchor 56. Transapical probe 96 is configured to allow actuation of push rod 106 to push second anchor 56 out of transapical probe 96.

A minimally-invasive transapical embodiment of a method for applying pressure to a heart is optionally implemented by deploying device 110 in a heart 50 of a patient.

For deployment of device 110, the patient is optionally prepared in the usual way (e.g., a left anterior thoracotomy) and the piercing tip 104 of transapical probe 96 directed near apex 70 of heart 50 through a portion of external wall 68 that is sagging as a result of a remodeling process. The heart is optionally stopped, however, it is often desirable to not stop the heart and/or not attach the patient to a heart-lung machine.

Figure 8C:
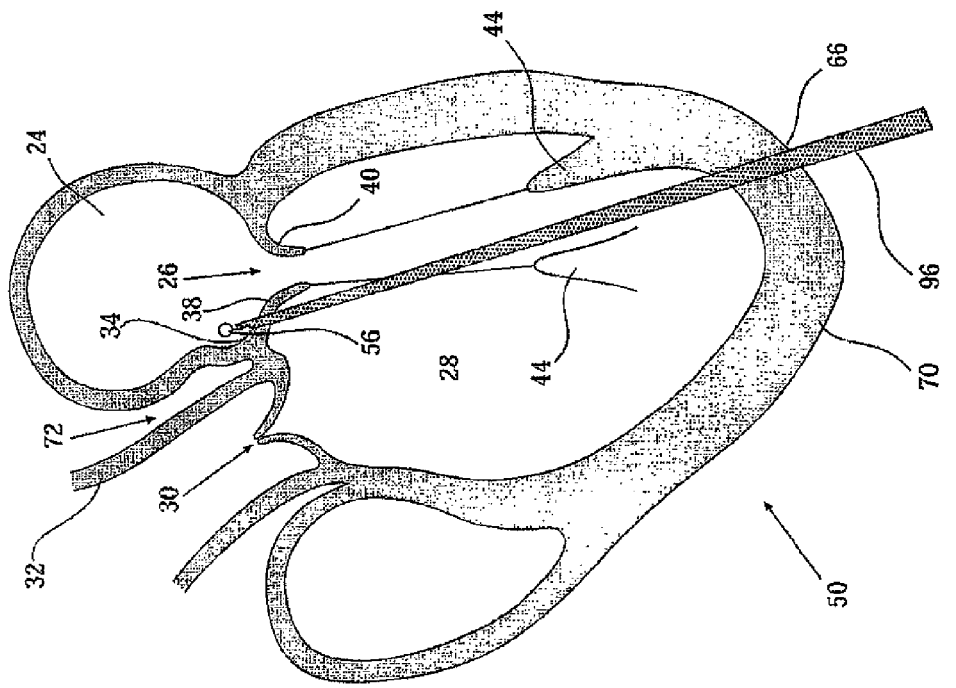
Figure 8B:
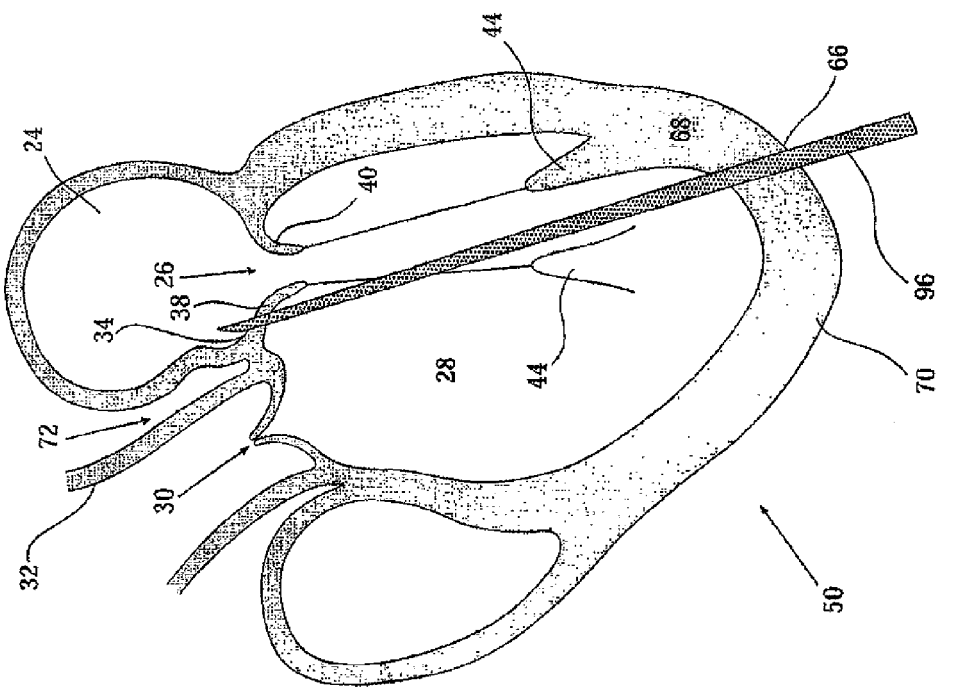

In FIG. 8B, transapical probe 96 is directed so as to pass clear through the base of the heart 28, near or through the fibrotic part of mitral valve annulus 34 and through an annuloplasty ring or band if present, to emerge out into left atrium 24. Optionally, the penetration is in two steps, with a first step being penetrating into the left ventricle, followed by aiming at a desired point in the wall separating the left ventricle from the left atrium. Optionally, the second anchor is deployed inside the wall of the heart, so no penetration into the left atrium is actually provided.

In FIG. 8C, push rod 106 is actuated, pushing second anchor 56 out of the bore of transapical probe 96. Freed of constraints, second anchor 56 expands inside left atrium 24.

Figure 8E:
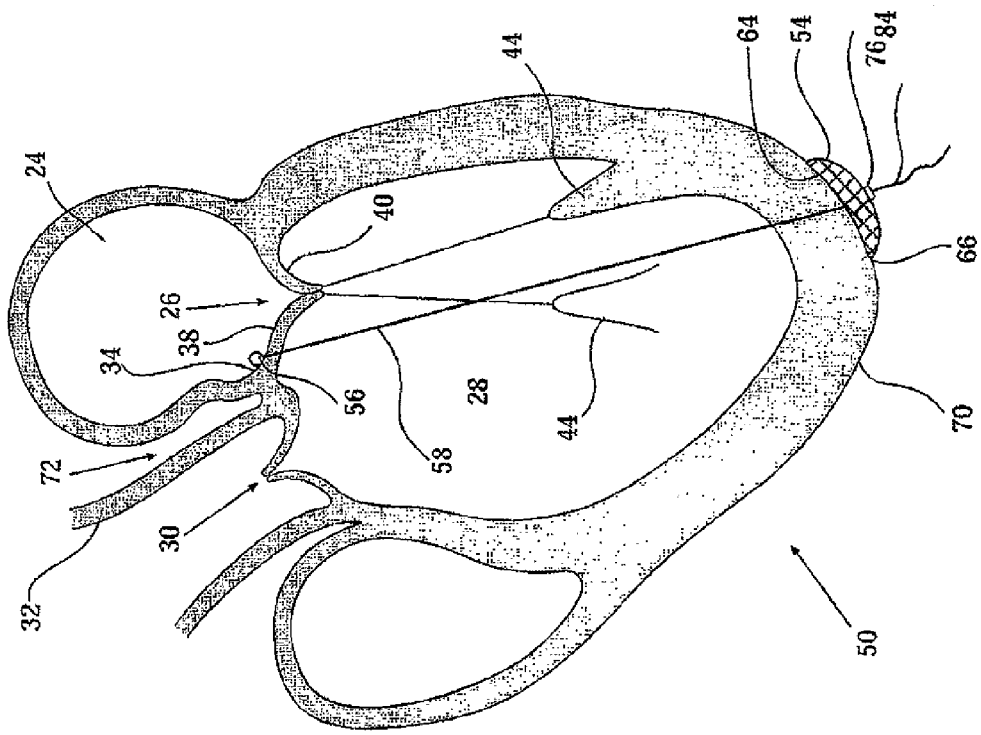
Figure 8D:
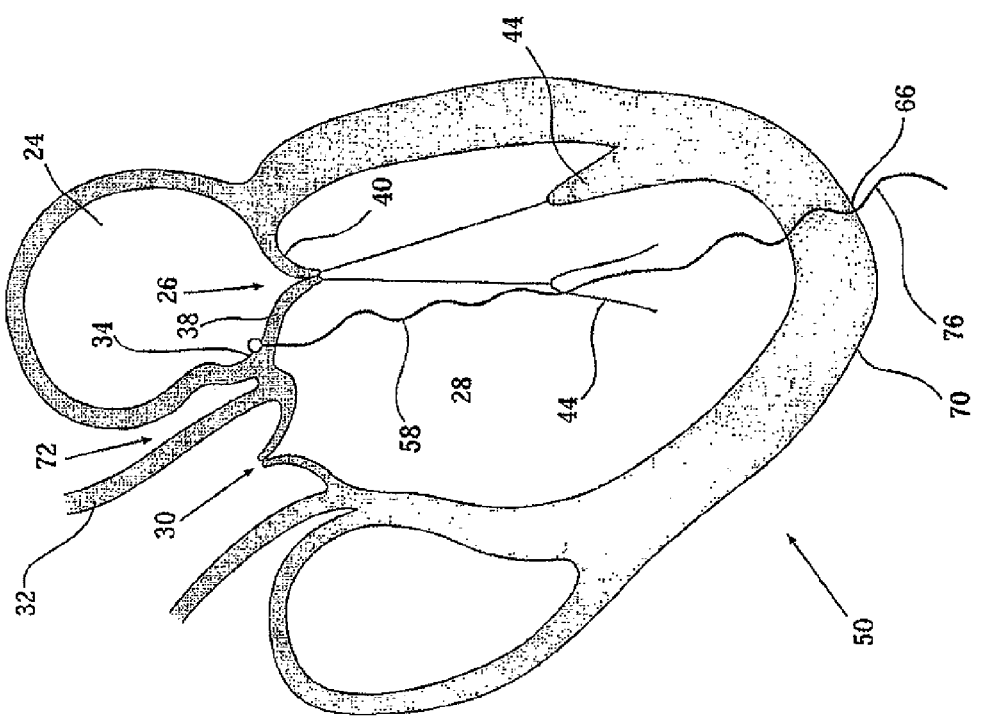

In FIG. 8D, probe 96 is withdrawn from heart 50 and out of the incision in the thorax of the subject, trailing tensioning member 58.

Apical end 76 of tensioning member 58 is trimmed (if desired and/or required), and a first anchor 54 (substantially similar to first anchor 54 described above and depicted in FIG. 6A, is attached thereto, so that a contact face 64 of first anchor 54 contacts surface 66 of heart 50. Analogous to the described above, tensioning member 58 is optionally drawn taut and the tension applied by tensioning member 58 is optionally varied while viewing the magnitude of regurgitation into left atrium during ventricular systole (and/or other cardiac parameter it is desired to change) with an imaging modality in the usual way: the tension is increased to decrease the distance between first anchor 54 and second anchor 56 as defined by tensioning member 58 and the tension is decreased to increase the distance between first anchor 54 and second anchor 56. As the distance is increased or decreased, the change in the structure of mitral valve 26, coaptation and alignment of leaflets 38 and 40 and the degree of regurgitation is monitored until the surgeon performing the deployment of device 110 decides that the length of tensioning member 58 is sufficient. When a given tension provides a desired reduction or elimination of regurgitation into left atrium 24, the length of tensioning member 58 is fixed. Optionally or alternatively, the heart may be stressed (e.g., using pharmaceuticals) and/or its preload and/or afterload changed, to ascertain operational parameters of the device.

The end result is shown in FIG. 8E. It should be noted that the approach direction and/or final layout of the device depend on the desired effect on the heart.

In an exemplary embodiment of the invention, after the patient recovers, heart 50 beats and device 110 functions substantially as described above.

As described above, second anchor 56 of device 110 is configured to be deployed inside the left ventricle, resting against or engaging the aortic-mitral curtain portion of a mitral valve annulus. In some embodiments, a second anchor of a device configured for deployment inside the left ventricle is configured to rest against or engage (e.g., via a hook) an annuloplasty ring and/or suture ring and/or other prosthesis also deployed in the heart, for example, in the left atrium and/or in the coronary sinus (in which case a longer hook may be desired). In some embodiments, an annuloplasty ring may be considered as a portion or an entire second anchor of a device.

In some embodiments, a second anchor of a device configured for minimally invasive deployment inside the left ventricle is configured to rest against or engage an annuloplasty ring deployed in the heart prior to deployment of a device, see, for example, below.

Figure 8F:
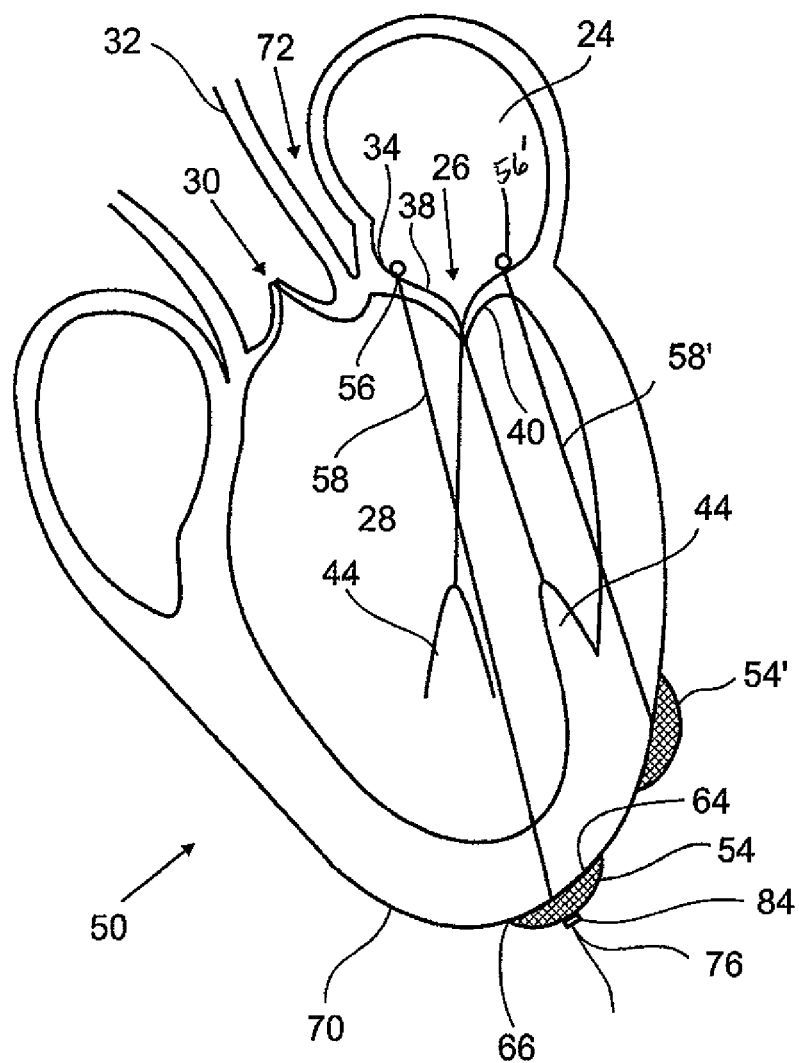
FIG. 8F shows a layout including two devices in a heart, in accordance with an exemplary embodiment of the invention.

FIG. 8F shows an example where a plurality of devices are deployed. A strand 58' is coupled to an outside of the left ventricle via a separate first anchor 54'. A separate second anchor is optionally provided. Optionally, the two first anchors are one large anchor. Optionally, the two devices are deployed at different times. Such a deployment may be practiced with any of the methods/embodiments described herein.

A sixth embodiment of a device of the present invention, device 112, is depicted in FIGS. 9A to 9H. In an exemplary embodiment of the invention, device 112 is configured for transcatheter deployment.

As described above, devices 94 and 110 are configured for deployment with the help of a transapical probe 96 that enters the body through the thorax, for example through a left anterior mini thoracotomy. In contrast, in some embodiments such as device 112 and as described below, a device is configured for deployment by a transcatheter, technique for example that passes through blood vessels to the site of deployment in the heart.

As described above, device 110 includes a second anchor 56 configured for deployment inside a left atrium 24 on the aortic-mitral curtain portion of the mitral valve annulus. Similarly, device 112 includes a second anchor 56 configured for deployment inside a left atrium of a heart. However, unlike second anchor 56 of device 110 that is configured to rest against the aortic-mitral curtain portion of a mitral valve annulus, in some embodiments such as device 112 and as described below, a device is provided with a second anchor that is configured to rest against or otherwise engage a previously deployed implantable prosthesis such as an annuloplasty ring or a prosthetic heart valve.

In an exemplary embodiment of the invention, device 112 is deployed from a base of the heart, and the first (apical) anchor is loaded in a distal part of the delivery system, rather than the second anchors, as described above.

Device 112, as optionally packed in a delivery catheter 114, is depicted in FIGS. 9A and 9B.

Delivery catheter 114 includes a main lumen 116 and a guidewire lumen 118. Inside main lumen 116 are seen components of device 112: a shape memory wire mesh constituting a first anchor 54, a stainless steel hook with base 120 constituting a second anchor 56 (in some embodiments, a different form of second anchor, for example, a rod or folded rod, is provided), a suture filament as a tensioning member 58 and an optional crimpable retainer ring 98. In FIG. 9B, device 112 is depicted released from the constraints of delivery catheter 114. It is seen that, when allowed to expand, first anchor 54 adopts the shape of concave-convex disk with a concave side defining a contact face 64 facing second anchor 56.

An apical portion 76 of tensioning member 58 passes into and is secured (for example by tying or looping) to the first anchor, for example, to a mesh making up first anchor 54. A mitral portion 74 of tensioning member 58 passes through base 120 of second anchor 56. Encircling tensioning member 58 in a proximal direction from second anchor 54 is crimpable retainer ring 98.

In an exemplary embodiment of the invention, as depicted in FIG. 9A, when packed inside delivery catheter 114, first anchor 54 is in contact with a push rod 102. Optionally, push rod 102 passes from the proximal end of delivery catheter 114 (not depicted), to contact the proximal side of first anchor 54. Delivery catheter 114 is configured to allow actuation of push rod 102 to push first anchor 54 out of delivery catheter 114. In an alternative embodiment, push rod 102 is applied to the second anchor and when slightly advanced, only pushes out the first anchor. In an alternative embodiment, the first anchor includes a projection that extends perpendicular to the catheter so that when the catheter is pulled back through cardiac muscle, the projection engages the surrounding tissue and pulls out the first anchor.

As depicted in FIGS. 9A and 9B, crimpable retainer ring 98 is optionally encircled by the jaws of crimper-cutter 108. Delivery catheter 114 is configured to allow actuation of crimper-cutter 108, closing the jaws to crimp crimpable retainer ring 98 around tensioning member 58. When the jaws of crimper-cutter 108 are actuated to close, one or more optional blades inside crimper cutter 108 (not visible in the Figures) cut through a portion of tensioning member 58 that passes therebetween, proximally to crimpable retainer ring 98.

A transcatheter-deployed embodiment of the method of the present invention is optionally implemented by deploying device 112 in a heart 50 of a subject where an annuloplasty ring 80 has been previously deployed as depicted in FIGS. 9C to 9G.

For deployment of device 112, the subject is optionally prepared in the usual way for catheterization, including the optional deployment of a transseptal cannula through the fossa ovalis (not depicted).

A piercing catheter 122 (optionally tip 126, below) is used to pierce a hole through mitral valve annulus 34, near the aortic-mitral curtain touching annuloplasty ring 80. A guidewire 124 is passed through the hole in mitral valve annulus 34 into left ventricle 28 so that the tip of guidewire 124 is in proximity of a selected region of wall 68 of left ventricle 28, FIG. 9C.

Delivery catheter 114 is guided along guidewire 124 into left ventricle 28 to contact wall 68. Piercing tip 126 of delivery catheter 112 is used to pierce through wall 68 of left ventricle 28, FIG. 9D.

In an exemplary embodiment of the invention, one or both penetrations of the heart chamber walls in this and other embodiments is by an externally threaded catheter that is screwed into and through the wall.

Push rod 102 is optionally actuated to push first anchor 54 out from delivery catheter 114. Released form at least some constraints, first anchor 54 expands to an expanded conformation, optionally so that concave contact face 64 faces surface 66 of heart 50, FIG. 9E.

Delivery catheter 114 and guidewire 124 are withdrawn from left ventricle 28, trailing tensioning member 58 that is secured to first anchor 54. When tip 126 of delivery catheter 114 exits left ventricle 28, second anchor 56 is pushed out of delivery catheter 112 using crimper-cutter 108 to engage annuloplasty ring 80, FIG. 9F. Optionally or alternatively, anchor 56 is pulled out by tensioning member 58. Optionally or alternatively, a holder (not shown, for example, a pliers-like jaw or a wire that is hooked onto the anchor and is coupled to the delivery tube, for example, outside the body) is used to prevent premature release of second anchor 56.

Figure 9G:
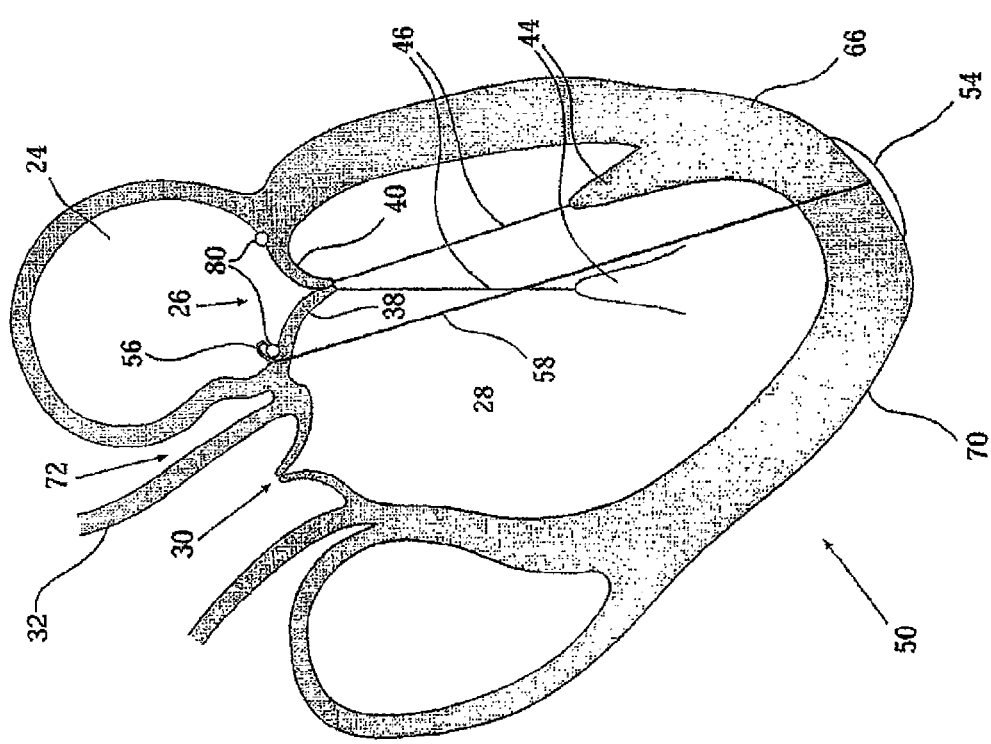

In FIG. 9G, tensioning member 58 is drawn taut while the end of crimper-cutter 108 is pressed against crimpable retainer ring 98 and base 120 of second anchor 56. Optionally, the tension applied by tensioning member 58 is varied while viewing the magnitude of regurgitation into left atrium during ventricular systole with an imaging modality in the usual way: the tension is increased to decrease the distance between first anchor 54 and second anchor 56 as defined by tensioning member 58 and the tension is decreased to increase the distance between first anchor 54 and second anchor 56. As the distance is increased or decreased, the change in the structure of mitral valve 26, coaptation and alignment of leaflets 38 and 40 and the degree of regurgitation is monitored until the surgeon performing the deployment of device 94 decides that the length of tensioning member 58 is sufficient. When a given tension provides a desired reduction or elimination of regurgitation into left atrium 24, crimper-cutter 108 is activated to crimp crimpable retainer ring 98 around tensioning member 58, thereby defining the distance between first anchor 54 and second anchor 56 as well as cutting tensioning member 58, thereby defining the distance between first anchor 54 and second anchor 56 and also cutting through the apical portion 76 of tensioning member 58.

After the patient recovers, heart 50 beats, and device 112 functions as discussed above.

Generally, a delivery catheter such as 114 for deploying a device according to the teachings of the present invention may be configured to pass through the any suitable path through the vasculature of a subject.

In an exemplary embodiment of the invention, a delivery catheter such as 114 is designed to access a left atrium 24 from a right atrium 12 transseptally.

In some embodiments, a delivery catheter such as 114 is designed to access a right atrium 12 using a percutaneous antegrade approach.

In some embodiments, a delivery catheter such as 114 is designed to access a right atrium 12 from the superior vena cava. In some embodiments, a delivery catheter such as 114 is designed to access a superior vena cava from a jugular vein (left or right, preferably right) or a subclavian vein (left or right, preferably right)

In some embodiments a delivery catheter such as 114 is designed to access a right atrium 12 from the inferior vena cava. In some embodiments, a delivery catheter such as 114 is designed to access an inferior vena cava from a femoral vein, for example a left or a right femoral vein.

Reference is now made to FIGS. 10A-10E, which illustrate a guide for a trans-coronary sinus approach, in accordance with an exemplary embodiment of the invention, at various stages of use thereof.

In an exemplary embodiment of the invention, a delivery catheter such as 114 is designed to access the left ventricle via the coronary sinus. FIGS. 10A-11I illustrate a trans-coronary sinus approach which may use a catheter substantially as described in FIGS. 9A-9G. Optionally, an additional element, a coronary sinus guide, is provided, as shown in FIGS. 10A-10E. In an exemplary embodiment of the invention, the guide is used to assist the delivery catheter in exiting the coronary sinus at a desired angle and location to enter the left ventricle. Such a guide may have an addition function of annuloplasty. Optionally, the guide is a standard annuloplasty ring, with hollow sections and/or a guide formed therein, as described below. Optionally, the guide is formed as a spring (e.g., a coil spring). Optionally, the guide is hollow except for a guiding section provided therein and which interferes in part or completely with a catheter inserted into the guide from passing through the guide past the guiding section and/or which guides any such inserted catheter to an aperture at the side of the guide.

Figure 11A:
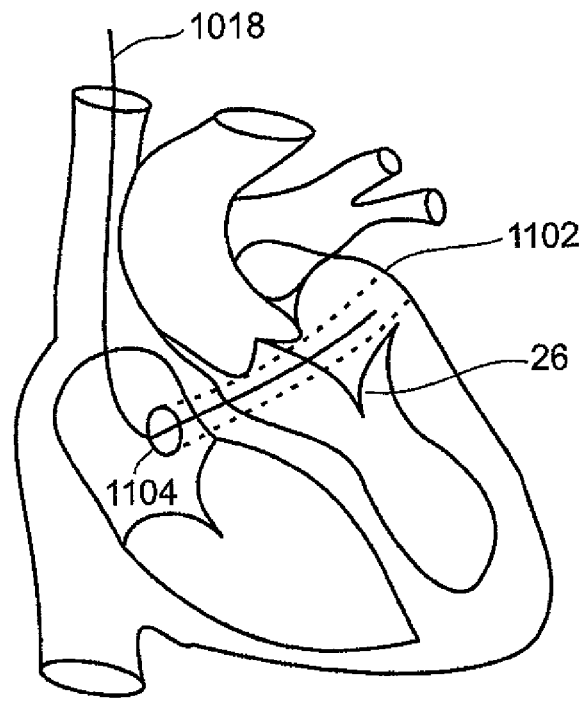
FIGS. 11A-11I illustrate stages in a deployment of a device via a coronary sinus, using a guide according to FIGS. 10A-10E, in accordance with an exemplary embodiment of the invention.
Figure 11B:
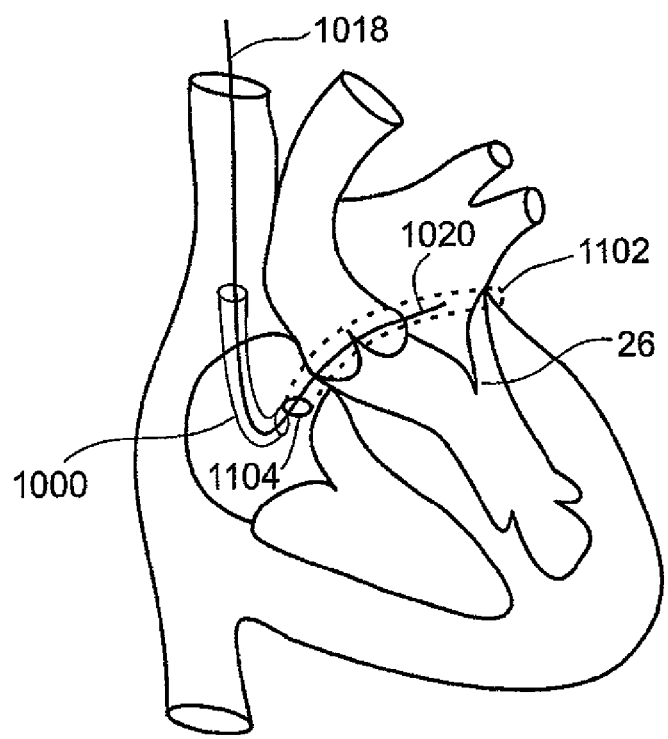
Figure 11C:
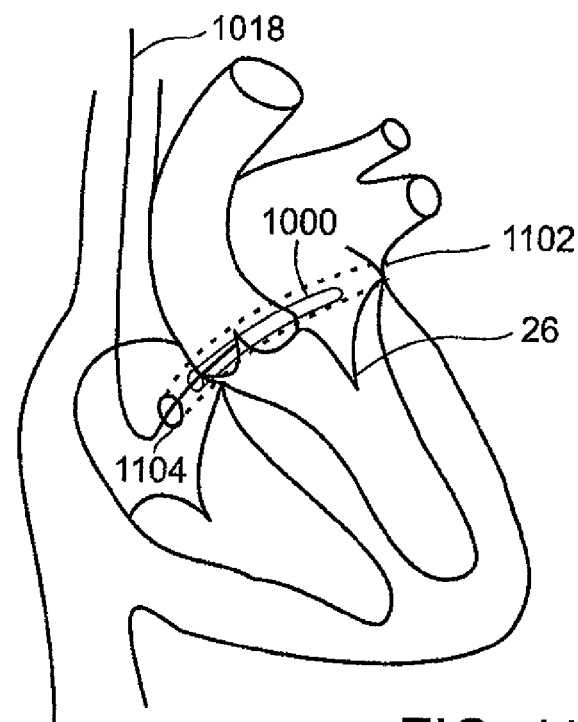
Figure 11D:
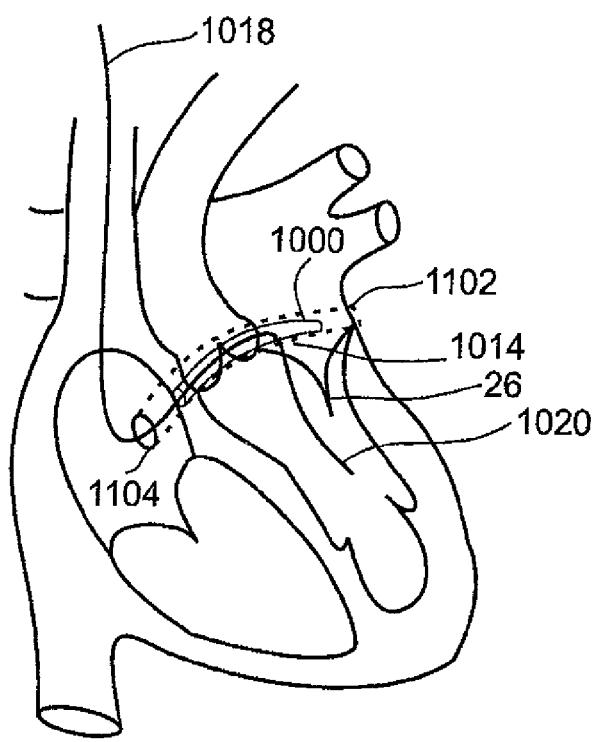
Figure 11E:
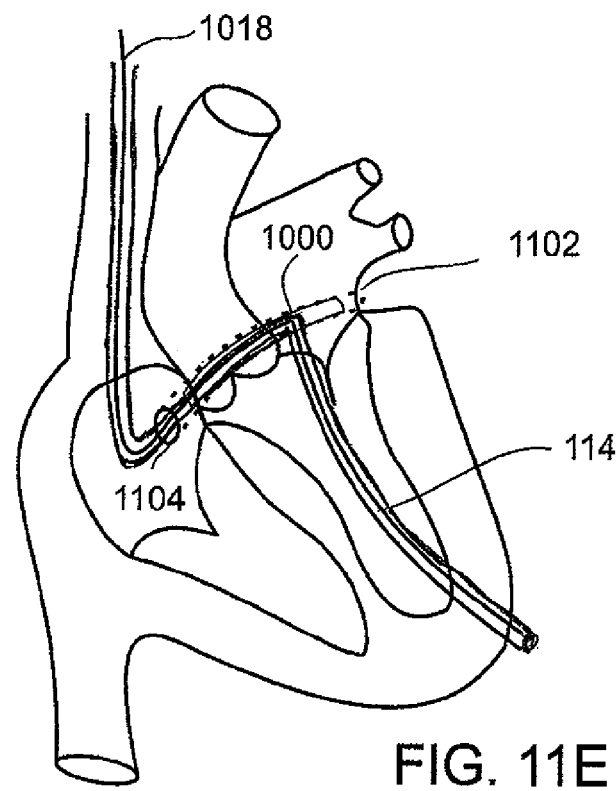
Figure 11F:
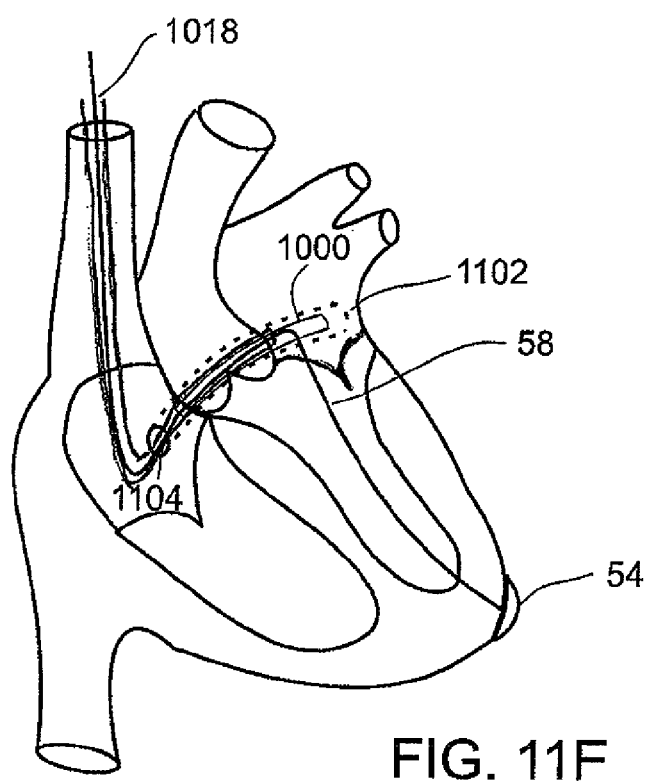
Figure 11G:
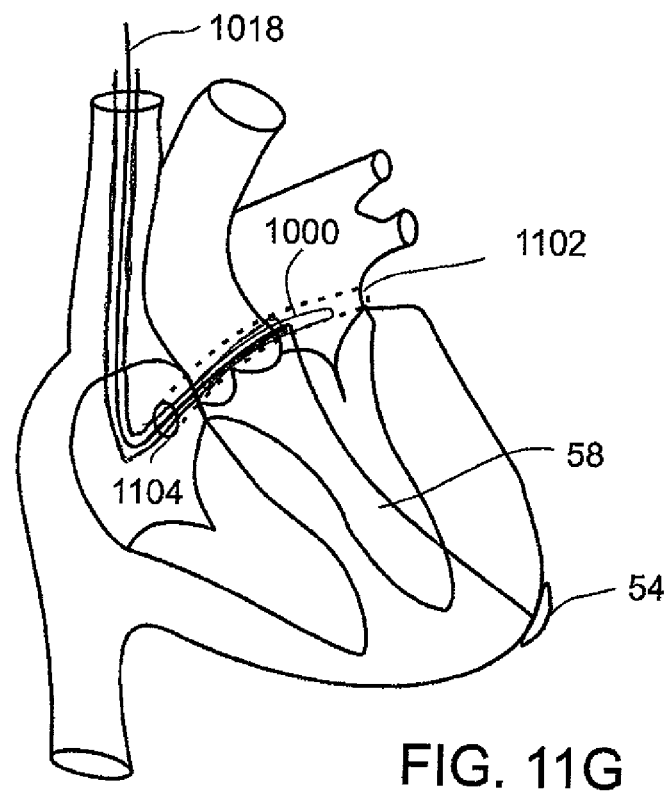
Figure 11H:
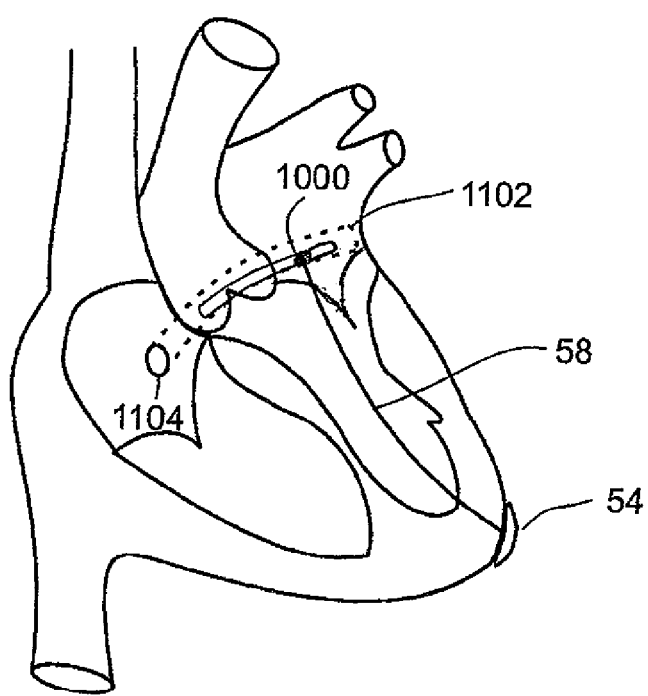
Figure 11I:
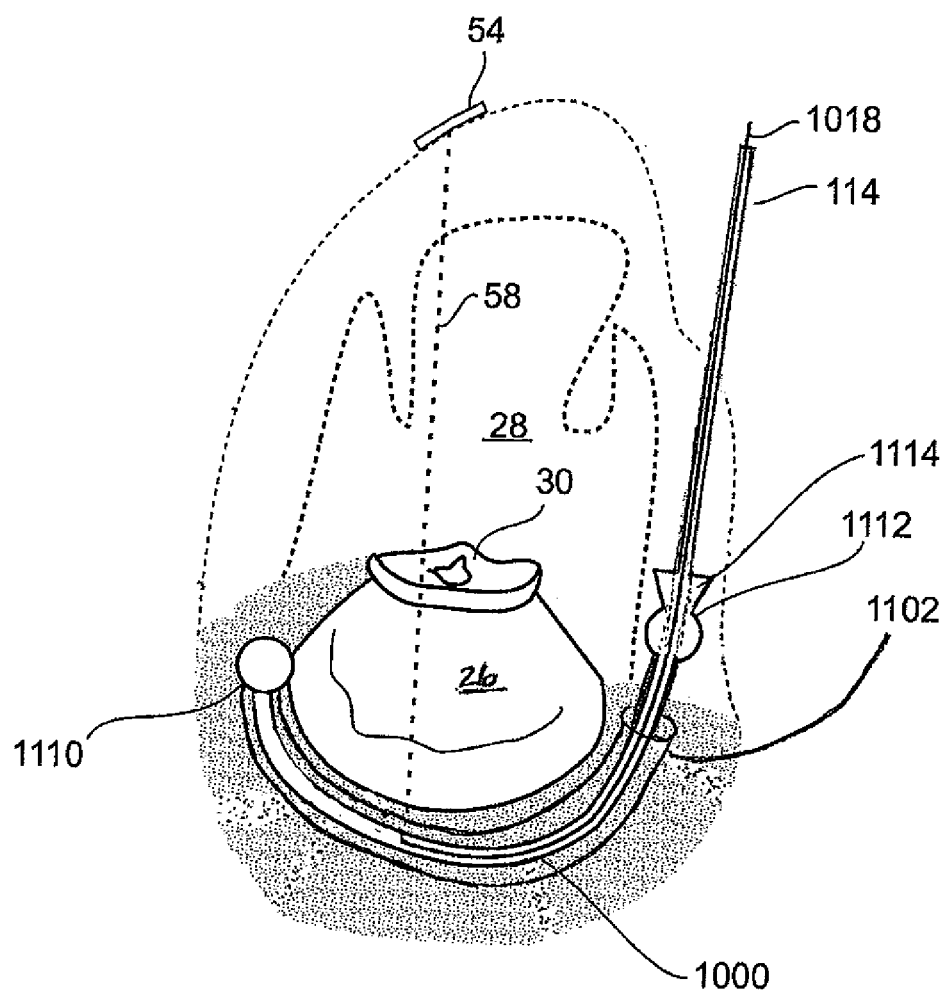

Referring first to FIG. 11I, which shows a schema of an exemplary procedure.

A delivery catheter 114 is shown riding on a guidewire 1018, entering a coronary sinus guide 1000 in the form of a tubular element 1102, exiting the guide at a medial location therealong (or more distally or more proximally, depending on desired anchor location) and laying a tensioning member 58 to a first, apical, anchor 54, with the coronary sinus guide 1000 optionally serving as a second anchor. In the schema shown, the coronary sinus guide 1000 includes both a distal anchoring section 1110, such as a ball and a proximal anchoring section 1112, such as a ball, as known for annuloplasty rings for the coronary sinus. Other anchoring means may be used as well, or omitted. Optionally, a funnel 1114 is provided to help guide catheter 114 and/or guidewire 1018 into the coronary sinus guide 1000. Optionally, catheter 114 in this and/or other embodiments has an outer diameter of 1 mm, 2 mm, 3 mm, 4 mm, 5 mm or smaller, intermediate or larger diameters. Optionally, a trans-apical application tube has an outer diameter (e.g., at point of penetration into the heart) of less than 20 mm, 15 mm, 10 mm, 7 mm, 5 mm, 3 mm, 2 mm or intermediate diameters.

In an exemplary embodiment of the invention, the coronary sinus guide 1000 is small enough in diameter to not cause undue blockage of the coronary sinus, for example, having a diameter of 5.0 mm. In an exemplary embodiment of the invention, the diameter of the guide is decided by the need to cause a bending of more than 60, 70, 80 or even 90 degrees of catheter 114, and the limits of flexibility of such a catheter and/or contents thereof and/or ability of the guide to function as an annuloplasty ring, if desired.

In an exemplary embodiment of the invention, the location of the exit along the coronary sinus guide 1000 depends on the desired effect. Optionally, a plurality of exit points are provided, for example, for providing multiple anchoring locations at different sides of the mitral valve. Such multiple anchoring locations an also be provided in accordance with other embodiments of the invention. In an exemplary embodiment of the invention, the locations are at different points along the annulus of the mitral valve. The first anchor may be located, for example, at the middle of the posterior mitral annulus.

FIGS. 10A-10E illustrate a coronary sinus guide 1000 for a trans-coronary sinus approach, in accordance with an exemplary embodiment of the invention, at various stages of use thereof. While typically not so, the coronary sinus guide 1000 is illustrated as if transparent to make the inner workings clearer.

Figure 10A:
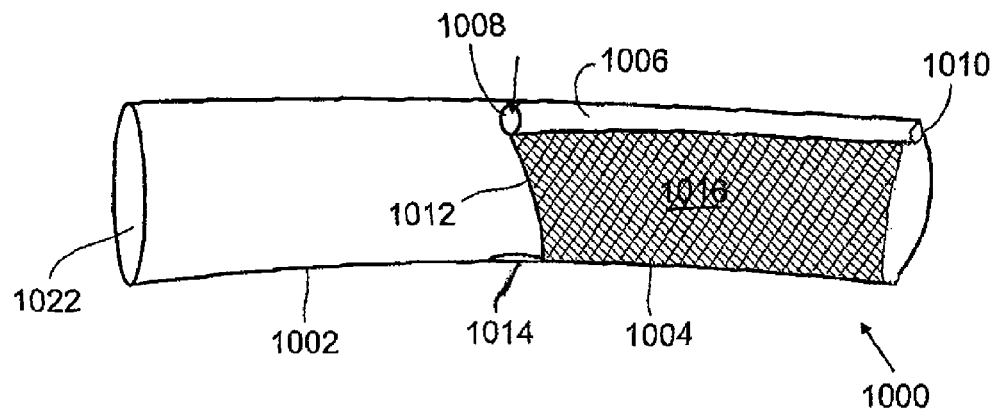
FIGS. 10A-10E illustrate a guide for a trans-coronary sinus approach, in accordance with an exemplary embodiment of the invention, at various stages of use thereof.

FIG. 10A shows a coronary sinus guide 1000, optionally having no moving parts and having the property that a guidewire once retracted therefrom, then pushed back in, will most easily follow a pathway out of a side of the guide, rather than an original axial pathway.

The coronary sinus guide 1000 includes a body having a hollow portion 1002 which communicates with an opening 1022 in a proximal side of the coronary sinus guide 1000 and has a guiding section 1012 which leads to an aperture 1014 in the side of the coronary sinus guide 1000. A far section 1004 past guide 1012 may be, for example, solid (1016), sealed and hollow, or open to the distal side of the coronary sinus guide 1000. In general, however, a catheter inserted through opening 1022 will not be able to reach the far section, due to blocking of guide 1012, for example. Exemplary average diameters of the coronary sinus guide 1000 are less than 20 mm, less than 15 mm, less than 10 mm, less than 5 mm or intermediate diameters. By average diameter is meant a maximum trans-axial dimension averaged over the parts of the device designed for being in the coronary sinus.

In an exemplary embodiment of the invention, the coronary sinus guide 1000 is designed to block less than 80%, 70%, 60%, 45%, 30%, 20% or intermediate percentages of the cross-section of an adult coronary sinus to blood flow.

In an exemplary embodiment of the invention, the coronary sinus guide 1000 is radially collapsible to assist in venous delivery thereof.

In an exemplary embodiment of the invention, a guidewire channel 1006 does communicate between section 1022 and the distal side of the coronary sinus guide 1000, having a proximal opening 1008 and a distal opening 1010.

Figure 10B:
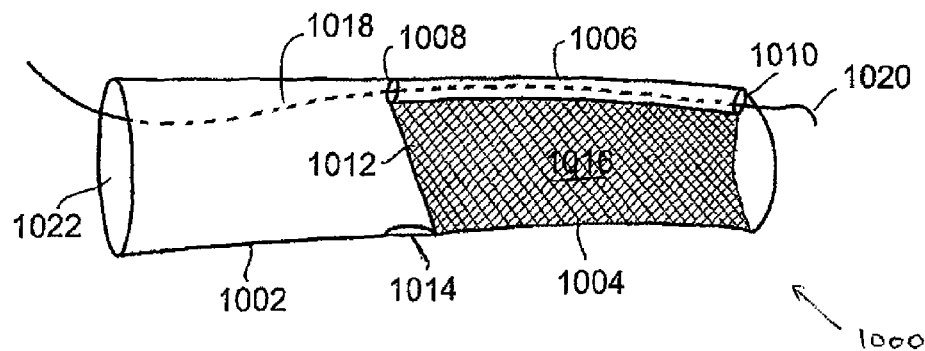

FIG. 10B shows a guidewire 1018 threaded through guidewire channel 1018. Optionally, as shown, guidewire 1018 has a bend 1020 at its tip.

Figure 10C:
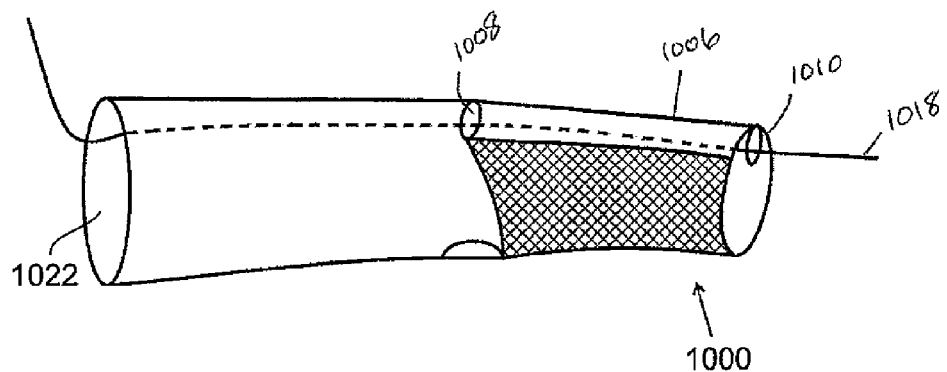

FIG. 10C shows a situation where coronary sinus guide 1000 is not near the tip of the guidewire. The coronary sinus guide 1000 will typically be delivered to the coronary sinus in this condition.

Figure 10D:
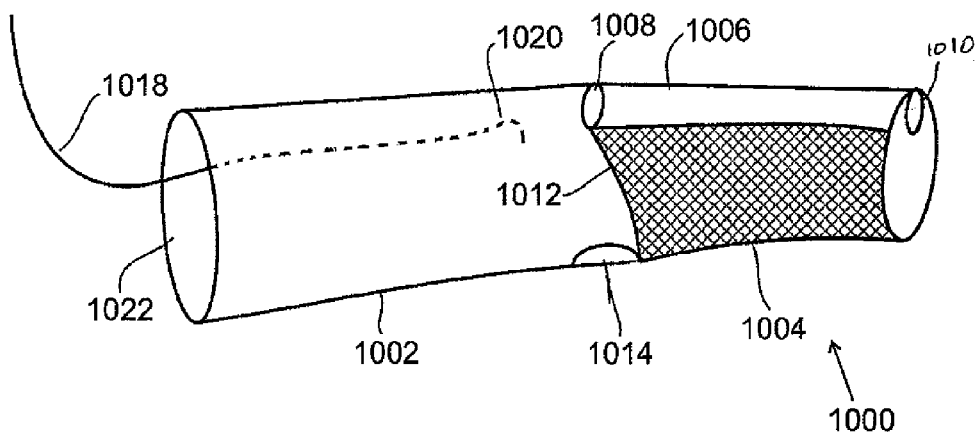

At FIG. 10D, the guidewire is retracted out of guidewire channel 1006 (possibly retracted completely and reinserted into lumen 1022), where it is seen that bend 1020 would interfere with reinsertion of the guidewire into channel 1006. As shown, channel 1006 is continuous with an inner wall of section 1002. Optionally, there is a small bump or step at entrance 1008 to channel 1006. Such an obstacle may interfere with rethreading of guidewire 1018 into channel 1006 even without a bend therein.

Figure 10E:
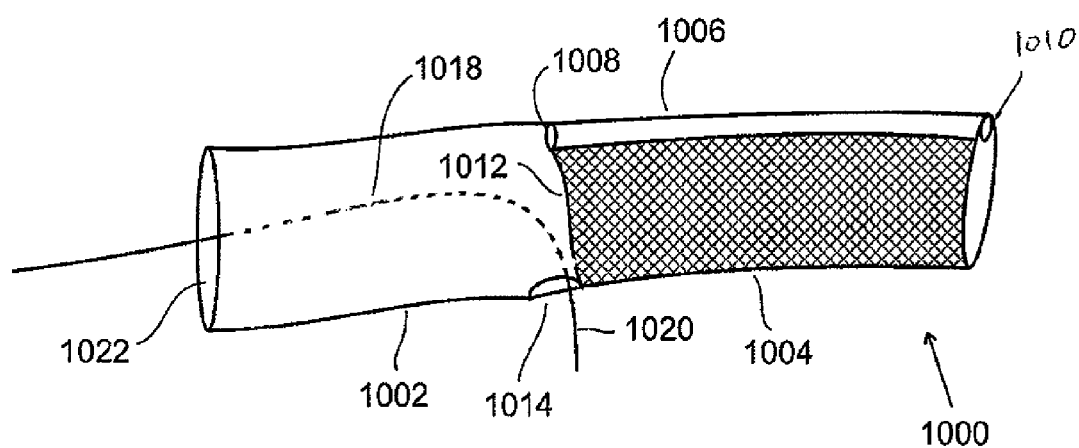

At FIG. 10E, advancement of guidewire 1018 causes it to be guided by guiding section 1012 to exit through aperture 1014 at a desired orientation, position and/or direction into the heart.

FIGS. 11A-11I illustrate stages in a deployment of a device via a coronary sinus, using coronary sinus guide 1000, in accordance with an exemplary embodiment of the invention.

At FIG. 11A, guidewire 1018 (or another guidewire) is brought through the venous system through a coronary sinus osteum 1104 and into a coronary sinus 1102.

At FIG. 11B, coronary sinus guide 1000 is advanced along guidewire 1018 and into the coronary sinus, optionally using a guide catheter (not shown).

At FIG. 11C, coronary sinus guide 1000 is in place and guidewire 1018 is partially retracted (See FIG. 10D).

At FIG. 11D, guidewire 1018 is advanced and guided by coronary sinus guide 1000 into the cardiac wall, which it penetrates. Optionally, the guidewire is replaced before such guiding for a sharp-tipped guidewire. Optionally or alternatively, catheter 114 is advanced along guidewire 1018 and has a sharp tip which provides such penetration ability. Optionally, correct orientation is provided by the location and angle of the hole in the "guide". Optionally, the penetration from aperture 1014 is towards the left ventricle and through muscle, rather than fibrous material. Optionally, coronary sinus guide 1000 is pre-bent, so that when positioned in the coronary sinus it reaches a known shape and orientation relative to the heart.

At FIG. 11E, delivery catheter 114 penetrates (and/or guidewire 1018 is advanced with or before catheter 114 to cause said penetration) the far wall of the left ventricle (or other desired far point).

At FIG. 11F, a first anchor 54 is deployed and catheter 114 retracted, leaving tensioning member 58 in the left ventricle.

At FIG. 11G, the tension in tensioning member 58 is optionally adjusted.

At FIG. 11H, tensioning member 58 is cut to size and locked in place and the guidewire may be withdrawn from the body. In some embodiments, guidewire 1018 serves as tensioning member 58.

As noted above, FIG. 11I shows a schema of the complete exemplary procedure.

In an exemplary embodiment of the invention, coronary sinus guide 1000 serves as a second anchor. Optionally, a bead or rod or other object, having a greatest dimension greater than that of aperture 1014 is advanced along tensioning member 58 and/or fixed thereto, to lock member 58 to coronary sinus guide 1000.

In an alternative embodiment, a second anchor is deployed through aperture 1014 and the coronary sinus guide 1000 is optionally removed (for example if the ring does not act as an annuloplasty ring).

In an exemplary embodiment of the invention, coronary sinus guide 1000 includes multiple (e.g., 2, 3, 4) apertures 1014 and guiding sections 1012 to define multiple exit points, optionally at different orientations (e.g., circumferential positions and/or guide angles relative to axis). Optionally, the apertures and guides are provided at different axial locations and each guide blocks part (e.g., 50%), but not all of the cross-section of section 1002. in use, when a guidewire is advanced, it can be made to engage a guide or go past the guide to a next guide. The sizes of coronary sinus guide 1000 and catheter 114 are optionally selected so that catheter 114 can pass a guide and still be suitably guided by a next guide.

Combining Functionality in One Device

In some embodiments of the invention, guidewire functionality, anchoring functionality, and tensioning member functionality are provided by a device which is inserted into the heart as one device.

Figure 11J:
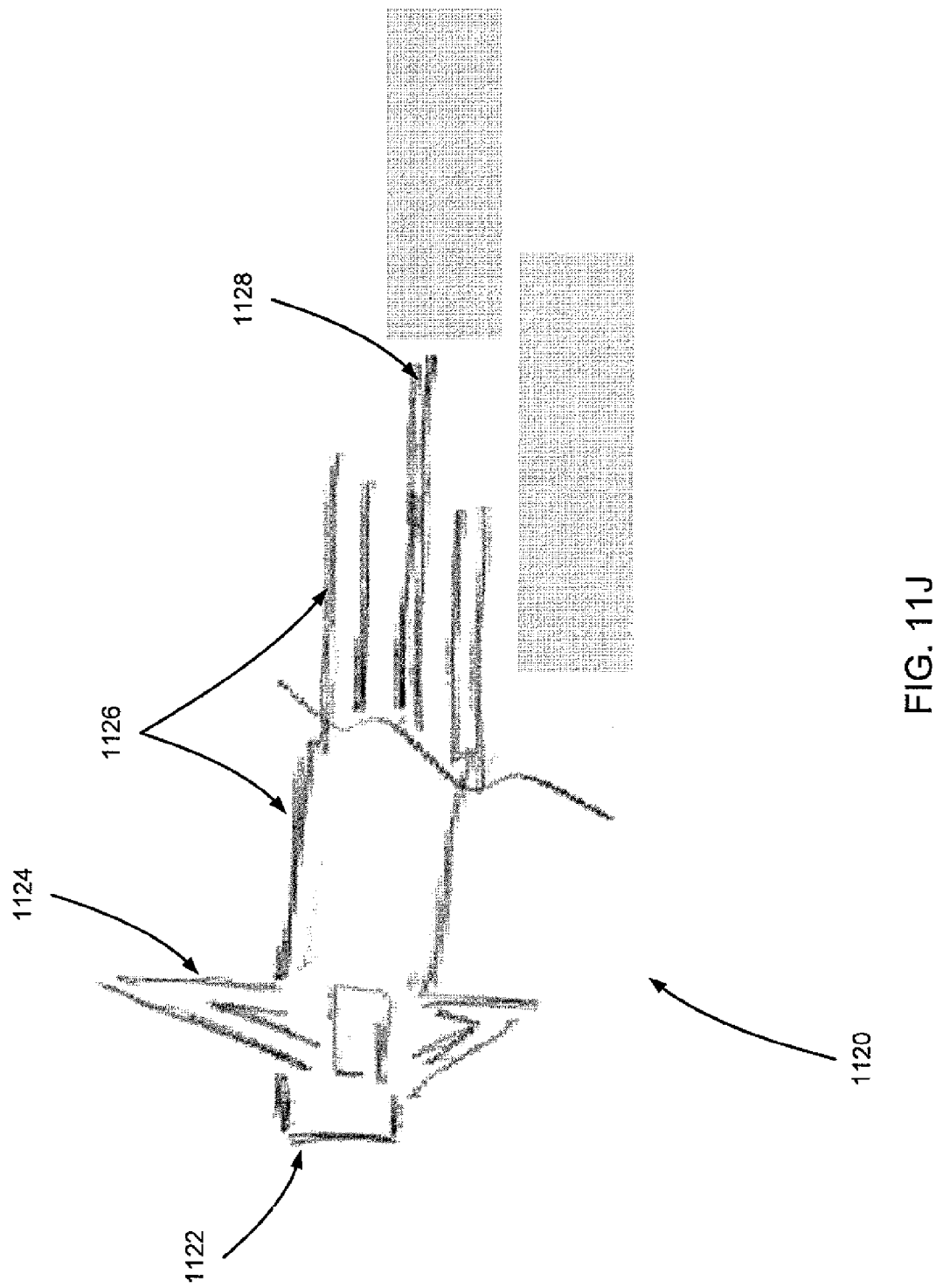
FIG. 11J is a simplified illustration of a section of a multi-functional device providing guidewire, anchoring and tensioning member functionality, in accordance with an exemplary embodiment of the invention.

Reference is now made to FIG. 11J, which is a simplified illustration of a section of a multi-functional device 1120 providing guidewire, anchoring and tensioning member functionality, in accordance with an exemplary embodiment of the invention.

FIG. 11J depicts a section of the multi-functional device 1120, including a tip 1122, foldable anchoring prongs 1124, a delivery tube 1126, and a pull wire 1128 threaded through the delivery tube 1126.

Only a distal section of the multi-functional device 1120 is depicted in FIG. 11J, from which its functioning may be learned. The multi-functional device 1120 is stiff enough for inserting through the body, in approaches such as taught herein.

In some embodiments of the invention the multi-functional device 1120 follows an approach opened by a guide wire. In some embodiments of the invention the tip 1122 is optionally sharp enough to penetrate through tissue, opening the approach for the multi-functional device 1120.

The multi-functional device 1120 is inserted through the body with the foldable anchoring prongs 1124 folded substantially flat against the delivery tube 1126 (FIG. 11J does not depict the foldable anchoring prongs 1124 folded flat). When the tip 1122 of the multi-functional device 1120 reaches an anchoring location (not shown), the tip 1122 is pressed into the anchoring location. The pull wire 1128 is pulled, while the delivery tube 1126 is either pushed or at least held steady. The pull wire 1128 is connected to the tip 1122, and the pulling of the tip 1122 causes the tip to press against the delivery tube 1126, and the foldable anchoring prongs 1124 to open out. The foldable anchoring prongs 1124 open such that they engage tissue, hindering the pulling out of the tip 1122 from the tissue, providing anchoring functionality.

When the anchor has been thus "set", the pull wire 1128 optionally provides tensioning member functionality, as the pull wire 1128 is connected to the anchored tip 1122.

A Coronary Sinus (CS) Ring

In some embodiments of the invention, the coronary sinus guide 1000 of FIGS. 10A-10E and FIGS. 11A-11H is left within the coronary sinus, exerting some force on the coronary sinus, thereby achieving cardiac remodeling.

The coronary sinus guide acting in such capacity will hereby be named a Coronary Sinus (CS) annuloplasty ring, or CS ring. The CS ring is optionally shaped substantially similarly to the shape of the coronary sinus, optionally differing somewhat in shape, so as to exert pressure on sides of the CS and remodel the heart.

The description below shows that the CS ring can be a standard CS ring, a special CS ring designed for guiding coronary sinus wall puncture and/or for tension wire placement procedure, and the CS ring can be a standard CS ring with adaptations made to provide the guiding and/or tension wire placement functionalities.

The CS ring in such an embodiment is shaped so as not to completely obstruct blood flow, since the CS ring is left within the heart.

Materials for producing the CS ring include, by way of a non-limiting example, Nitinol; memory metals which resume their shape over time, thereby resuming a desired shape for exerting cardiac remodeling forces; stainless steel, titanium, and plastics.

In some alternative embodiments of the invention at least part of the CS ring is optionally formed of shape memory material.

In some embodiments of the invention a temperature-induced shape memory material is used to produce at least some of the CS ring, such that the shape memory material returns to its remembered shape at a body temperature of an intended recipient. The CS ring is optionally kept cold before inserting into the recipient's body, and after being in the body for some time, heats to body temperature and changes shape.

In some embodiments of the invention a temperature-induced shape memory material is used, such that the shape memory material returns to its remembered shape at a temperature which is higher than the body temperature of an intended recipient. The CS ring is inserted into the recipient's body, after which a heating device, such as an insulated electric heating coil, heats the temperature-induced shape memory material, which changes shape. The heating device is optionally a catheter or a wire, which is inserted inside, or next to, the shape memory material, and has a heating element or a lumen for heated fluid. The heated fluid is optionally below body-damage temperature, that is, optionally below 42 degrees Celsius or 43 degrees Celsius.

In some embodiments the changed shape is optionally configured to assume a shape substantially conforming to a healthy coronary sinus.

In some embodiments the changed shape is optionally configured to assume a shape which effects a force to reshape the coronary sinus. Optionally, the force is enough to modify a shape of the mitral valve annulus.

Example shapes of the CS ring are described herein with reference to FIGS. 10A-10E, and 12A-12E, 13A-13C, 14A-14C, 15A-15B, 16A-16B, and 17A-17C. Without limiting the generality of the shapes, some example shapes include a solid CS ring, a solid tube, tube sections connected by strips, a mesh tube, a coil, and a spring. The cross section of the shapes may optionally be hollow or not hollow, along some or all of the CS ring. When not hollow, the cross section is shaped so as not to completely obstruct blood flow through the coronary sinus, that is, the cross section does not fill the coronary sinus. When hollow, the hollow may allow blood flow, and/or the hollow may allow wires, catheters, lumens and various devices described herein to pass through.

Example diameters of the cross section of the CS ring include, without limiting generality, a diameter equal to the cross sectional diameter of the coronary sinus, down to a small fraction of the cross sectional diameter of the coronary sinus.

As hearts have different sizes, for example different in children than in adults, in normal hearts than in enlarged hearts, in some animals versus other animals, so the CS ring may optionally be sized to fit a heart for which it is intended.

It is noted that in some embodiments the CS ring provides an annuloplasty function, in some embodiments the CS ring provides an anchoring function, and in some embodiments the CS ring provides both an annuloplasty function and an anchoring function.

In an exemplary embodiment of the invention the coronary sinus guide includes one or more apertures so that, when the coronary sinus guide is in position in the coronary sinus, the apertures are positioned at locations through which punctures are to be made through the coronary sinus wall and into the left atrium and/or left ventricle.

The apertures optionally aim a puncturing device such as a guide wire to the coronary sinus wall.

In an exemplary embodiment of the invention the coronary sinus guide and the one or more apertures are designed so that a tip of a wire and/or tips of wires for puncturing the coronary sinus are guided into the apertures. Optionally, the shape of the coronary sinus guide 1000 assists guiding the tip into the aperture.

Referring again to FIGS. 10A-10E, a procedure is depicted in which the guidewire 1018 is guided into an aperture 1014 in the coronary sinus guide 1000 by the shape of the coronary sinus guide 1000, namely by the guiding section 1012.

The design of the coronary sinus guide 1000 includes the aperture 1014 and the guiding section 1012, is such that a guidewire is guided into the aperture 1014. The guidewire is guided into the aperture 1014 regardless of whether it is the guidewire 1018, just slightly withdrawn from the guidewire channel 1006 of FIGS. 10A-10E and then pushed toward the guiding section 1012; whether it is the guidewire 1018 withdrawn any distance back, including completely withdrawn from a body, and then pushed forward and/or re-inserted into the body and pushed forward; or whether the guidewire is a new guidewire which is not the original guidewire 1018 which was withdrawn from the guidewire channel 1006.

Figure 12A:
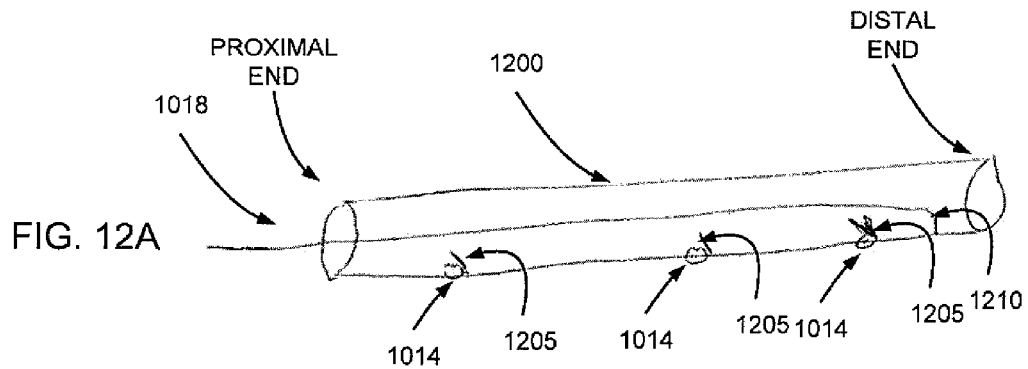
FIGS. 12A-12C illustrate a Coronary Sinus ring, in accordance with an exemplary embodiment of the invention, at various stages of use thereof.
Figure 12B:
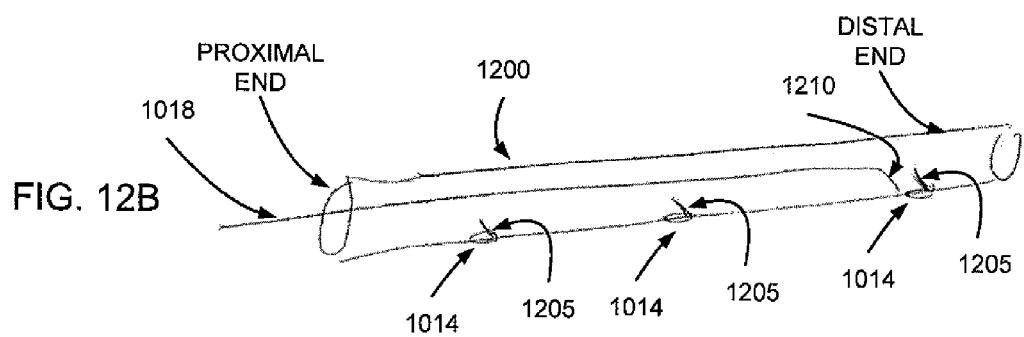
Figure 12C:
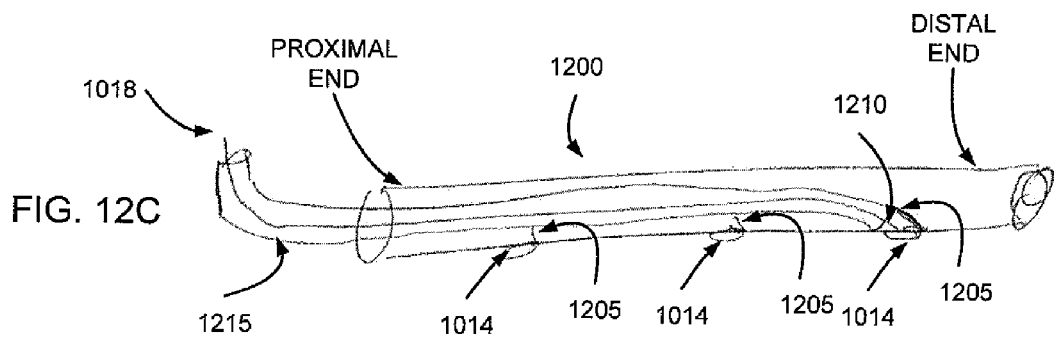

Reference is now made to FIGS. 12A-12C, which illustrate a Coronary Sinus ring 1200, in accordance with an exemplary embodiment of the invention, at various stages of use thereof.

The Coronary Sinus (CS) ring 1200 includes one or more apertures 1014, by way of a non-limiting example, three apertures 1014. Each of the apertures 1014 has a guiding surface 1205 next to it, so that a guidewire 1018 sliding with a tip 1210 next to a wall of the CS ring 1200, will have the tip 1210 guided into the aperture 1014.

The size of the apertures 1014 is designed to allow a puncturing device, and optionally additional devices, through the apertures 1014. A typical diameter of the apertures 1014 can be on the order of 1 mm. A maximum diameter of the apertures optionally does not exceed the diameter of the coronary sinus.

The CS ring 1200 may optionally be placed in the coronary sinus in a standard manner.

The CS ring 1200 may be held in place by its curvature, and/or by its delivery catheter, and/or by a cord attached to the CS ring and optionally controlled from outside the body.

FIG. 12A depicts the guidewire tip 1210 beyond a most distal of the apertures 1014, FIG. 12B depicts the guidewire tip 1210 after being withdrawn behind the most distal of the apertures 1014, and FIG. 12C depicts the guidewire tip 1210 at the most distal of the apertures 1014, optionally puncturing the coronary sinus wall, and optionally with a catheter 1215 slid along the guidewire 1018 and ready to slide through the most distal of the apertures 1014.

The guidewire 1018 may optionally be pulled back as far as needed, and even withdrawn from the body, and then pushed forward to each of the other apertures 1014, for optionally puncturing the coronary sinus wall, and optionally with a catheter 1215 slid along the guidewire 1018 and ready to slide through the apertures 1014.

The CS ring 1200 or just the apertures 1014 of the CS ring 1200, and/or the guidewire tip 1210 optionally have radiation-opaque markers to aid in getting the guidewire tip 1210 right next to an aperture 1014.

In some alternative embodiments of the invention the CS ring 1200 optionally includes shape memory material, for example, as described above in a section referring to the CS ring.

It is noted that the guidewire tip 1210 may not perform the puncturing of the coronary sinus wall, but a device delivered over the guidewire 1018.

The guiding surface 1205 acts as a puncturing device guide, and the term "guiding surface" is used herein to mean "puncturing device guide".

The guidewire tip 1210 is optionally bent as shown in FIGS. 12A-12C, although the bend is not required, and may be absent. An exemplary guidewire 1018 having a bent tip may be a guidewire termed a J-Tip guidewire.

The optional bending of the guidewire tip 1210 is optionally such that the guidewire tip 1210 does not extend across the inside of the CS ring 1200 more than a maximum diameter of the inside, so as not to interfere with pushing the guidewire 1018 through the inside of the CS ring 1200. The optional bending of the guidewire tip 1210 is optionally not too flat, so as not to have the guidewire tip 1210 slide on the apertures 1014. The optional bending is optionally enough to enable positive engagement of the guidewire tip 1210 with the apertures 1014.

In some embodiments of the invention the guiding surface 1205 and/or the aperture 1014 are constructed so as to magnetically attract the guidewire tip 1210. The magnetic attraction is optionally achieved by magnetizing the guidewire tip 1210 and having the guiding surface 1205 and/or the aperture 1014 include a material which attracts a magnet. Alternatively the magnetic attraction is optionally achieved by magnetizing the guiding surface 1205 and/or the aperture 1014, and including a material which attracts a magnet in the guidewire tip 1210.

The magnetic attraction principle is optionally used in embodiments in which a tip of a catheter is attracted to the guiding surface 1205 and/or the aperture 1014.

In some embodiments of the invention the guiding surface 1205 just protrudes from a wall of the CS ring 1200, and substantially does not move relative to the wall of the CS ring 1200.

In some embodiments of the invention the guiding surface 1205 is attached to the wall of the CS ring 1200 by a flexible connection and/or by a hinge. In such embodiments, when the guidewire 1018 is pulled backward and brushes against the guiding surface 1205, the guiding surface 1205 lays substantially flat against the wall of the CS ring 1200; and when the guidewire 1018 is pushed forward and pushes against the guiding surface 1205, the guiding surface 1205 opens to form a guiding angle with the wall of the CS ring 1200.

In some embodiments of the invention, in which the guiding surface 1205 is attached to the wall of the CS ring 1200 by a flexible connection and/or by a hinge, the guiding surface, when open, extends substantially most and/or all of the way across the cross-section of the CS ring 1200.

Figure 12D:
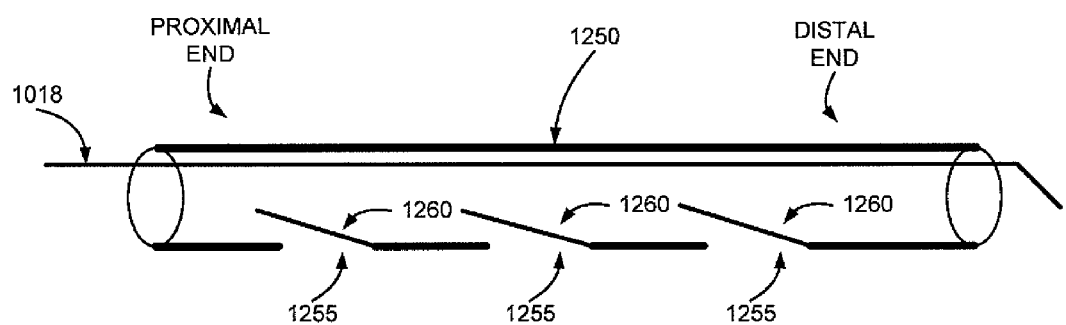
FIGS. 12D and 12E are simplified illustrations of a Coronary Sinus ring 1250, in accordance with an exemplary embodiment of the invention.
Figure 12E:
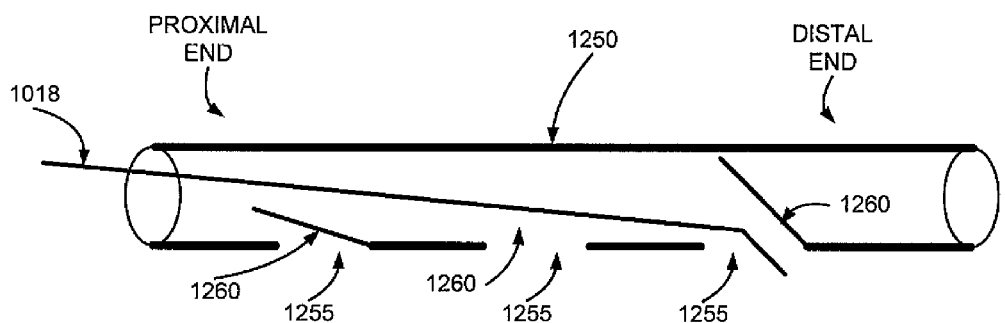

Reference is now made to FIGS. 12D and 12E, which are simplified illustrations of a Coronary Sinus ring 1250, in accordance with an exemplary embodiment of the invention.

FIGS. 12D and 12E depict the CS ring 1250 with several apertures 1255, and flexibly connected guiding surfaces 1260. The connected guiding surfaces 1260 are depicted, by way of a non-limiting example, as connected with hinges 1265.

FIG. 12D depicts the CS ring 1250 with a guidewire 1018 extending beyond a most distal of the apertures 1255, and the guiding surfaces 1260 lie substantially flat against the wall of the CS ring 1250.

FIG. 12E depicts the CS ring 1250 with a guidewire 1018 having been pulled back across the most distal of the apertures 1255, then pushed forward against the most distal of the guiding surfaces 1260, opening the guiding surface 1260 to form a guiding angle with the wall of the CS ring 1250, guiding the guidewire 1018 against the most distal of the apertures 1255. The two non most-distal guiding surfaces 1260 still lie substantially flat against the wall of the CS ring 1250.

In some embodiments of the invention the guiding surfaces 1260 are units which are added to the CS ring 1250, enabling use of the CS ring 1250. Designing the guiding surfaces 1260 to be connected to a standard CS ring enables using a standard, possibly off-the-shelf, CS ring as part of the present invention, and/or adapting a standard, possibly off-the-shelf, CS ring by adding both apertures and guiding surfaces 1260.

In some alternative embodiments of the invention the guiding surfaces 1260 and/or a hinge (not shown) which attaches the guiding surfaces 1260 to the CS ring 1250 optionally include at least some shape memory material.

In some embodiments of the invention a temperature-induced shape memory material is used as part of at least some of the guiding surfaces 1260, such that the shape memory material returns to its remembered shape at a body temperature of an intended recipient. The guiding surfaces 1260 are optionally kept cold before inserting into the recipient's body, and after being in the body for some time, heat to body temperature and changes shape. The pre-change shape optionally keeps the guiding surfaces 1260 against the apertures 1255, optionally not jutting out for guiding. The heated guiding surfaces 1260 change shape and open up the apertures 1255, and/or assume a shape suitable for guiding the guidewire 1018 towards the apertures 1255.

In some embodiments of the invention the shape memory material returns to its remembered shape at a temperature which is higher than the body temperature of an intended recipient. The guiding surfaces 1260 are inserted into the recipient's body, after which a heating device, such as an insulated electric heating coil, heats the temperature-induced shape memory material, which changes shape. The pre-change shape optionally keeps the guiding surfaces 1260 closing the apertures 1255. The heated guiding surfaces 1260 change shape and open up the apertures 1255, assuming a shape suitable for guiding the guidewire 1018 against the apertures 1255.

It is noted that FIGS. 10A-10E, and 12A-12E above, and FIGS. 13A-13C, 14A-14C, 15A-15B, 16A-16B, and 17A-17C below, do not necessarily depict the CS ring curved corresponding to a curvature suitable for their function as an annuloplasty ring. The depiction is simplified, and is not intended to imply a lack of curvature. The CS ring may even extend an arc covering more than 180°. With reference to curvature, it is again noted that the annuloplasty function of the CS ring is optional.

Figure 13A:
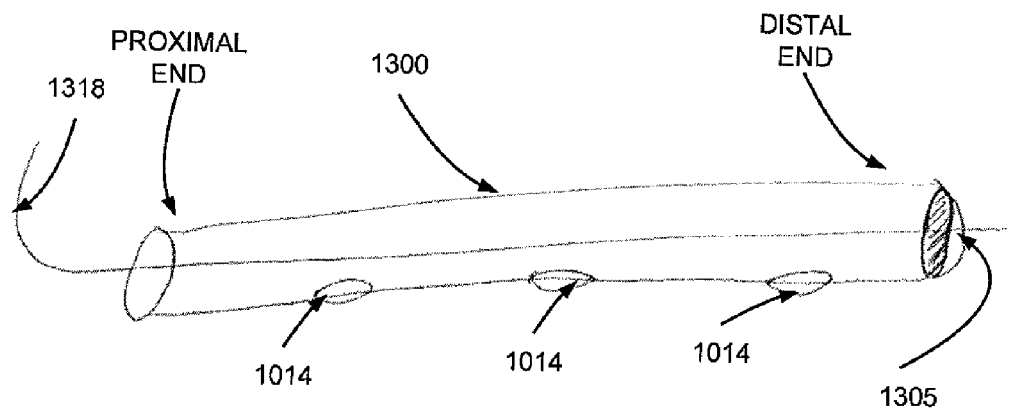
FIGS. 13A-13C illustrate a Coronary Sinus ring, in accordance with an exemplary embodiment of the invention, at various stages of use thereof.
Figure 13B:
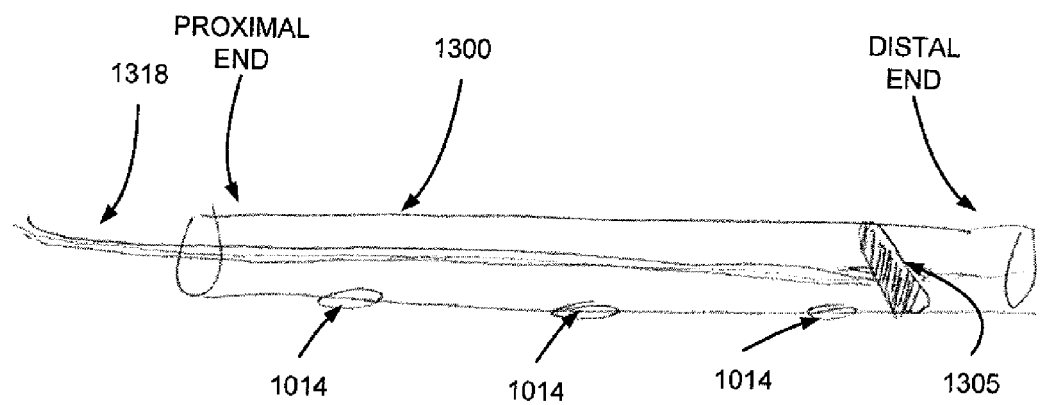
Figure 13C:
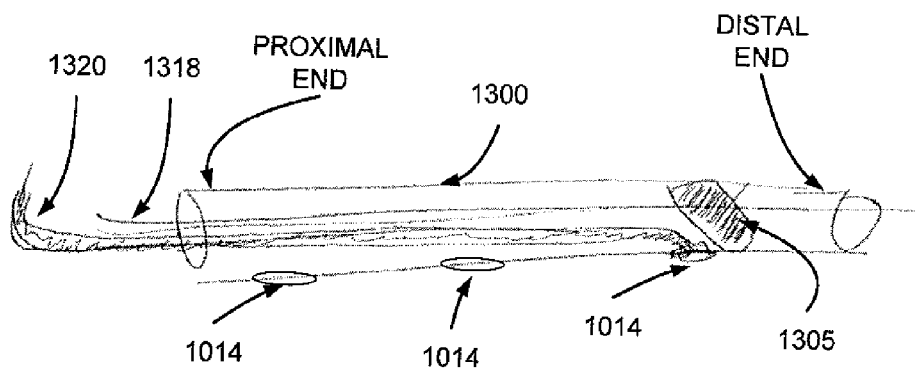

Reference is now made to FIGS. 13A-13C, which illustrate a Coronary Sinus ring 1300, in accordance with an exemplary embodiment of the invention, at various stages of use thereof.

The CS ring 1300 includes one or more apertures 1014. A guide wire 1318 having a guiding surface 1305 runs through the CS ring 1300. The guide wire 1318 may be present in the CS ring 1300 since before being placed in the coronary sinus, or the guide wire 1318 may be slid through the CS ring 1300 after the CS ring 1300 has been placed in the coronary sinus.

The guiding surface 1305 may be part of the guide wire 1318, or the guiding surface 1305 may be a separate unit attached to the guide wire 1318 for a duration of the guiding process.

The guiding surface 1305 may optionally be initially beyond a distal end of the CS ring 1300, or the guiding surface 1305 may be initially within the CS ring 1300, or the guide wire 1318 including the guiding surface 1305 may be inserted into the CS ring 1300 after the CS ring 1300 has been placed in the coronary sinus.

The guide wire 1318 is optionally pulled back, toward the proximal side of the CS ring 1300, pulling the guiding surface 1305 with it. The guiding surface is placed next to one of the apertures 1014, as depicted in FIG. 13B.

The guiding surface 1305 is optionally designed so as to be at the proper angle to guide a guide wire into the aperture 1014.

The guiding surface 1305 may be optionally designed to prevent a guide wire from going past the aperture 1014.

FIG. 13C depicts that when the guiding surface 1305 is properly placed next to an aperture 1014 by the guide wire 1318, an optional additional guide wire 1320 and/or an optional catheter may be pushed along the CS ring 1300 to puncture the coronary sinus wall and optionally insert one or more devices into the heart.

The guiding surface 1305 optionally also guides the one or more devices into the heart.

Achieving the proper angle is optionally done by having the guiding surface 1305 shaped such that within the CS ring 1300 the guiding surface 1305 is always at the proper angle. The proper angle may be achieved, by way of a non-limiting example, by the guiding surface have a cross section, for example oval, corresponding to a cross section of the CS ring 1300, and/or by having the guiding surface 1305 include grooves (not shown), and the CS ring 1300 include corresponding lands (not shown).

In some embodiments of the invention, stopping the guiding surface 1305 right next to an aperture 1014 is optionally aided by imaging the guiding surface 1305 and/or the guide wire 1318. The CS ring 1300 or just the apertures 1014 of the CS ring, and/or the guiding surface 1305 optionally have radiation-opaque markers to aid in stopping the guiding surface 1305 right next to an aperture 1014.

In some embodiments of the invention, stopping the guiding surface 1305 right next to an aperture 1014 is optionally aided by the guiding surface 1305 including one or more protuberances (not shown), and the CS ring 1300 include one or more corresponding depressions (not shown). The guiding surface 1305 thus resists movement at the position of the protuberances, yet may optionally be pulled along by applying more force.

The protuberances may optionally act as small guiding surfaces, having a suitable angle in a direction of approach of the guidewire 1318 to function as small guiding surfaces.

The protuberances and depressions may optionally be used to achieve a proper location for the guiding surface 1305 next to the apertures 1014.

In some embodiments of the invention the guiding surface 1305 is part of a balloon, which is inflated so as to stop next to an aperture 1014.

In some embodiments of the invention the guiding surface 1305 is part of an expandable unit, which is expanded so as to stop next to an aperture 1014.

It is noted that the guiding surface may optionally block flow of blood through the CS ring 1300, at least if inflated/expanded. It is noted that the CS ring 1300, within which the guiding surface is optionally placed, may or may not be blocking flow of blood through the coronary sinus.

Figure 14A:
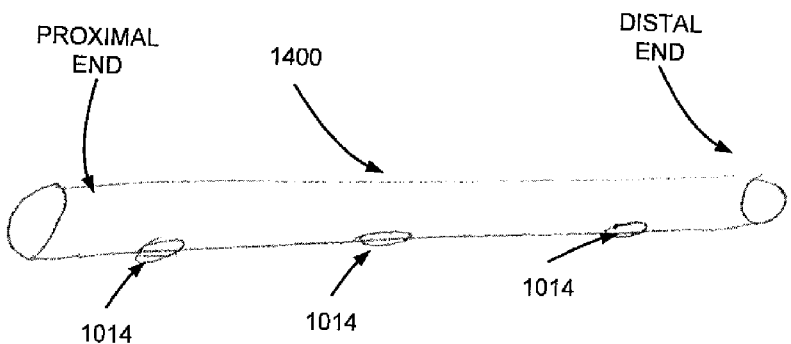
FIGS. 14A-14C illustrate a Coronary Sinus ring, in accordance with an alternative exemplary embodiment of the invention, at various stages of use thereof.
Figure 14B:
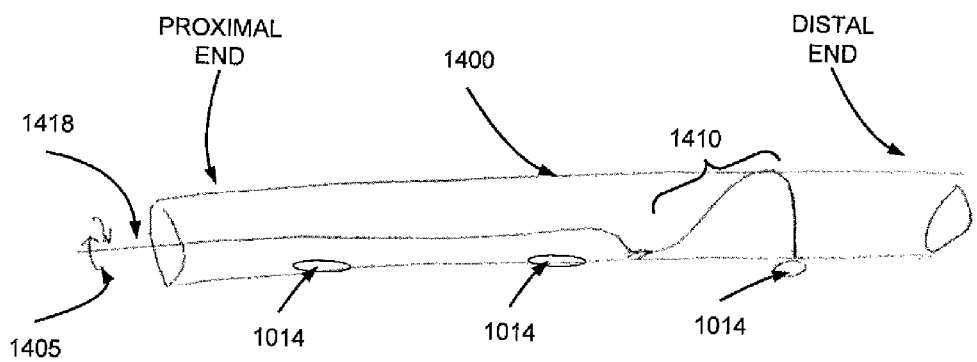
Figure 14C:
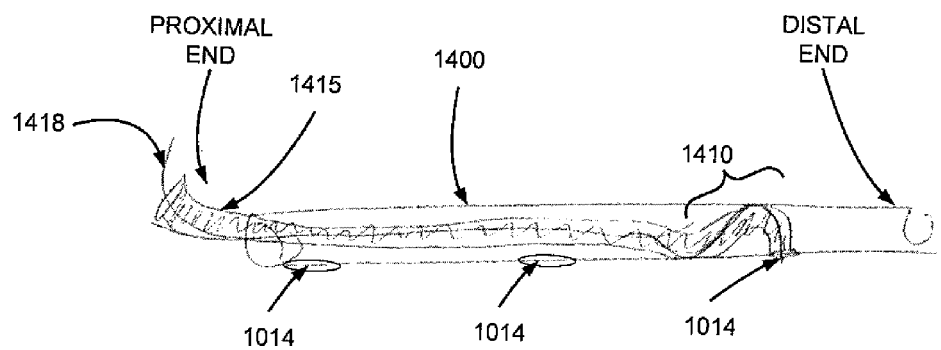

Reference is now made to FIGS. 14A-14C, which illustrate a Coronary Sinus ring 1400, in accordance with an alternative exemplary embodiment of the invention, at various stages of use thereof.

The CS ring 1400 includes one or more apertures 1014, similarly to the apertures 1014 of FIGS. 13A-13C, as depicted in FIG. 14A.

A guide wire 1418 is optionally placed in the CS ring 1400, with a tip 1410 next to one of the apertures 1014, as depicted in FIG. 14B. The tip 1410 is shaped as a spring, exerting some force on walls of the CS ring 1400. When guide wire 1418 is optionally rotated 1405, the tip 1410 is also optionally rotated, and the tip 1410 fits into the aperture 1014. The guide wire 1418 may also be slid slightly forward and back to aid the tip 1410 find the aperture 1014.

FIG. 14C depicts that when the tip 1410 is properly placed next to an aperture 1014 by the guide wire 1418, the tip may be pushed to puncture the coronary sinus wall, and an optional catheter 1415 may be pushed along the guide wire 1418 in order to optionally insert one or more devices into the heart.

In some embodiments of the invention the tip 1410 may be a J-Tip.

In some embodiments of the invention the tip 1410 may be S-shaped.

Figure 15A:
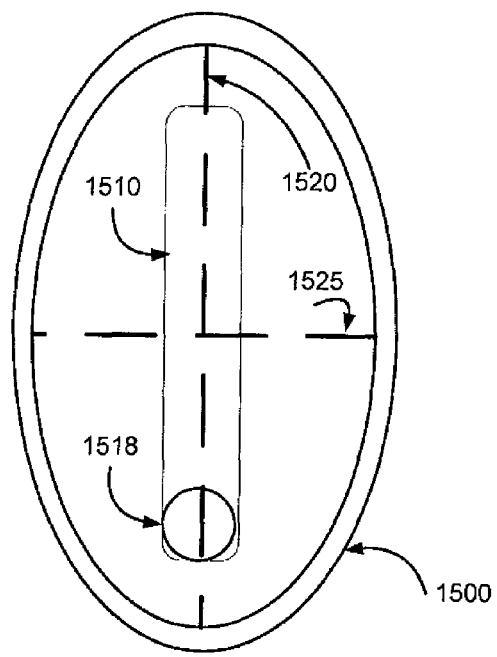
FIGS. 15A-15B illustrate a Coronary Sinus ring, in accordance with an alternative exemplary embodiment of the invention, at various stages of use thereof.
Figure 15B:
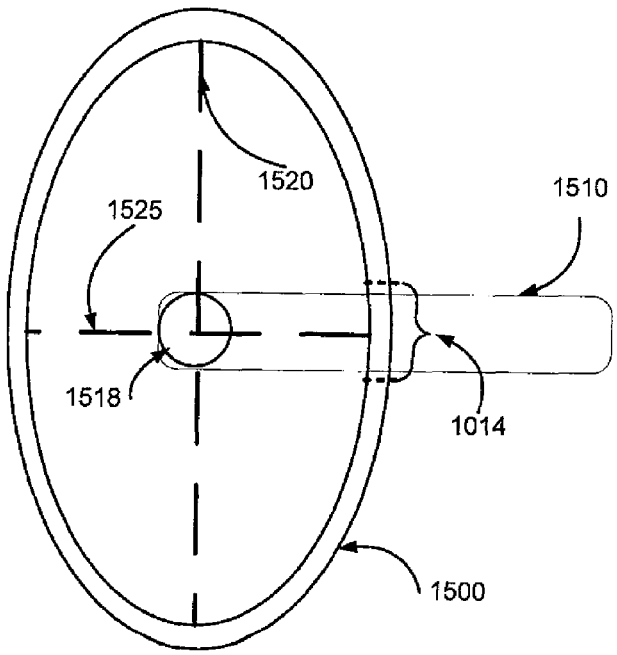

Reference is now made to FIGS. 15A-15B, which illustrate a Coronary Sinus ring 1500, in accordance with an alternative exemplary embodiment of the invention, at various stages of use thereof.

FIGS. 15A-15B are depicted as a simplified cross-sectional view of the CS ring 1500, including one or more apertures 1014, and a simplified cross sectional view of a guide wire 1518 and a guide wire tip 1510.

The cross-section of an inside of the CS ring 1500, at least in proximity to an aperture 1014, includes a shorter diameter 1520 across from the aperture 1014 and a longer diameter 1525 perpendicular to the aperture 1014. The guide wire 1518 and the guide wire tip 1510 may be slid freely along the CS ring 1500 when the guide wire tip 1510 is parallel to the longer diameter 1525 as depicted in FIG. 15A.

When the guide wire 1518 and the guide wire tip 1510 are rotated, the guide wire tip 1510 becomes parallel to the shorter diameter 1520, and optionally protrudes from the aperture 1014, and optionally exerts force on the coronary sinus wall (not shown) through the aperture 1014.

Figure 16A:
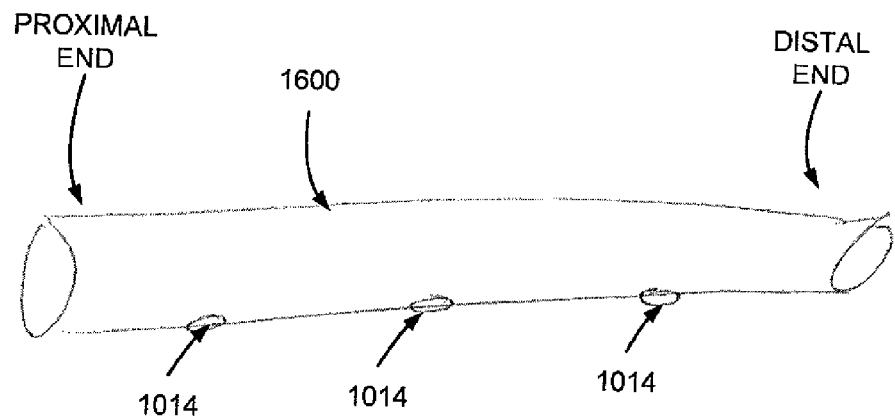
FIGS. 16A-16B illustrate a Coronary Sinus ring, in accordance with an alternative exemplary embodiment of the invention, at various stages of use thereof.
Figure 16B:
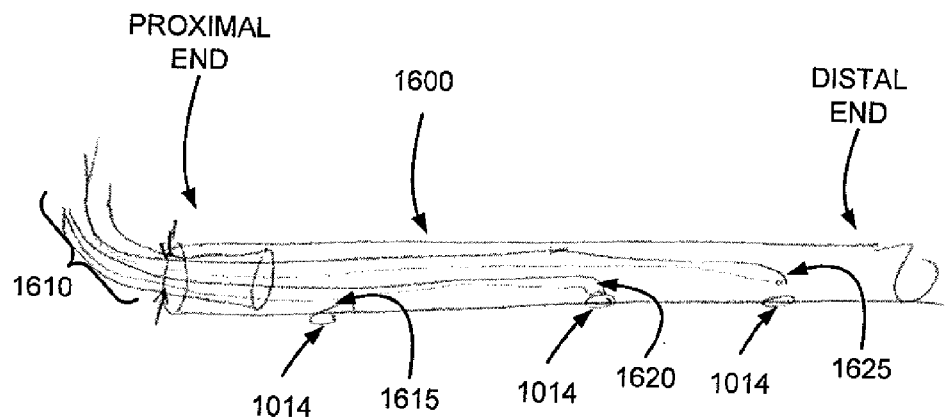

Reference is now made to FIGS. 16A-16B, which illustrate a Coronary Sinus ring 1600, in accordance with an alternative exemplary embodiment of the invention, at various stages of use thereof.

The CS ring 1600 optionally includes one or more apertures 1014, similarly to the apertures 1014 of FIGS. 13A-13C, and 14A-14C, as depicted in FIG. 16A.

The CS ring 1600 may be a standard CS ring or coil, having apertures as part of the standard and/or added to the standard, and the multiple lumens described below offer access to multiple apertures.

A multi-lumen catheter 1610 is placed in the CS ring 1600. As described above, the multi-lumen catheter 1610 may be placed in the CS ring 1600 prior to inserting the CS ring 1600 into the coronary sinus, or the multi-lumen catheter 1610 may be placed in the CS ring 1600 after inserting the CS ring 1600 into the coronary sinus.

By way of a non-limiting example, the multi-lumen catheter 1610 includes three lumens, a first lumen 1615, a second lumen 1620, and a third lumen 1625.

The lumens are optionally placed with openings at desired distances from each other, and optionally aligned with the apertures 1014, as depicted in FIG. 16B.

In an embodiment in which the lumens are placed inside the CS ring 1600 before placing the CS ring 1600 in the coronary sinus, correspondence of the openings of the lumens to the apertures 1014 is easily understood.

In an embodiment in which the lumens are placed inside the CS ring 1600 after placing the CS ring 1600 in the coronary sinus, correspondence of the openings of the lumens to the apertures 1014 is achieved by sliding the lumens, together and/or separately, within the CS ring 1600.

It is noted that the multi-lumen catheter may optionally serve for delivering multiple wires which engage the walls of the coronary sinus and anchor the CS ring to the coronary sinus.

Reference is now made to FIGS. 17A-17C illustrate a Coronary Sinus ring 1700, in accordance with an alternative exemplary embodiment of the invention, at various stages of use thereof.

The CS ring 1700 may be a standard CS ring or coil, having apertures as part of the standard and/or added to the standard, and the multiple lumens described below offer access to multiple apertures.

FIGS. 17A-17C depict the CS ring 1700 optionally shaped as a spring 1705, optionally attached to a strip 1710, as depicted in FIG. 17A. One potential advantage of a spring shape is that the spring shape interferes less with blood flow than a pipe shape. Other potential advantages include the spring shape optionally being self expanding, and optionally using less material.

The strip 1710 optionally provides a curvature suitable for the coronary sinus, and the spring 1705 optionally keeps the coronary sinus from collapsing in diameter when force is exerted to shape it.

In some alternative embodiments of the invention the CS ring 1700 optionally includes shape memory material, for example, as described above in a section referring to the CS ring.

In some alternative embodiments of the invention the strip 1710 includes the shape memory material.

In some alternative embodiments of the invention the spring 1705 includes the shape memory material.

In some alternative embodiments of the invention both the strip 1710 and the spring 1705 include the shape memory material.

In some alternative embodiments of the invention both the strip 1710 and the spring 1705 are optionally made of the shape memory material, with some parts treated differently than others, to provide shape memory to the some parts.

The CS ring 1700 includes one or more apertures 1014.

FIG. 17B depicts a guide wire 1718 and a multi-lumen catheter 1610 placed within the CS ring 1700. As described above, the guide wire 1718 and a multi-lumen catheter 1610 may placed within the CS ring 1700 prior to placing the CS ring 1700 within the coronary sinus, or the guide wire 1718 may guide the multi-lumen catheter 1610 to be placed within the CS ring 1700 after the CS ring 1700 is placed within the coronary sinus.

FIG. 17C depicts the guide wire 1718 and the multi-lumen catheter 1610 without depicting the CS ring 1700, as if the CS ring 1700 isn't there. FIG. 17C is a simplified depiction intended to depict different lumen openings at different lengths, corresponding to apertures 1014 of the CS ring 1700.

It is noted that the CS rings of FIGS. 16A-16B and 17A-17C may also optionally use protuberances and/or depressions to guide lumen placement.

In some embodiments of the invention the CS ring is an off-the-shelf CS ring adapted for guiding a guide wire into one or more apertures. Several non-limiting examples of such embodiments are provided below.

In one embodiment the CS ring 1700 of FIG. 17A may optionally be an off-the-shelf CS ring with three apertures drilled in the strip 1710.

In another embodiment the CS ring 1700 of FIG. 17A may optionally be an off-the-shelf CS ring with a spring shape, and location of one or more punctures may be the location of openings of the multi-lumen catheter, optionally positioned so that the openings correspond to spaces in the spring.

In yet another embodiment any CS ring having apertures in its sides may be used, optionally together with a multi-lumen catheter.

In still another embodiment the CS ring 1700 of FIG. 17A may optionally be an off-the-shelf CS ring with a spring shape, and one or more punctures may performed by tracking a guide wire tip through imaging, and puncturing through spaces in the spring shape.

Following are exemplary protocols for treatment, in accordance with some exemplary embodiments of the invention.

Apical Approach when Used for Ischemic MR (i) After anesthesia with a double lumen tube, a small left anterior thoracotomy is made.

(ii) The left lung is deflated and the Pericardium is exposed.

(iii) The pericardium is opened and the adhesions around the bulging myocardium are cut.

(iv) Under TEE guidance the device is inserted into the left ventricle and advanced so its tip penetrates through the Mitral annulus and just above an optional annuloplasty ring.

(v) The Annular anchor is opened and the device is pulled back out of the LV.

(vi) The second (apical) anchor is now opened.

(vii) The distance between the two anchors is now gradually shortened along the tension member until a desired Mitral leaflets coaptation is achieved.

(viii) The anchor is secured in place to the tension member and the excess external tension member is cut short.

(ix) The thoracotomy is closed after a drain is positioned.

Apical Approach when Used for Cardiomyopathy (i) After anesthesia with a double lumen tube, a small left anterior thoracotomy is made.

(ii) The left lung is deflated and the Pericardium is exposed.

(iii) Under TEE guidance the first device is inserted into the left ventricle (not necessarily at the apex) and advanced so its tip penetrates through the Mitral annulus and just above the annuloplasty ring.

(iv) The Annular anchor is opened and the device is pulled back out of the LV.

(v) The external (possibly apical) anchor is now opened.

(vi) A second (and third if needed) device is now applied with same technique at different points as planned according to the shape of the heart.

(vii) The distance between the coupled anchors is now gradually shortened along the tension members until the desired LV shape is achieved.

(viii) The anchors are secured in place to the tension members and the excess external tension members are cut short.

(ix) The thoracotomy is closed after a drain is positioned.

Catheter Approach when Used for Ischemic MR (i) A leading guidewire is inserted through the femoral or jugular vein (or any other big vein). Under TEE guidance the wire with the device is advanced to the right atrium and through the atrial septum into the left atrium.

(ii) The guidewire with the device are now advanced through the Mitral annulus into the LV and then through the point chosen of the LV muscle into the pericardium.

(iii) The external anchor is opened and the device is retracted back to prevent bleeding.

(iv) The device is then further retracted until above the Mitral annulus and the second (annular) anchor is opened.

(v) The distance between the two anchors is now gradually shortened along the tension member until the desired Mitral leaflets coaptation is achieved.

(vi) The anchor is secured in place to the tension member and the guidewire is cut and pulled out.

Catheter Approach when Used for Cardiomyopathy (i) A leading guidewire is inserted through the femoral or jugular vein (or any other big vein). Under TEE guidance the wire with the Device is advanced to the right atrium and through the atrial septum into the left atrium.

(ii) The guidewire with the device are now advanced through the Mitral annulus into the LV and then through the point chosen of the LV muscle into the pericardium.

(iii) The external anchor is opened and the device is retracted back to prevent bleeding.

(iv) The device is then further retracted until above the Mitral annulus and the second (annular) anchor is opened.

(v) A second (and third if needed) device is now applied with same technique in different LV points as planned according to the shape of the heart.

(vi) The distance between the coupled anchors is now gradually shortened along the tension members until the desired LV shape is achieved.

(vii) The anchors are secured in place to the tension member and the excess guidewire is cut and pulled out.

It should be noted that in the above protocols the device need not pass through the apex, for example, being 1, 2, 3, 4 or intermediate or more centimeters from the apex. Similarly, the device may not pass through papillary muscles.

In an exemplary embodiment of the invention, the device is provided as a temporary measure, for example, until surgery, as a prophylactic and/or until scar tissue is formed to stabilize the heart. For example, a device may be implanted soon after (e.g., less than or about 1, 2, 3, 4 or 5 weeks) an event of cardiac ischemia which damages cardiac tissue. In an exemplary embodiment of the invention, tensioning element 58 is made degradable in such access.

It should be noted that in some embodiments, what is desired is to prevent undesired distortion of the heart, but minimally interfere at other times. Optionally, tensioning member 58 is selected so that it applies tension only when the heart reaches certain geometries (e.g., end diastole). Optionally or alternatively, tensioning member 58 includes elasticity which is selected to minimally interfere at a first length, apply some force at a second length and apply an even greater force at a third length. The greater force possibly being selected to be effectively or actually a limit on cardiac motion.

In an exemplary embodiment of the invention, such temporally-partial partial tension, allows the cardiac tissue to work and remodel correctly.

In devices 52 and 82, first anchor 54 is optionally a substantially mesh material. A potential advantage of such a first anchor is that the plurality of holes through the mesh provides a user freedom as to how to orient and where to position the first anchor and tensioning members, including optionally easily allowing securing of a plurality of tensioning members.

In some embodiments, such as discussed above for devices 52, 82 and 92, are provided as a kit. In some embodiments, for example, a kit comprises a first anchor. In some embodiments, for example, a kit comprises a first anchor and a second anchor. In some embodiments, for example, a kit comprises a first anchor, a second anchor and tensioning member or members. In some embodiments, a kit is provided without a tensioning member. In some embodiments, a kit is provided with two (or more) tensioning members, precut to approximately the appropriate length. In some embodiments, a single long strand is provided, for example on a spool, and the desired number and lengths of tensioning members are cut from the provided strand. In some embodiments, a kit comprises an annuloplasty ring. In some embodiments, a tensioning member is provided with a needle at one end. In some embodiments, a tensioning member is provided with two needles, one at each end, for example for use in embodiments similar to device 52.

In device 52, first anchor 54 is fashioned ad hoc from surgical felt. In some embodiments, a first anchor of felt or similar material is provided preformed, for example as a part of a kit.

In the embodiments of methods for applying pressure to a portion of a heart described above, tensioning members 58 pass through a left ventricle 28 care is taken to avoid penetrating papillary muscles 44 so as not to affect the functioning thereof. In some embodiments, a tensioning member passes through a papillary muscle or a portion of a papillary muscle.

In the embodiments discussed above, a device for applying pressure to a portion of a heart is deployed together with or without an annuloplasty ring such as 80. In general, whether or not an annuloplasty ring is deployed with a device for applying pressure to a portion of a heart is determined by a treating physician.

In some embodiments, a device for applying pressure to a portion of a heart is deployed in a heart where an implantable prosthesis such as an annuloplasty ring or a prosthetic heart valve has previously been deployed, for example a few weeks, a few months or even a few years previously. In some such embodiments, a treating physician determines, for example, that there is insufficient mitral valve leaflet coaptation despite the presence of an annuloplasty ring or an artificial heart valve and therefore decides to deploy a device for applying pressure to a portion of the heart.

Reference is now made to FIGS. 18A-18D, which illustrate a Coronary Sinus (CS) guide 1800, acting as a CS ring, and made at least partly of shape memory material, in accordance with yet another alternative exemplary embodiment of the invention.

Figure 18A:
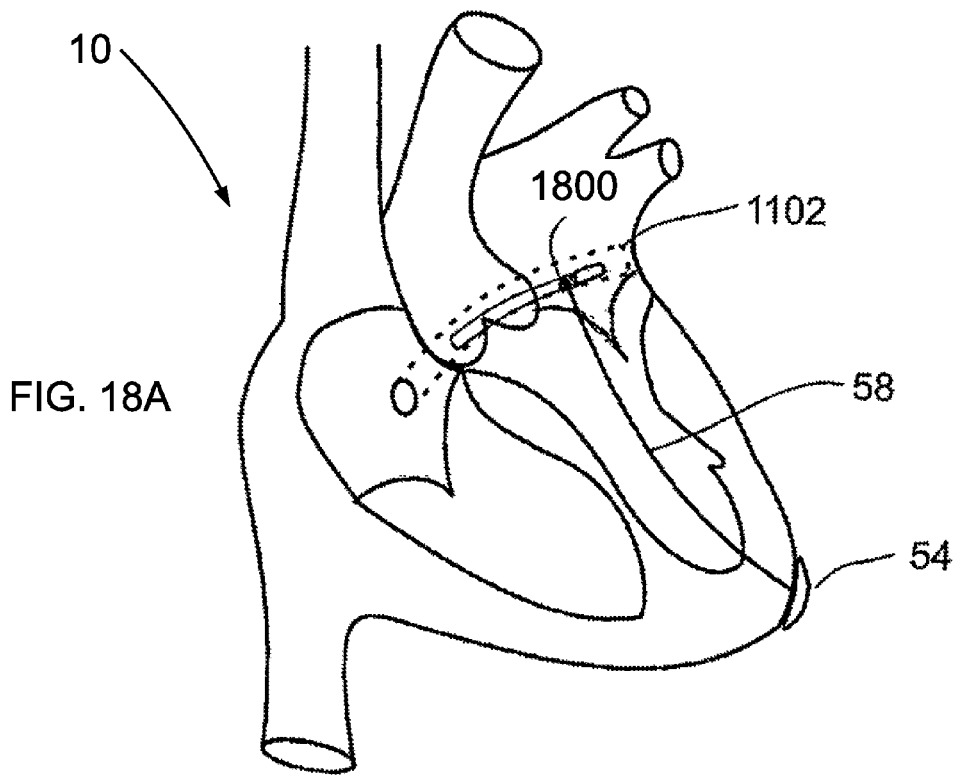
FIGS. 18A-18D illustrate a Coronary Sinus guide 1800, acting as a coronary sinus ring, and made at least partly of shape memory material, in accordance with yet another alternative exemplary embodiment of the invention.

FIG. 18A illustrates a typical human heart 10, within which the CS guide 1800 is placed in the Coronary Sinus 1102, serving as an anchor, optionally similarly to the Coronary Sinus guide 1000 described above after the description of FIG. 11I.

FIG. 18A also illustrates the first anchor 54 and the tensioning member 58 of FIG. 11H. The CS guide 1800, in its function as a CS ring, optionally exerts force on the heart tissue, optionally reshaping the heart tissue, and optionally modifying the shape of the mitral valve annulus.

Figure 18B:
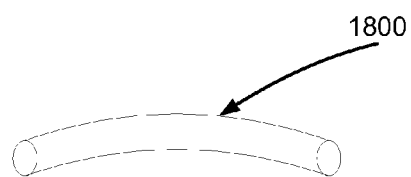

FIG. 18B depicts a simplified illustration of the CS guide 1800 in a shape suitable for insertion and navigation through the body up to the Coronary Sinus.

Figure 18C:
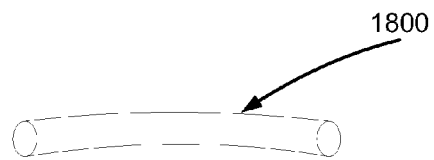

FIG. 18C depicts a simplified illustration of one example embodiment of the CS guide 1800 after the CS guide 1800 had optionally been induced to change its shape to a less curved shape than that of the CS guide 1800 as depicted in FIG. 18B, suitable for optionally reshaping the heart tissue.

Figure 18D:
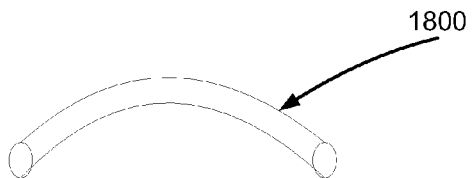

FIG. 18D depicts a simplified illustration of another example embodiment of the CS guide 1800 after the CS guide 1800 had optionally been induced to change its shape to a more curved shape than that of the CS guide 1800 as depicted in FIG. 18B, suitable for optionally reshaping the heart tissue.

FIGS. 18B, 18C, and 18D depict three optional shapes of the CS guide 1800, with the shapes depicted in FIGS. 18C, and 18D being achieved by inducing a shape memory material to change shape from the shape depicted in FIG. 18*b*.

In some embodiments of the invention the change in shape of the CS guide 1800 is optionally achieved without use of a shape memory material, but through other methods of achieving shape change.

An example such method is by producing the CS guide 1800 as a component sensitive to temperature, which becomes more or less curved based on temperature. The component may, for example, be formed of a bi-metal for converting a temperature change into mechanical displacement. The bi-metallic component may, for example, be designed to be inserted colder than body temperature, and bend to be more or less curved upon warming to body temperature, or the bi-metallic component may be designed to be inserted warmer than body temperature, and bend to be more or less curved upon cooling to body temperature.

Another example such method is by inflating a curved balloon inside the CS guide 1800, shaping the CS guide 1800 into a desired curved shape.

Embodiments of the present invention are contemplated for use to alleviate functional mitral regurgitation, such as ischemic mitral regurgitation, (resulting, by way of a non-limiting example, from myocardial ischemia or infarction), and other myocardial disease (such as, by way of a non-limiting example, dilated cardiomyopathy).

Specific embodiments have been described herein primarily with reference to treating improperly functioning mitral valves resulting from cardiac remodeling, it is understood that in some embodiments the teachings herein are also applicable to other conditions, including other conditions where there is insufficient mitral valve leaflet coaptation.

In some embodiments, for example, the teachings herein are applied in conjunction with mitral valve replacement procedures, for example, certain cases of rheumatic heart disease, especially in cases where preservation of the subvalvular apparatus is not possible.

Specific embodiments of the present invention have been described herein primarily with reference to treatment of living human subjects. It is understood, however, that some embodiments of the present invention are performed for the veterinary treatment of a non-human mammal, especially horses, cats, dogs, cows and pigs.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

Section headings used should not be construed as necessarily limiting.

What is claimed is:

1. Cardiac tensioning apparatus, comprising:
   (a) an elongate tensioning element long enough to reach from a top of a heart ventricle to a bottom of the heart ventricle;
   (b) at least one first anchor adapted to couple said elongate tensioning element to cardiac tissue, at a first position along said elongate tensioning element; and
   (c) at least one second elongate anchor at a second position along said elongate tensioning element;
   wherein said at least one second anchor is a rigid rod-like element attached to said elongate tensioning element, rigid enough to limit movement of a wall of a beating heart.

2. The apparatus according to claim 1 and further comprising:
   a delivery tube sized for and adapted for insertion into a body; and
   a sharp tip adapted to be pushed through cardiac muscle, wherein said delivery tube encloses at least one of said tensioning element and said at least one anchor.

3. The apparatus according to claim 2, wherein said tube includes a separate guide wire channel.

4. The apparatus according to claim 2, comprising a guidewire which is sharp enough and stiff enough to penetrate cardiac muscle.

5. The apparatus according to claim 2 in which at least some of the delivery tube comprises shape memory material.

6. The apparatus according to claim 2 in which the delivery tube is configured to assume a substantially curved shape, for reshaping a mitral valve to a desired mitral valve annulus shape.

7. The apparatus according to claim 2, wherein the delivery tube is long enough and stiff enough to modify a shape of a mitral valve annulus.

8. The apparatus according to claim 2, wherein the delivery tube comprises a rigid curved cylinder of stainless steel.

9. The apparatus according to claim 2 in which said delivery tube is configured to serve as the second anchor.

10. The apparatus according to claim 1, in which said second anchor is mounted on said elongate tensioning element and configured to anchor said elongate tensioning element to different cardiac muscle tissue at a spaced apart position from said at least one anchor.

11. The apparatus according to claim 1, wherein said at least one anchor and said second anchor are configured to be urged against opposite parts of said heart by said elongate tensioning element.

12. The apparatus according to claim 1, wherein said at least one anchor and said second anchor are adapted to not engage said heart absent tension from said elongate tensioning element.

13. The apparatus according to claim 1, wherein one or both of said at least one anchor and said second anchor are adapted to be axially moved along said elongate tensioning element.

14. The apparatus according to claim 1, wherein said at least one anchor includes a locking mechanism for selectively locking at a desired position along said elongate tensioning element.

15. The apparatus according to claim 1, wherein said first anchor is preassembled with said elongate tensioning element.

16. The apparatus according to claim 1, wherein said at least one first anchor is configured to lie on an outside of a left ventricle and is in the form of a pad.

17. The apparatus according to claim 1, wherein said at least one first anchor is configured to lie on an outside of a left ventricle and has a surface area for contact with said surface, of at least 6 sq. cm.

18. The apparatus according to claim 1, wherein said at least one first anchor is a rod like element.

19. The apparatus according to claim 1, wherein said elongate tensioning element is configured for dissipating after less than 6 months.

20. The apparatus according to claim 1, wherein said elongate tensioning element has an adjustable length of between 4 and 15 cm.

21. The apparatus according to claim 1 in which said elongate tensioning element comprises one of a group consisting of: a fiber; a filament; a ribbon; a cord; a rope; a strand; a thread; a cable; a wire; and a yarn.

22. The apparatus according to claim 21 in which said elongate tensioning element is elastic.

23. The apparatus according to claim 1 in which the second anchor has a diameter such that the second anchor does not block blood flow through the coronary sinus.

24. The apparatus according to claim 1 in which the second anchor has a semicircular cross section such that the second anchor does not block blood flow through the coronary sinus.

25. The apparatus according to claim 1 in which the second anchor anchors a plurality of elongate tensioning elements.

26. The apparatus according to claim 1 in which said at least one second anchor is shaped and sized to be located along and above the mitral valve annulus.

27. The apparatus according to claim 1 in which said at least one second anchor is shaped and sized to anchor from inside the coronary sinus of the heart.

28. The apparatus according to claim 1 in which said at least one second anchor is shaped and sized to be located at a location in a heart atrium where an annuloplasty ring is typically located.

29. The apparatus according to claim 1, wherein said second anchor includes a locking mechanism for selectively locking at a desired position along said elongate tensioning element.

30. The apparatus according to claim 1 in which said second anchor is attached to said elongate tensioning element substantially midway between ends of said rod-like element.

31. A method of applying mechanical tension to a heart, comprising:
(a) penetrating a first wall of the heart;
(b) second penetrating a second wall of the heart;
(c) coupling an elongate tensioning element long enough to reach from a top of a heart ventricle to a bottom of the heart ventricle to said second wall using at least one anchor at a first position along said elongate tensioning element; and
d) second coupling said elongate tensioning element to said first wall using a second rod-like anchor rigid enough to limit movement of a wall of a beating heart at a desired position along said elongate tensioning element,
wherein said second anchor is an element configured to assume a shape and size suitable for placement as an anchor adjacent to a mitral valve annulus.

32. The method according to claim 31, wherein said coupling and said second coupling comprise:
releasing an anchor distal to said second wall; and
releasing a second anchor proximal to said first wall.

33. The method according to claim 31, comprising adjusting a length of said elongate tensioning element inside said heart.

34. The method according to claim 31, comprising selecting a desired effect on said heart of said elongate tensioning element and selecting the locations of said penetrations in accordance with said selecting.

35. The method according to claim 31, comprising repeating at least one of said coupling and said second coupling for a plurality of elongate tensioning elements.

36. The method according to claim 31, wherein said coupling and said second coupling are selected so that said elongate tensioning element is not tensioned by said walls over the entire cycle of the heart.

37. The method of claim 31 in which the rod-like anchor comprises a rod of surgical felt.

38. The method of claim 31 in which the rod-like anchor is placed inside the coronary sinus of the heart.

39. The method of claim 31 in which the first anchor is placed at a bottom of the traverse pericardial sinus of the heart.

40. The method of claim 31 in which the rod-like anchor comprises a rigid curved cylinder of stainless steel.

41. Cardiac tensioning apparatus, comprising:
(a) an elongate tensioning element long enough to reach from a top of a heart ventricle to a bottom of the heart ventricle;
(b) at least one anchor adapted to couple said elongate tensioning element to cardiac tissue, at a first position along said elongate tensioning element; and
(c) at least one second elongate anchor at a second position along said elongate tensioning element;

wherein said at least one second anchor is shaped to engage an annuloplasty ring and comprises a hook adapted to engage a rod like element.

42. Cardiac tensioning apparatus, comprising:
(a) an elongate tensioning element long enough to reach from a top of a heart ventricle to a bottom of the heart ventricle;
(b) at least one anchor adapted to couple said elongate tensioning element to cardiac tissue, at a first position along said elongate tensioning element; and
(c) at least one second elongate anchor at a second position along said elongate tensioning element;
wherein said at least one second anchor comprises a hook sized and shaped to engage an annuloplasty ring.

* * * * *

UNITED STATES PATENT AND TRADEMARK OFFICE
CERTIFICATE OF CORRECTION

PATENT NO. : 9,131,928 B2  
APPLICATION NO. : 12/809641  
DATED : September 15, 2015  
INVENTOR(S) : Amnon Zlotnick et al.

Page 1 of 1

It is certified that error appears in the above-identified patent and that said Letters Patent is hereby corrected as shown below:

On the Title page, item (54) and in the Specification, Column 1, line 2, in the Title section, Change "A HEART" to --A CORONARY SINUS--

Signed and Sealed this  
Tenth Day of May, 2016

Michelle K. Lee  
*Director of the United States Patent and Trademark Office*